United States Patent
Finlay

(10) Patent No.: US 12,421,310 B2
(45) Date of Patent: Sep. 23, 2025

(54) CD47 BINDING AGENTS

(71) Applicant: CENTESSA PHARMACEUTICALS (UK) LIMITED, Altrincham (GB)

(72) Inventor: William James Jonathan Finlay, Glasgow (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 1081 days.

(21) Appl. No.: 17/041,100

(22) PCT Filed: Mar. 27, 2019

(86) PCT No.: PCT/EP2019/057723
§ 371 (c)(1),
(2) Date: Sep. 24, 2020

(87) PCT Pub. No.: WO2019/185717
PCT Pub. Date: Oct. 3, 2019

(65) Prior Publication Data
US 2021/0179711 A1    Jun. 17, 2021

(30) Foreign Application Priority Data

Mar. 27, 2018 (GB) .................................... 1804860
Aug. 22, 2018 (GB) .................................... 1813693

(51) Int. Cl.
| | |
|---|---|
| C07K 16/28 | (2006.01) |
| A61K 39/00 | (2006.01) |
| A61K 45/06 | (2006.01) |
| A61K 47/68 | (2017.01) |

(52) U.S. Cl.
CPC .......... C07K 16/2803 (2013.01); A61K 45/06 (2013.01); A61K 47/6849 (2017.08); *A61K 2039/505* (2013.01); *C07K 2317/14* (2013.01); *C07K 2317/24* (2013.01); *C07K 2317/31* (2013.01); *C07K 2317/565* (2013.01); *C07K 2317/567* (2013.01); *C07K 2317/622* (2013.01)

(58) Field of Classification Search
CPC .......... C07K 16/2803; C07K 2317/565; A61K 2039/505; A61K 47/6849
See application file for complete search history.

(56) References Cited

U.S. PATENT DOCUMENTS

| | | |
|---|---|---|
| 9,158,117 B2 | 10/2015 | Li et al. |
| 9,221,908 B2 | 12/2015 | Frazier et al. |
| 9,518,117 B2 | 12/2016 | Frazier et al. |
| 10,259,873 B2 | 4/2019 | Frazier et al. |
| 10,683,350 B2 | 6/2020 | Finlay et al. |
| 11,370,840 B2 | 6/2022 | Finlay |
| 2014/0140989 A1 | 5/2014 | Eckelman et al. |
| 2017/0073395 A1 | 3/2017 | Finlay et al. |
| 2020/0277375 A1 | 9/2020 | Finlay et al. |
| 2022/0332819 A1 | 10/2022 | Finlay |

FOREIGN PATENT DOCUMENTS

| | | | |
|---|---|---|---|
| KR | 20060121150 A | 11/2006 | |
| WO | WO-2008083949 A2 | 7/2008 | |
| WO | WO-2011143624 A2 * | 11/2011 | ............. A61P 35/00 |
| WO | WO 2013/119714 A1 | 8/2013 | |
| WO | WO 2014/093678 A2 | 6/2014 | |
| WO | WO 2015/191861 A1 | 12/2015 | |
| WO | WO 2016/081423 A1 | 5/2016 | |
| WO | WO 2016/109415 A1 | 7/2016 | |
| WO | WO 2017/049251 A2 | 3/2017 | |
| WO | WO 2017/053423 A1 | 3/2017 | |
| WO | WO 2017/121771 A1 | 7/2017 | |
| WO | WO 2017/181033 A1 | 10/2017 | |
| WO | WO-2019034895 A1 | 2/2019 | |
| WO | WO-2019185717 A1 | 10/2019 | |

OTHER PUBLICATIONS

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Brown et al., J Immunol. May 1996;156(9):3285-91 (Year: 1996).*
Warzocha et al., Leukemia and Lymphoma (1997) vol. 24. pp. 267-281 (Year: 1997).*
Greenspan et al. 1999 Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Skolnick et al., Trends Biotechnol. Jan. 2000; 18(1):34-9 (Year: 2000).*
Vajdos et al., J Mol Biol. Jul. 5, 2002;320(2):415-28 at 416 (Year: 2002).*
Aagaard et al., Advanced Drug Delivery Reviews 59 (2007) 75-86 (Year: 2007).*
Guido et al., Curr Med Chem. 2008; 15(1):37-46 (Year: 2008).*
Mckeague et al., J Nucleic Acids. 2012;2012:748913. Epub Oct. 2, 20124 (Year: 2012).*
Clark et al., J. Med. Chem., 2014, 57 (12), pp. 5023-5038 (Year: 2014).*
Miosge, Proc Natl Acad Sci U S A. Sep. 15, 2015;112(37):E5189-98 (Year: 2015).*
Kulmanov et al., Bioinformatics, 34(4), 2018, 660-668 (Year: 2018).*
International Search Report and Written Opinion mailed Dec. 17, 2018 for International Application No. PCT/GB2018/052347, 19 pages.

(Continued)

*Primary Examiner* — Vanessa L. Ford
*Assistant Examiner* — Danaya L. Middleton
(74) *Attorney, Agent, or Firm* — Wilson Sonsini Goodrich & Rosati

(57) ABSTRACT

Provided herein are antibody molecules that bind specifically to CD47 and related nucleic acid molecules, vectors and host cells. Also provided herein are medical uses of such antibody molecules.

28 Claims, 29 Drawing Sheets
Specification includes a Sequence Listing.

(56) References Cited

OTHER PUBLICATIONS

UKIPO Search Report dated May 23, 2018 for GB Application No. GB1713298.6, 1 page.

International Search Report and Written Opinion mailed Jul. 18, 2019 for International Application No. PCT/EP2019/057723, 19 pages.

Ahmadi, M. et al., "Small Amounts of Sub-Visible Aggregates Enhance the Immunogenic Potential of Monoclonal Antibody Therapeutics," Pharm Res, 32:1383 (2005); https://doi.org/10.1007/s11095-014-1541-x, 12 pages.

Almagro, J. C. & Fransson, J., "Humanization of antibodies," Frontiers in Bioscience, 13:1619-1633 (2008).

Bagshawe, K. D. et al., "Antibody-Enzyme Conjugates Can Generate Cytotoxic Drugs from Inactive Precursors at Tumor Sites," Antibody, Immunoconjugates, and Radiopharmaceuticals, 4(4):915-922 (1991).

Casipit, C. L. et al., "Improving the binding affinity of an antibody using molecular modeling and site-directed mutagenesis," Protein Science, 7:1671-1680 (1998).

Chien, N. C. et al., "Significant structural and functional change of an antigen-binding site by a distant amino acid substitution: Proposal of a structural mechanism," Proc. Natl. Acad. Sci. USA, 86:5532-5536 (1989).

Fennell, B. J. et al., "CDR-restricted engineering of native human scFvs creates highly stable and soluble bifunctional antibodies for subcutaneous delivery," mAbs, 5(6):882-895 (2013).

Finlay, W. J. et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol., 388:541-558 (2009).

Finlay, W. J. J. et al., "Optimized Generation of High-Affinity, High-Specificity Single-Chain Fv Antibodies from Multiantigen Immunized Chickens," Dermot Walls and Sinéad T. Loughran (eds.), Protein Chromatography: Methods and Protocols, Methods in Molecular Biology, vol. 681; doi: 10.1007/978-1-60761-913-0_21, 19 pages (2011).

Glockshuber, R. et al., "Mapping and Modification of an Antibody Hapten Binding Site: A Site-Directed Mutagenesis Study of McP603," Biochemistry, 30:3049-3054 (1991).

Harding, F. A. et al., "The immunogenicity of humanized and fully human antibodies. Residual immunogenicity resides in the CDR regions," mAbs, 2(3):256-265 (2010).

Henikoff, S. & Henikoff, J. G., "Amino acid substitution matrices from protein blocks," Proc. Natl. Acad. Sci. USA, 89:10915-10919 (1992).

Holliger, P. & Hudson, P. J., "Engineered antibody fragments and the rise of single domains," Nature Biotechnology, 23(9):1126-1136 (2005).

Hwang, W. Y. K. & Foote, J., "Immunogenicity of engineered antibodies," Methods, 36:3-10 (2005).

Jones, P. T. et al., "Replacing the complementarity-determining regions in a human antibody with those from a mouse," Nature, 321:522-525 (1986).

Kobayashi, H. et al., "Tryptophan H33 plays an important role in pyrimidine (6-4) pyrimidone photoproduct binding by a high-affinity antibody," Protein Engineering, 12(10):879-884 (1999).

Kobrin, B. J. et al., "A V region mutation in a phosphocholine-binding monoclonal antibody results in loss of antigen binding," J Immunol., 146:2017-2020 (1991).

Ledermann, J. A. et al., "A Phase-I Study of Repeated Therapy with Radiolabelled Antibody to Carcinoembryonic Antigen Using Intermittent or Continuous Administration of Cyclosporin A to Suppress the Immune Response," Int. J. Cancer, 47:659-664 (1991).

Melero, I. et al., "Agonist Antibodies to TNFR Molecules That Costimulate T and NK Cells," Clin Cancer Res, 19(5):1044-1053 (2013), and Correction, p. 1913.

Mouquet, H. et al., "Polyreactivity increases the apparent affinity of anti-HIV antibodies by heteroligation," Nature, 467(7315):591-595 (2010); doi:10.1038/nature09385.

Nelson, A. L. et al., "Development trends for human monoclonal antibody therapeutics," Nature Reviews Drug Discovery, 9:767-774 (2010).

North, B. et al., "A New Clustering of Antibody CDR Loop Conformations," J. Mol. Biol. (2010); doi:10.1016/j.jmb.2010.10.030, 29 pages.

Panka, D. J. et al., Defining the structural correlates responsible for loss of arsonate affinity in an $Id^{CR}$ antibody isolated from an autoimmune mouse, Molecular Immunology, 30(11):1013-1020 (1993).

Rudikoff, S. et al., "Single amino acid substitution altering antigen-binding specificity," Proc. Natl. Acad. Sci. USA, 79:1979-1983 (1982).

Schildbach, J. F. et al., "Modulation of antibody affinity by a non-contact residue," Protein Science, 2:206-214 (1993).

Swindells, M. B. et al., "abYsis: Integrated Antibody Sequence and Structure-Management, Analysis, and Prediction," J. Mol. Biol., 429:356-364 (2017).

Tiller, T et al., "A fully synthetic human Fab antibody library based on fixed VH/VL framework pairings with favorable biophysical properties," mAbs, 5(3):1-26 (2013).

Townsend, S. et al., "Augmented Binary Substitution: Single-pass CDR germ-lining and stabilization of therapeutic antibodies," PNAS, 112(50):15354-15359 (2015).

Tu, C. et al., "Combination of Structural and Empirical Analyses Delineates the Key Contacts Mediating Stability and Affinity Increases in an Optimized Biotherapeutic Single-chain Fv (ScFv)," The Journal of Biological Chemistry, 291(3):1267-1276 (2016).

Van Aerts, L. Agjm et al., "Biosimilars entering the clinic without animal studies," mAbs, 6(5):1155-1162 (2014).

Van Meer, P. J. K. et al., "Immunogenicity of mAbs in non-human primates during nonclinical safety assessment," mAbs, 5(5):810-816 (2013).

Winkler, K. et al., "Changing the Antigen Binding Specificity by Single Point Mutations of an Anti-p24 (HIV-1) Antibody," J Immunol, 165:4505-4514 (2000).

Zhou, F. et al., "A general user interface for prediction servers of proteins' post-translational modification sites," Nature Protocols, 1(3): 1318-1321 (2006).

Yarilin, A. A. et al., Fundamentals of Immunology, p. 171 and p. 172-173 (1999), with English translation, 8 pages.

Yu, J. and M.F. Lin (Apr. 2005) Anti-CD47 monoclonal antibody (B6H12) impairs the maturation and function of human dendritic cells, J Exp Hematol (Zhongguo Shi Yan Xue Ye Xue Za Zhi), 13(2):192-197. English Abstract only.

Bork, et al., Go hunting in sequence databases but watch out for the traps. Trends in Genetics 1996; 12:425-427.

Bork, P., Powers and pitfalls in Sequence analysis: The 70% hurdle. Genome Research 2000; 10:398-400.

BRENNER: Errors in genome annotation. Trends in Genetics. 15:132-133 (1999).

Doerks et al.: Protein annotation: detective work for function prediction. Trends in Genetics. 14:248-250 (1998).

Paul, W.E. Fundamental Immunology, Third Edition (textbook). "Fv Structure and Diversity in Three Dimensions" pp. 292-295; Raven Press, New York (1993).

Sela-Culang et al. The structural basis of antibody-antigen recognition. Front Immunol. 4:302 (2013).

Skolnick et al.: From genes to protein structure and function: novel applications of computational approaches in the genomic era. Trends Biotechnol. 18(1):34-39 (2000).

Smith et al.: The challenges of genome sequence annotation or "the devil is in the details". Nature Biotechnol. 15:1222-1223 (1997).

Gokarn, Yatin R. et al. Self-buffering antibody formulations. Journal of pharmaceutical sciences 97(8):3051-3066 (2008).

MacCallum, Robert M. et al. Antibody-Antigen Interactions: Contact Analysis and Binding Site Topography. Journal of Molecular Biology 262(5):732-745 (1996).

U.S. Appl. No. 16/543,884, filed Aug. 19, 2029, inventor William James Jonathan Finlay; Non-Final Office Action dated Dec. 9, 2019, 10 pages.

(56) References Cited

OTHER PUBLICATIONS

U.S. Appl. No. 16/543,884, filed Aug. 19, 2029, inventor William James Jonathan Finlay; Notice of Allowance dated Apr. 7, 2020, 7 pages.
U.S. Appl. No. 16/877,938, filed May 17, 2020, inventor William James Jonathan Finlay; Notice of Allowance dated Feb. 18, 2022, 10 pages.
U.S. Appl. No. 17/849,101, filed Jun. 24, 2022, inventor William James Jonathan Finlay; Office Action dated Jan. 17, 2024, 8 pages.
U.S. Appl. No. 17/849,101, filed Jun. 24, 2022, inventor William James Jonathan Finlay; Office Action dated Jun. 21, 2024, 10 pages.
Wang, Wei. et al. Antibody Structure, Instability, and Formulation. Journal of Pharmaceutical Sciences 96(1):1-26 (2007).
Hollevoet, Kevin, et al., State of Play and Clinical Prospects of Antibody Gene Transfer. Journal of Translational Medicine 15(1): 19 Pages (2017).
STROHL: Current progress in innovative engineered antibodies. Protein Cell. 9(1):86-120 (2018).
U.S. Appl. No. 16/543,884 Non-Final Office Action dated Dec. 9, 2019.
U.S. Appl. No. 16/543,884 Notice of Allowance dated Apr. 7, 2020.
U.S. Appl. No. 16/877,938 Notice of Allowance dated Feb. 18, 2022.
U.S. Apppl. No. 17/849,101 Office Action dated Jan. 17, 2024.
Van Hoecke, et al. How mRNA therapeutics are entering the monoclonal antibody field. J Transl Med. Feb. 22, 2019;17(1):54. doi: 10.1186/s12967-019-1804-8.

* cited by examiner

CD47 BINDING AGENTS

CROSS-REFERENCE TO RELATED APPLICATIONS

This application is a 35 U.S.C. § 371 national phase application of International Patent Application No. PCT/EP2019/057723, filed on Mar. 27, 2019, which claims the benefit of GB Patent Application No. 1813693.7, filed on Aug. 22, 2018 and GB Patent Application No. 1804860.3, filed on Mar. 27, 2018, the disclosure of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ULTW_001_02US_SeqList_ST25.txt, date recorded: Sep. 25, 2020, file size ~145,970 bytes).

FIELD OF THE INVENTION

The invention relates to antibody molecules binding specifically to CD47 (Cluster of Differentiation 47, also known as integrin associated protein [IAP]) and medical uses thereof.

BACKGROUND OF THE INVENTION

CD47 (also known as integrin associated protein [IAP]) is a transmembrane protein that belongs to the immunoglobulin superfamily and binds to several known partners, including: membrane integrins, thrombospondin-1 (TSP-1) and signal-regulatory protein alpha (SIRPα). CD47 is associated with a range of cellular processes, including apoptosis, proliferation, adhesion, and migration of cells and, importantly, it plays a key role in immune and angiogenic responses. CD47-SIRPα signalling is a critical molecular interaction that inhibits the activation of phagocytosis by macrophages and other myeloid cells. This promotes the survival of tumour cells and therefore acts as a myeloid lineage-specific immune checkpoint.

Preclinical evidence suggests that blocking CD47-SIRPα signalling can enhance the phagocytic activity of macrophages and inhibit the growth of xenografts in numerous experimental models of both haematological and solid malignancies. As macrophage activity is also a recognised factor in the biology of inflammation-associated tissue remodelling such as tissue fibrosis and the formation of atherosclerotic plaques, the CD47-SIRPα signalling axis is also of considerable therapeutic potential in non-cancerous diseases. Hence, anti-CD47 mAbs have the potential to act as immunotherapeutic agents in cancer and other settings, and to amplify the effectiveness of currently established therapies.

The majority of currently approved antibody therapeutics are derived from immunized rodents. Many of those antibodies have undergone a process known as "humanization", via the "grafting" of murine CDRs into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as anti-CD47, which potentially engage immune effector functions as part of their mechanism of action, are at particularly high risk for immunogenicity as they can encourage phagocytosis of CD47+ target cells, leading to antigen processing of the antibody along with the target cell. These anti-drug antibody responses in the patient can reduce drug half-life, potency and safety during clinical use. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized agonistic anti-CD47 antibody would therefore have as many identical residues as possible in the v-domains to those found in both the frameworks and CDRs of well-characterized human germline sequences. Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, leaving antibodies at high risk of development difficulties. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained, including in this instance: target binding specificity, affinity to CD47 from both human and animal test species (e.g. cynomolgus monkey, also known as the crab-eating macaque, i.e. *Macaca fascicularis*), v-domain biophysical stability and/or IgG expression yield. Antibody engineering studies have shown that mutation of even single residue positions in key CDRs can have dramatic effects on all of these desired molecular properties.

WO2011143624A2 describes an antagonistic murine anti-CD47 IgG molecule termed "5F9G4", and also the preparation of humanized forms of 5F9G4 (h5F9G4). Those humanized forms of 5F9G4 were produced using classical humanization techniques, i.e. by grafting of Kabat-defined murine CDRs into human heavy and light chain framework sequences, with some of the human framework residues being potentially back-mutated to the correspondingly positioned 5F9G4 murine residues. For reasons noted above, such humanized forms of 5F9G4 described in WO2011143624A2 are not ideal.

SUMMARY OF THE INVENTION

The present invention provides a number of anti-CD47 antibodies and medical uses thereof.

According to one aspect of the invention, there is provided an antibody molecule or an antigen-binding portion thereof, which specifically binds to human CD47, and optionally also to cynomolgus monkey CD47, wherein the antibody comprises a heavy chain variable (VH) region and a light chain variable (VL) region. In some embodiments, the VH region comprises an IGHV5-51-based or an IGHV1-3-based framework. In some embodiments, the VL region comprises an IGKV2-28-based framework.

In the IGHV5-51 background, the anti-CD47 antibody molecule or antigen-binding portion may comprise a heavy chain variable region with:
- an HCDR1 having amino acids in sequence in the following order: G-Y-S-F-T-N or a conservative substitution of N (such as S)-Y-N or a conservative substitution of N (such as S)-M or a conservative substitution of M (such as I)-H or any amino acid (such as G) (SEQ ID NO:28);
- an HCDR2 having amino acids in sequence in the following order: M or a conservative substitution of M (for example, I)-G-T or any amino acid (such as I)-I-Y-P-G-N or any amino acid (such as D)-D or any amino acid (such as S)-D-T-S or any amino acid (such as R)-Y-N or any amino acid (such as S, H)-Q or any amino acid (such as P)-K or any amino acid (such as S)-F-Q/K-G/D (SEQ ID NO:29); and
- an HCDR3 having amino acids in sequence in the following order: G or any amino acid (such as Q)-G-Y or any amino acid (such as A, C, D, E, F, G, H, I, K, L, M, N, Q, R, S, T, V, W)-R-A or any amino acid (such as I, T, V, W)-M or any amino acid (such as A, E, K, L, P, Q, R, S, T, V, W)-D-Y (SEQ ID NO:30).

In the IGHV1-3 background, the anti-CD47 antibody molecule or antigen-binding portion may comprise a heavy chain variable region with:
- an HCDR1 having amino acids in sequence in the following order: G-Y-T-F-T-N or any amino acid (such as D)-Y-N or any amino acid (such as A)-M-H (SEQ ID NO:31);
- an HCDR2 having amino acids in sequence in the following order: M-G-T-I-Y-P-G-N-D-D or any amino acid (such as N)-T-S or any amino acid (such as K)-Y-N or any amino acid (such as S)-Q-K-F-Q-G (SEQ ID NO:32); and
- an HCDR3 having amino acids in sequence in the following order: G or any amino acid (such as Q)-G-Y or any amino acid (such as A, C, D, E, F, G, H, I, K, L, M, N, Q, R, S, T, V, W)-R A or any amino acid (such as I, T, V, W)-M or any amino acid (such as A, E, K, L, P, Q, R, S, T, V, W)-D-Y (SEQ ID NO:30).

In aspects of the invention, the HCDR1 of the antibody molecule or antigen-binding portion may exclude the sequence GYTFTNYNMH (SEQ ID NO:33; 5F9G4 murine/humanized antibody HCDR1 disclosed in WO2011143624A2; US20130142786A1), the HCDR2 of the antibody molecule or antigen-binding portion may exclude the sequence MGTIYPGNDDTSYNQKFKD (SEQ ID NO:34; 5F9G4 murine/humanized antibody HCDR2 disclosed in WO2011143624A2; US20130142786A1), and/or the HCDR3 of the antibody molecule or antigen-binding portion may exclude the sequence GGYRAMDY (SEQ ID NO:35; 5F9G4 murine/humanized antibody HCDR3 disclosed in WO2011143624A2; US20130142786A1).

The antibody molecule or antigen-binding portion may further comprise a light chain variable region with:
- an LCDR1 having amino acids in sequence in the following order: R-S-S-Q-S-I or a conservative substitution of I (such as L)-V or a conservative substitution of V (such as L)-Y or a conservative substitution of Y (such as H)-S-N or any amino acid (such as G, S, K)-G or any amino acid (such as A, Y)-N or any amino acid (such as Q, Y)-T or any amino acid (such as N)-Y-L-G or any amino acid (such as D) (SEQ ID NO:36);
- an LCDR2 having amino acids in sequence in the following order: K-V or any amino acid (such as G)-S-N-R-F or any amino acid (such as A, S)-S(SEQ ID NO:37); and
- an LCDR3 having amino acids in sequence in the following order: F or any amino acid (such as L, M)-Q-G or any amino acid (such as A)-S or any amino acid (such as T, L, M)-H or any amino acid (such as Q, R)-V or any amino acid (such as I, T)-P-Y-T or any amino acid (such as I) (SEQ ID NO:38).

In aspects of the invention, the LCDR1 of the antibody molecule or antigen-binding portion may exclude the sequence RSSQSIVYSNGNTYLG (SEQ ID NO:39; 5F9G4 murine/humanized antibody LCDR1 disclosed in WO2011143624A2; US20130142786A1), and/or the LCDR2 of the antibody molecule or antigen-binding portion may exclude the sequence KVSNRFS (SEQ ID NO:40; 5F9G4 murine/humanized antibody LCDR2 disclosed in WO2011143624A2; US20130142786A1), and/or the LCDR3 of the antibody molecule or antigen binding portion may exclude the sequence FQGSHVPYT (SEQ ID NO:41).

In some aspects, disclosed herein is an anti-CD47 antibody or an antigen-binding portion thereof, wherein the antibody comprises a heavy chain variable (VH) region and a light chain variable (VL) region, wherein
(a) the HCDR1 comprises the amino acid sequence G-Y-$X_1$-F-T-$X_2$-Y-$X_3$-$X_4$-$X_5$, wherein $X_1$ is S or a conservative substitution of S, $X_2$ is N or a conservative substitution of N, $X_3$ is N or any other amino acid, $X_4$ is M or a conservative substitution of M and $X_5$ is H or any other amino acid (SEQ ID NO:42);
(b) the HCDR2 comprises the amino acid sequence $X_1$-$X_2$-$X_3$-I-Y-P-G-$X_4$-$X_5$-$X_6$-T-$X_7$-Y-$X_8$-$X_9$-$X_{10}$-F-Q-G, wherein $X_1$ is M or a conservative substitution of M, $X_2$ is G or a conservative substitution of G, $X_3$ is T or any other amino acid, $X_4$ is N or a conservative substitution of N, $X_5$ is D or any other amino acid, $X_6$ is D or any other amino acid, $X_7$ is S or any other amino acid, $X_8$ is N or any other amino acid, $X_9$ is Q or any other amino acid and $X_{10}$ is K or any other amino acid (SEQ ID NO:43);
(c) the HCDR3 comprises the amino acid sequence $X_1$-G-$X_2$-R-$X_3$-$X_4$-D-Y, wherein $X_1$ is G or any other amino acid, $X_2$ is Y or any other amino acid, $X_3$ is A or any other amino acid and $X_4$ is M or any other amino acid (SEQ ID NO:44);
(d) the LCDR1 comprises the amino acid sequence R-S-S-Q-S-$X_1$-$X_2$-$X_3$-S-$X_4$-$X_5$-$X_6$-$X_7$-Y-L-$X_8$, wherein $X_1$ is I or a conservative substitution of I, $X_2$ is V or a conservative substitution of V, $X_3$ is Y or a conservative substitution of Y, $X_4$ is N or any other amino acid, $X_5$ is G or any other amino acid, $X_6$ is N or any other amino acid, $X_7$ is T or any other amino acid and $X_8$ is G or any other amino acid (SEQ ID NO:45);

(e) the LCDR2 comprises the amino acid sequence K-$X_1$-S-N-R-$X_2$-S, wherein $X_1$ is V or any other amino acid and $X_2$ is F or any other amino acid (SEQ ID NO:46); and (f) the LCDR3 comprises the amino acid sequence $X_1$-Q-$X_2$-$X_3$-$X_4$-$X_5$-P-Y-$X_6$, wherein $X_1$ is F or any other amino acid, $X_2$ is G or any other amino acid, $X_3$ is S or any other amino acid, $X_4$ is H or any other amino acid, $X_5$ is V or any other amino acid, $X_6$ is T or any other amino acid (SEQ ID NO:47).

In some aspects, the invention provides an anti-CD47 antibody or an antigen-binding portion thereof, wherein the antibody comprises a heavy chain variable (VH) region and a light chain variable (VL) region, wherein (a) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASHVPYT (SEQ ID NO:53);

(b) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNGNTYLG (SEQ ID NO:51), LCDR2 of KGSNRFS (SEQ ID NO:52) and LCDR3 of FQASHVPYT (SEQ ID NO:53);

(c) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNAYNYLG (SEQ ID NO:56), LCDR2 of KGSNRFS (SEQ ID NO:52) and LCDR3 of FQASHVPYT (SEQ ID NO:53);

(d) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNAYNYLG (SEQ ID NO:56), LCDR2 of KGSNRFS (SEQ ID NO:52) and LCDR3 of FQASQVPYT (SEQ ID NO:54);

(e) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASQVPYT (SEQ ID NO:54);

(f) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNGNTYLG (SEQ ID NO:51), LCDR2 of KGSNRFS (SEQ ID NO:52) and LCDR3 of FQASQVPYT (SEQ ID NO:54);

(g) the VH region amino acid sequence comprises HCDR1 of GYSFTNYNIH (SEQ ID NO:57), HCDR2 of MGTIYPGNSDTSYNPSFQG (SEQ ID NO: 61) and HCDR3 of GGVRAMDY (SEQ ID NO:62); and the VL region amino acid sequence comprises LCDR1 of RSSQSLLHSNGNTYLG (SEQ ID NO:51), LCDR2 of KGSNRFS (SEQ ID NO:52) and LCDR3 of MQASQVPYT (SEQ ID NO:63); or (h) the VH region amino acid sequence comprises HCDR1 of GYSFTNYNIH (SEQ ID NO:57), HCDR2 of MGTIYPGDSDTRYNPKFQG (SEQ ID NO:58) and HCDR3 of GGYRAEDY (SEQ ID NO:59); and the VL region amino acid sequence comprises LCDR1 of RSSQSLLHSNGNTYLG (SEQ ID NO:51), LCDR2 of KGSNRFS (SEQ ID NO:52) and LCDR3 of MQGSHVPY (SEQ ID NO:60).

In some aspects, disclosed herein is an anti-CD47 antibody or an antigen-binding portion thereof, wherein the antibody comprises a heavy chain variable (VH) region and a light chain variable (VL) region, wherein the VH region amino acid sequence comprises:
(a) HCDR1 of SEQ ID NO: 48 or SEQ ID NO: 57;
(b) HCDR2 of SEQ ID NO: 49 or SEQ ID NO: 61; and
(c) HCDR3 of SEQ ID NO: 50 or SEQ ID NO: 62; and the VL region amino acid sequence comprises:
(a') LCDR1 of SEQ ID NO: 51, SEQ ID NO: 55 or SEQ ID NO: 56;
(b') LCDR2 of SEQ ID NO: 52; and
(c') LCDR3 of SEQ ID NO: 53, SEQ ID NO: 54 or SEQ ID NO: 63.

In some aspects, disclosed herein is an anti-CD47 antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6;

(d) the VH region amino acid sequence comprises SEQ ID NO:7 and the VL region amino acid sequence comprises SEQ ID NO:8;

(e) the VH region amino acid sequence comprises SEQ ID NO:9 and the VL region amino acid sequence comprises SEQ ID NO:10;

(f) the VH region amino acid sequence comprises SEQ ID NO:11 and the VL region amino acid sequence comprises SEQ ID NO:12;

(g) the VH region amino acid sequence comprises SEQ ID NO:13 and the VL region amino acid sequence comprises SEQ ID NO:14; or (h) the VH region amino acid sequence comprises SEQ ID NO:15 and the VL region amino acid sequence comprises SEQ ID NO:16.

Also provided according to the invention is an immunoconjugate comprising the antibody molecule or antigen-binding portion thereof as defined herein linked to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-CD47 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the scFv as defined herein, or the immunoconjugate as defined herein, or the nucleic acid molecule as defined herein, or the vector as defined herein, or the pharmaceutical composition as defined herein, for use as a medicament. The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination with a second therapeutic agent, for example an anti cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The autoimmune disease or inflammatory disease may be selected in all aspects from the group consisting of: arthritis, asthma, multiple sclerosis, psoriasis, Crohn's disease, inflammatory bowel disease, lupus, Grave's disease and Hashimoto's thyroiditis, and ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease, an inflammatory disease or a fibrotic disease.

The cardiovascular disease in any aspect of the invention may for example be coronary heart disease or atherosclerosis.

The fibrotic disease in any aspect of the invention may for example be myocardial infarction, angina, osteoarthritis, pulmonary fibrosis, cystic fibrosis, bronchitis or asthma.

The invention also provides a method of producing an antibody molecule which specifically binds to human CD47 and optionally also to cynomolgus monkey CD47, or an antigen-binding portion thereof, comprising the steps of:
(1) grafting anti-CD47 CDRs from a non-human source into a human v-domain framework to produce a humanized anti-CD47 antibody molecule or antigen-binding portion thereof;
(2) generating a phage library of clones of the humanized anti-CD47 antibody molecule or antigen-binding portion thereof comprising one or more mutations in the CDRs;
(3) screening the phage library for binding to human CD47 and optionally also to cynomolgus monkey CD47;
(4) selecting clones from the screening step (3) having binding specificity to human CD47 and optionally also to cynomolgus monkey CD47; and
(5) producing an antibody molecule which specifically binds to human CD47 and optionally also to cynomolgus monkey CD47, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

DETAILED DESCRIPTION OF THE INVENTION

Figure 1A:
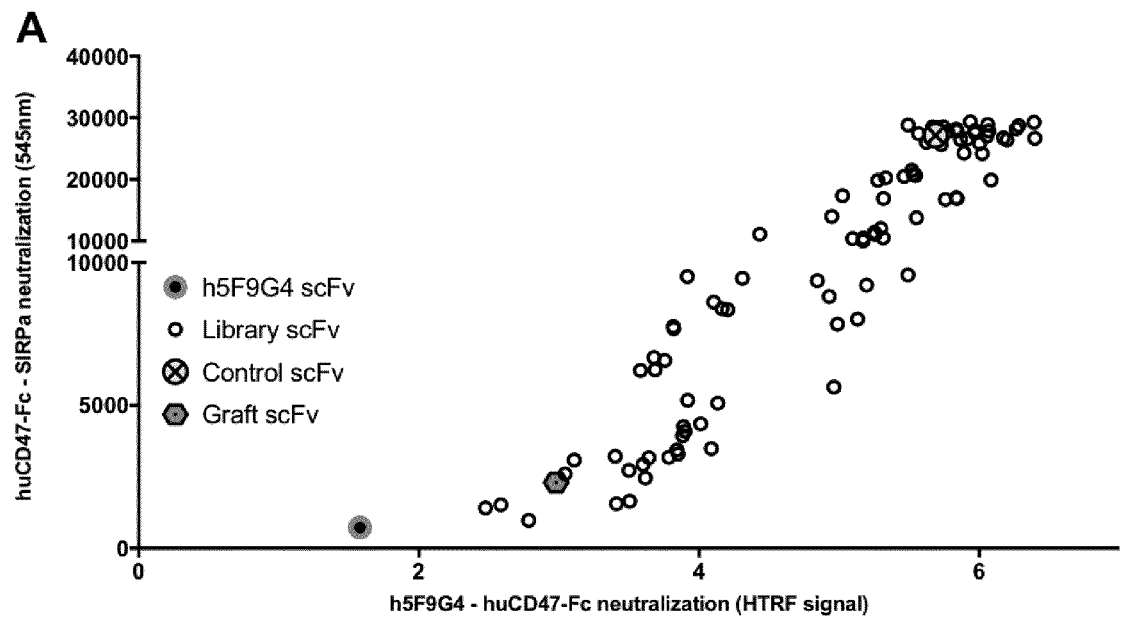
FIG. 1A-FIG. 1F. Assay technology known under the trademark HTRF®-based competition screening of library-derived anti-CD47 scFvs against h5F9G4 IgG1 and hSIRPα-Fc binding to human and cyno CD47-Fc proteins. Clones were derived from separate phage selection branches on biotinylated human and/or cynomolgus monkey CD47-Fc proteins in each round. After multiple rounds of selection in two branches, library-derived clones (black circles) were screened for binding against both human and cyno CD47-Fc and epitope blocking (measured via signal reduction) of h5F9G4 IgG1 and hSIRPα-Fc. Round 2 outputs (FIG. 1A, FIG. 1B). Round 3 outputs (FIG. 1C, FIG. 1D). Round 4 outputs (FIG. 1E, FIG. 1F). Negative control (non-CD47-binding) and positive control h5F9G4 scFvs are represented in grey crossed circle and black circle with grey border, respectively. In addition, an IGHV5-51/IGKV2-28 graft scFv was also included on each plate (grey hexagon).
Figure 1B:
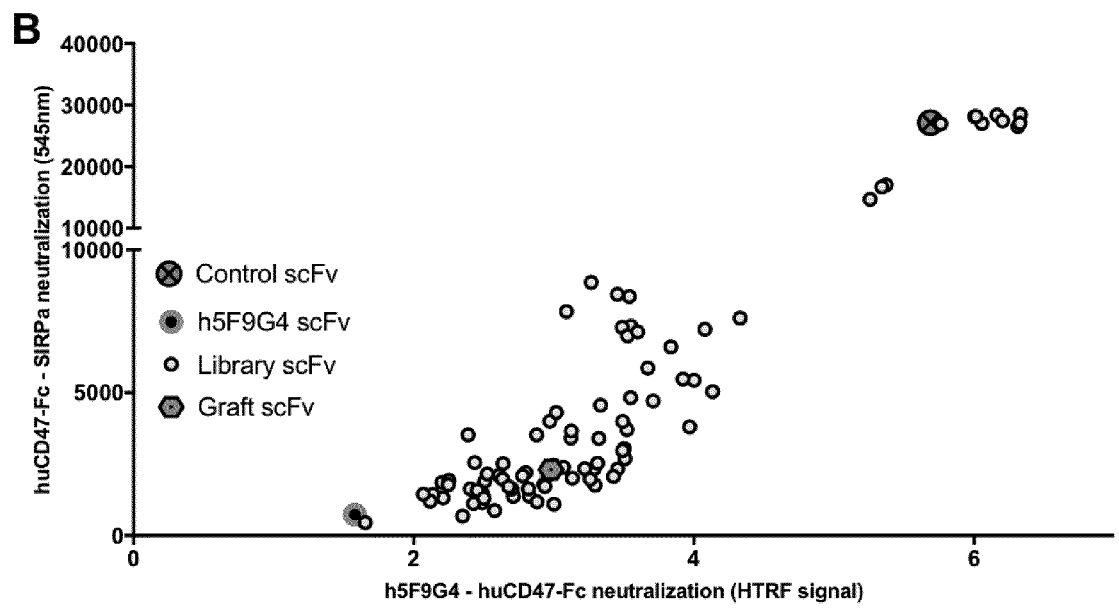
Figures 1C, 1D:
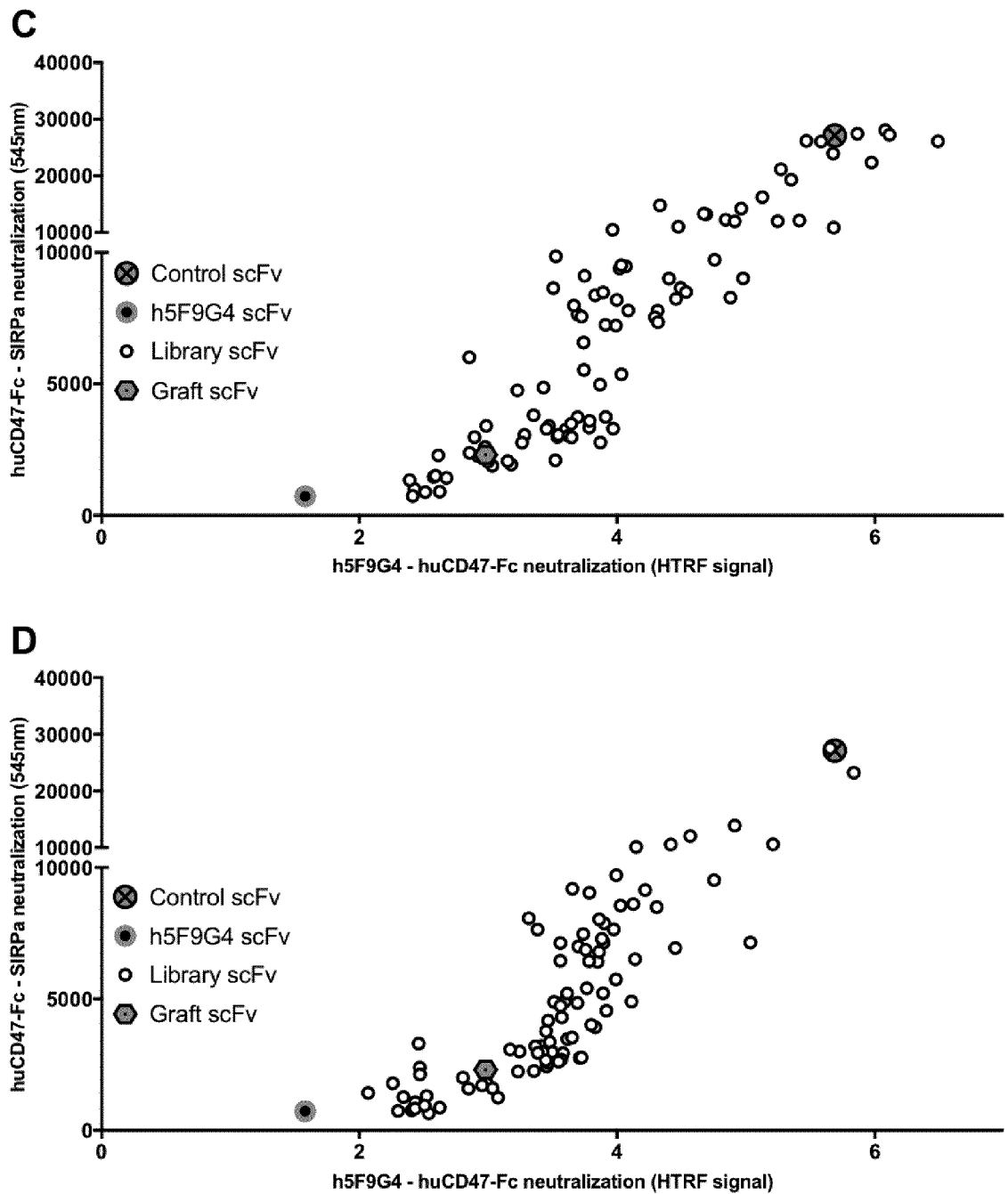
Figure 1E:
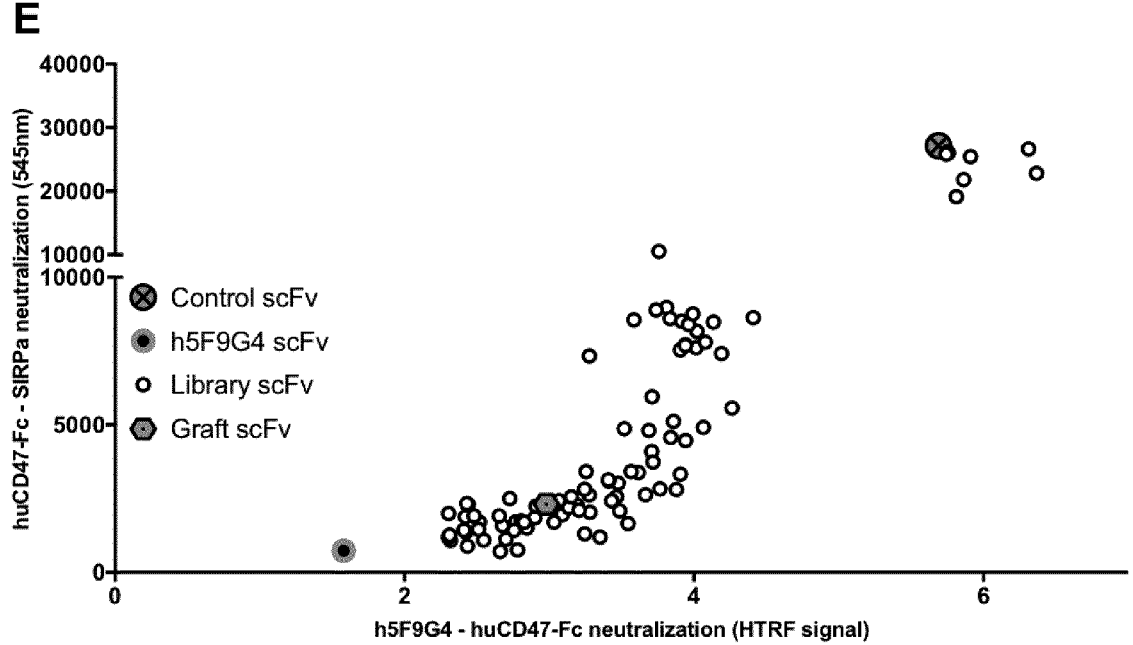
Figure 1F:
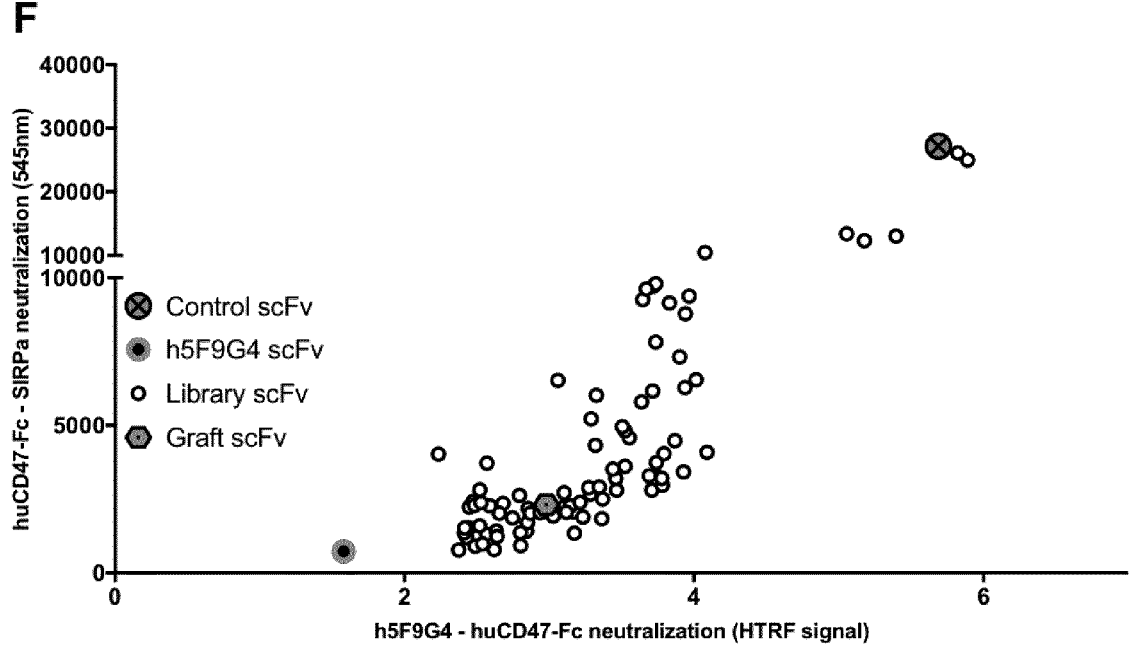

According to a first aspect of the invention, there is provided an antibody molecule which specifically binds to human CD47 and optionally also to cynomolgus monkey CD47, or an antigen-binding portion thereof, wherein the antibody molecule or antigen-binding portion comprises a heavy chain variable region with:

In the IGHV5-51 background; an HCDR1 having amino acids in sequence in the following order: G-Y-S-F-T-N or a conservative substitution of N (such as S)-Y-N or a conservative substitution of N (such as S)-M or a conservative substitution of M (such as I)-H or any amino acid (such as G) (SEQ ID NO:28);
   an HCDR2 having amino acids in sequence in the following order: M or a conservative substitution of M (for example, I)-G-T or any amino acid (such as I)-1-Y-P-G-N or any amino acid (such as D)-D or any amino acid (such as S)-D-T-S or any amino acid (such as R)-Y-N or any amino acid (such as S, H)-Q or any amino acid (such as P)-K or any amino acid (such as S)-F-Q-G (SEQ ID NO:29); and
   an HCDR3 having amino acids in sequence in the following order: G or any amino acid (such as Q)-G-Y or any amino acid (such as A, C, D, E, F, G, H, I, K, L, M, N, Q, R, S, T, V, W)-R-A or any amino acid (such as I, T, V, W)-M or any amino acid (such as A, E, K, L, P, Q, R, S, T, V, W)-D-Y (SEQ ID NO:30).

In some aspects an anti-CD47 antibody or antigen-binding portion provided herein specifically binds to a CD47 protein comprising or consisting of SEQ ID NO:24 or SEQ ID NO:25. In some aspects an anti-CD47 antibody or antigen-binding portion provided herein specifically binds to a CD47 protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:24 or SEQ ID NO:25.

In the IGHV1-3 background; an HCDR1 having amino acids in sequence in the following order: G-Y-T-F-T-N or any amino acid (such as D)-Y-N or any amino acid (such as A)-M-H (SEQ ID NO:31);
   an HCDR2 having amino acids in sequence in the following order: M-G-T-I-Y-P-G-N-D-D or any amino acid (such as N)-T-S or any amino acid (such as K)-Y-N or any amino acid (such as S)-Q-K-F-Q-G (SEQ ID NO:32); and
   an HCDR3 having amino acids in sequence in the following order: G or any amino acid (such as Q)-G-Y or any amino acid (such as A, C, D, E, F, G, H, I, K, L, M, N, Q, R, S, T, V, W)-R A or any amino acid (such as I, T, V, W)-M or any amino acid (such as A, E, K, L, P, Q, R, S, T, V, W)-D-Y (SEQ ID NO:30).

In aspects of the invention, the HCDR1 of the antibody molecule or antigen-binding portion may exclude the sequence GYTFTNYNMH (SEQ ID NO:33; 5F9G4 murine/humanized antibody HCDR1 disclosed in WO2011143624A2; US20130142786A1), the HCDR2 of the antibody molecule or antigen-binding portion may exclude the sequence MGTIYPGNDDTSYNQKFKD (SEQ ID NO:34; 5F9G4 murine/humanized antibody HCDR1 disclosed in WO2011143624A2; US20130142786A1), and/or the HCDR3 of the antibody molecule or antigen-binding portion may exclude the sequence GGYRAMDY (SEQ ID NO:35; 5F9G4 murine/humanized antibody HCDR3 disclosed in WO2011143624A2; US20130142786A1).

The antibody molecule or antigen-binding portion may further comprise a light chain variable region with:
   an LCDR1 having amino acids in sequence in the following order: R-S-S-Q-S-I or a conservative substitution of I (such as L)-V or a conservative substitution of V (such as L)-Y or a conservative substitution of Y (such as H)-S-N or any amino acid (such as G, S, K)-G or any amino acid (such as A, Y)-N or any amino acid (such as Q, Y)-T or any amino acid (such as N)-Y-L-G or any amino acid (such as D) (SEQ ID NO:36);
   an LCDR2 having amino acids in sequence in the following order: K-V or any amino acid (such as G)-S-N-R-F or any amino acid (such as A, S)-S(SEQ ID NO:37); and an LCDR3 having amino acids in sequence in the following order: F or any amino acid (such as L, M)-Q-G or any amino acid (such as A)-S or any amino acid (such as T, L, M)-H or any amino acid (such as Q, R)-V or any amino acid (such as I, T)-P-Y-T or any amino acid (such as I) (SEQ ID NO:38).

In aspects of the invention, the LCDR1 of the antibody molecule or antigen-binding portion may exclude the sequence RSSQSIVYSNGNTYLG (SEQ ID NO:39; 5F9G4 murine/humanized antibody LCDR1 disclosed in WO2011143624A2; US20130142786A1), and/or the LCDR2 of the antibody molecule or antigen-binding portion may exclude the sequence KVSNRFS (SEQ ID NO:40; 5F9G4 murine/humanized antibody LCDR2 disclosed in WO2011143624A2; US20130142786A1), and/or the LCDR3 of the antibody molecule or antigen binding portion may exclude the sequence FQGSHVPYT (SEQ ID NO:41).

In some aspects, disclosed herein is an anti-CD47 antibody or an antigen-binding portion thereof, wherein the antibody comprises a heavy chain variable (VH) region and a light chain variable (VL) region, wherein (a) the HCDR1 comprises the amino acid sequence G-Y-$X_1$-F-T-$X_2$-Y-$X_3$-$X_4$-$X_5$, wherein $X_1$ is S or a conservative substitution of S, $X_2$ is N or a conservative substitution of N (for example, S), $X_3$ is N or any other amino acid (for example, S, A), $X_4$ is M or a conservative substitution of M (for example, I) and $X_5$ is H or any other amino acid (for example, G) (SEQ ID NO:42);

(b) the HCDR2 comprises the amino acid sequence $X_1$-$X_2$-$X_3$-I-Y-P-G-$X_4$-$X_5$-$X_6$-T-$X_7$-Y-$X_8$-$X_9$-$X_{10}$-F-Q-G, wherein $X_1$ is M or a conservative substitution of M (for example, I), $X_2$ is G or a conservative substitution of G, $X_3$ is T or any other amino acid (for example, I), $X_4$ is N or any other amino acid (for example, D), $X_5$ is D or any other amino acid (for example, S), $X_6$ is D or any other amino acid, $X_7$ is S or any other amino acid (for example, R), $X_8$ is N or any other amino acid (for example, S), $X_9$ is Q or any other amino acid (for example, P) and $X_{10}$ is K or any other amino acid (for example, S) (SEQ ID NO:75);

(c) the HCDR3 comprises the amino acid sequence $X_1$-G-$X_2$-R-$X_3$-$X_4$-D-Y, wherein $X_1$ is G or any other amino acid (for example, Q), $X_2$ is Y or any other amino acid (for example, A, C, D, E, F, G, H, I, K, L, M, N, Q, R, S, T, V or W), $X_3$ is A or any other amino acid (for example, I, T, V or W) and $X_4$ is M or any other amino acid (for example, A, E, K, L, P, Q, R, S, T, V or W) (SEQ ID NO:44);

(d) the LCDR1 comprises the amino acid sequence R-S-S-Q-S-$X_1$-$X_2$-$X_3$-S-$X_4$-$X_5$-$X_6$-$X_7$-Y-L-$X_8$, wherein $X_1$ is I or a conservative substitution of I (for example, L), $X_2$ is V or a conservative substitution of V (for example, L), $X_3$ is Y or a conservative substitution of Y (for example, H), $X_4$ is N or any other amino acid (for example, G, S or K), $X_5$ is G or any other amino acid (for example, A or Y), $X_6$ is N or any other amino acid (for example, Q or Y), $X_7$ is T or any other amino acid (for example, N) and $X_8$ is G or any other amino acid (for example, D) (SEQ ID NO:45);

(e) the LCDR2 comprises the amino acid sequence K-$X_1$-S-N-R-$X_2$-S, wherein $X_1$ is V or any other amino acid (for example, G) and $X_2$ is F or any other amino acid (for example, A or S) (SEQ ID NO:46); and (f) the LCDR3 comprises the amino acid sequence $X_1$-Q-$X_2$-$X_3$-$X_4$-$X_5$-P-Y-$X_6$, wherein $X_1$ is F or any other amino acid (for example, L or M), $X_2$ is G or any other amino acid (for example, A), $X_3$ is S or any other amino acid (for example, T, L or M), $X_4$ is H or any other amino acid (for example, Q or R), $X_5$ is V or any other amino acid (for example, or T), $X_6$ is T or any other amino acid (for example, I) (SEQ ID NO:47).

In some aspects, disclosed herein is an anti-CD47 antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:42, the HCDR2 is SEQ ID NO:75, the HCDR3 is SEQ ID NO:44, the LCDR1 is SEQ ID NO:45, the LCDR2 is SEQ ID NO:46 and the LCDR3 is SEQ ID NO:47, wherein the heavy chain FR1, FR2, FR3 and FR4 amino acid sequences are the heavy chain FR1, FR2, FR3 and FR4 amino acid sequences in SEQ ID NO:141 (see Table 2) and wherein the light chain FR1, FR2, FR3 and FR4 amino acid sequences are the light chain FR1, FR2, FR3 and FR4 amino acid sequences in SEQ ID NO:144 (see Table 2).

As elaborated herein, the present inventors have succeeded for the first time in generating a number of optimized anti-CD47 antibody molecules using CDR sequences derived from the murine anti-CD47 antibody 5F9G4 disclosed in WO2011143624A2; US20130142786A1. In embodiments of the present invention, these antibody molecules have been selected to have binding specificity to both human CD47 as well as cynomolgus monkey CD47 (to facilitate in vivo studies in an appropriate animal test species). Further refining of the optimized antibody molecules as described herein has provided improved variable domain stability, higher expression yields, and/or reduced immunogenicity.

Preferred optimized anti-CD47 antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-CD47 binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to CD47. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-Y-T/S-F-T-N/S/D-Y-N/S/A-M/I-H/G (SEQ ID NO:76); the HCDR2 may have the amino acid sequence: M/I/N-G/A/S-T/I-I-Y-P-G-N/D-D/S-D/N-T-S/K/R-Y-N/S/H-Q/P/H-K/S-F-K/Q-D/G (SEQ ID NO:77); and the HCDR3 may have the amino acid sequence: G/Q-G-Y/A/C/D/E/F/G/H/I/K/L/M/N/Q/R/S/T/V/W-R-A/I/T/V/W-M/A/E/K/L/P/Q/R/S/T/V/W-D-Y (SEQ ID NO:78).

For example, the HCDR1 may have the amino acid sequence: G-Y-T/S-F-T-N/D-Y-N/A-M/I-H (SEQ ID NO:79); the HCDR2 may have the amino acid sequence: M-G-T-I-Y-P-G-N/D-D/S-D/N-T-S/K/R-Y-N/S-Q/P/H-K/S-F-Q-G (SEQ ID NO:80); and the HCDR3 may have the amino acid sequence: G-G-Y/E/F/I/K//N/V-R-A-M/E/Q-D-Y (SEQ ID NO:81).

In the antibody molecule or antigen-binding portion thereof, the LCDR1 may have the amino acid sequence: R-S-S-Q-S-L-V/L-Y/H-S-N/G/S/K-G/A/Y-N/Y-T/N-Y-L-G/D (SEQ ID NO:82); the LCDR2 may have the amino acid sequence: K-G-S-N-R-F/A-S (SEQ ID NO:83); and the LCDR3 may have the amino acid sequence: F/M-Q-G/A-S-H/Q-V-P-Y-T/I (SEQ ID NO:84).

For example, the LCDR1 may have the amino acid sequence: R-S-S-Q-S-L-L-H-S-N/K-G/A/Y-N/Q/Y-T/N-Y-L-G (SEQ ID NO:85); the LCDR2 may have the amino acid sequence: K-V/G-S-N-R-F/A/S-S (SEQ ID NO:86); and the LCDR3 may have the amino acid sequence: F/L/M-Q-G/A-S/T/L/M-H/Q/R-V/I/T-P-Y-T/I (SEQ ID NO:87).

In specific embodiments of the invention, the antibody molecule or antigen-binding portion may comprise:

(a) the amino acid sequences
GYTFTNYAMH, (SEQ ID NO: 48; HCDR1)

MGTIYPGNDDTKYNQKFQG, (SEQ ID NO: 49; HCDR2)

GGFRAMDY, (SEQ ID NO: 50; HCDR3)

RSSQSLLHSNGNTYLG, (SEQ ID NO: 51; LCDR1)

KGSNRFS, (SEQ ID NO: 52; LCDR2)

FQASHVPYT, (SEQ ID NO: 53; LCDR3)
[Clone VH1.8/VL1.1];
or (b) the amino acid sequences
GYTFTNYAMH, (SEQ ID NO: 48; HCDR1)

MGTIYPGNDDTKYNQKFQG, (SEQ ID NO: 49; HCDR2)

GGFRAMDY, (SEQ ID NO: 50; HCDR3)

RSSQSLLHSNGNTYLG, (SEQ ID NO: 51; LCDR1)

KGSNRFS, (SEQ ID NO: 52; LCDR2)

FQASQVPYT, (SEQ ID NO: 54; LCDR3)
[Clone VH1.8/VL1.2];
or (c) the amino acid sequences
GYTFTNYAMH, (SEQ ID NO: 48; HCDR1)

MGTIYPGNDDTKYNQKFQG, (SEQ ID NO: 49; HCDR2)

GGFRAMDY, (SEQ ID NO: 50; HCDR3)

RSSQSLLHSNANTYLG, (SEQ ID NO: 55; LCDR1)

KGSNRFS, (SEQ ID NO: 52; LCDR2)

FQASQVPYT, (SEQ ID NO: 54; LCDR3)
[Clone VH1.8/VL1.3];
or (d) the amino acid sequences
GYTFTNYAMH, (SEQ ID NO: 48; HCDR1)

MGTIYPGNDDTKYNQKFQG, (SEQ ID NO: 49; HCDR2)

GGFRAMDY, (SEQ ID NO: 50; HCDR3)

RSSQSLLHSNAYNYLG, (SEQ ID NO: 56; LCDR1)

KGSNRFS, (SEQ ID NO: 52; LCDR2)

FQASQVPYT, (SEQ ID NO: 54; LCDR3)
[Clone VH1.8/VL1.4];
or (e) the amino acid sequences
GYTFTNYAMH, (SEQ ID NO: 48; HCDR1)

MGTIYPGNDDTKYNQKFQG, (SEQ ID NO: 49; HCDR2)

GGFRAMDY, (SEQ ID NO: 50; HCDR3)

RSSQSLLHSNAYNYLG, (SEQ ID NO: 56; LCDR1)

KGSNRFS, (SEQ ID NO: 52; LCDR2)

FQASHVPYT, (SEQ ID NO: 53; LCDR3)
[Clone VH1.8/VL1.5];
or (f) the amino acid sequences
GYTFTNYAMH, (SEQ ID NO: 48; HCDR1)

MGTIYPGNDDTKYNQKFQG, (SEQ ID NO: 49; HCDR2)

GGFRAMDY, (SEQ ID NO: 50; HCDR3)

RSSQSLLHSNANTYLG, (SEQ ID NO: 55; LCDR1)

-continued (SEQ ID NO: 52; LCDR2)
KGSNRFS, (SEQ ID NO: 53; LCDR3)
FQASHVPYT,
[Clone VH1.8/VL1.6];
or (g) the amino acid sequences
(SEQ ID NO: 48; HCDR1)
GYTFTNYAMH, (SEQ ID NO: 49; HCDR2)
MGTIYPGNDDTKYNQKFQG, (SEQ ID NO: 59; HCDR3)
GGYRAEDY, (SEQ ID NO: 51; LCDR1)
RSSQSLLHSNGNTYLG, (SEQ ID NO: 52; LCDR2)
KGSNRFS, (SEQ ID NO: 53; LCDR3)
FQASHVPYT,
[Clone VH1.1/VL1.1];
or (h) the amino acid sequences
(SEQ ID NO: 48; HCDR1)
GYTFTNYAMH, (SEQ ID NO: 49; HCDR2)
MGTIYPGNDDTKYNQKFQG, (SEQ ID NO: 59; HCDR3)
GGYRAEDY, (SEQ ID NO: 51; LCDR1)
RSSQSLLHSNGNTYLG, (SEQ ID NO: 52; LCDR2)
KGSNRFS, (SEQ ID NO: 54; LCDR3)
FQASQVPYT,
[Clone VH1.1/VL1.2];
or (i) the amino acid sequences
(SEQ ID NO: 48; HCDR1)
GYTFTNYAMH, (SEQ ID NO: 49; HCDR2)
MGTIYPGNDDTKYNQKFQG, (SEQ ID NO: 59; HCDR3)
GGYRAEDY, (SEQ ID NO: 55; LCDR1)
RSSQSLLHSNANTYLG, (SEQ ID NO: 52; LCDR2)
KGSNRFS, (SEQ ID NO: 54; LCDR3)
FQASQVPYT,
[Clone VH1.1/VL1.3];
or (j) the amino acid sequences
(SEQ ID NO: 48; HCDR1)
GYTFTNYAMH, (SEQ ID NO: 49; HCDR2)
MGTIYPGNDDTKYNQKFQG, (SEQ ID NO: 59; HCDR3)
GGYRAEDY, -continued (SEQ ID NO: 55; LCDR1)
RSSQSLLHSNANTYLG, (SEQ ID NO: 52; LCDR2)
KGSNRFS, (SEQ ID NO: 53; LCDR3)
FQASHVPYT,
[Clone VH1.1/VL1.6];
or (k) the amino acid sequences
(SEQ ID NO: 88; HCDR1)
GYTFTDYNMH, (SEQ ID NO: 49; HCDR2)
MGTIYPGNDDTKYNQKFQG, (SEQ ID NO: 50; HCDR3)
GGFRAMDY, (SEQ ID NO: 51; LCDR1)
RSSQSLLHSNGNTYLG, (SEQ ID NO: 52; LCDR2)
KGSNRFS, (SEQ ID NO: 53; LCDR3)
FQASHVPYT,
[Clone VH1.5/VL1.1];
or (I) the amino acid sequences
(SEQ ID NO: 89; HCDR1)
GYTFTNYNIH, (SEQ ID NO: 90; HCDR2)
MGTIYPGNDDTSYSQKFQG, (SEQ ID NO: 50; HCDR3)
GGFRAMDY, (SEQ ID NO: 51; LCDR1)
RSSQSLLHSNGNTYLG, (SEQ ID NO: 52; LCDR2)
KGSNRFS, (SEQ ID NO: 53; LCDR3)
FQASHVPYT,
[Clone VH1.7/VL1.1];
or (m) the amino acid sequences
(SEQ ID NO: 89; HCDR1)
GYTFTNYNIH, (SEQ ID NO: 90; HCDR2)
MGTIYPGNDDTSYSQKFQG, (SEQ ID NO: 50; HCDR3)
GGFRAMDY, (SEQ ID NO: 51; LCDR1)
RSSQSLLHSNGNTYLG, (SEQ ID NO: 52; LCDR2)
KGSNRFS, (SEQ ID NO: 54; LCDR3)
FQASQVPYT,
[Clone VH1.7/VL1.2];
or (n) the amino acid sequences
(SEQ ID NO: 89; HCDR1)
GYTFTNYNIH, (SEQ ID NO: 90; HCDR2)
MGTIYPGNDDTSYSQKFQG, -continued

```
                      (SEQ ID NO: 50; HCDR3)
GGFRAMDY, (SEQ ID NO: 55; LCDR1)
RSSQSLLHSNANTYLG, (SEQ ID NO: 52; LCDR2)
KGSNRFS, (SEQ ID NO: 54; LCDR3)
FQASQVPYT,
[Clone VH1.7/VL1.3];
or (o) the amino acid sequences
                      (SEQ ID NO: 89; HCDR1)
GYTFTNYNIH, (SEQ ID NO: 90; HCDR2)
MGTIYPGNDDTSYSQKFQG, (SEQ ID NO: 50; HCDR3)
GGFRAMDY, (SEQ ID NO: 56; LCDR1)
RSSQSLLHSNAYNYLG, (SEQ ID NO: 52; LCDR2)
KGSNRFS, (SEQ ID NO: 53; LCDR3)
FQASHVPYT,
[Clone VH1.7/VL1.5];
or (p) the amino acid sequences
                      (SEQ ID NO: 89; HCDR1)
GYTFTNYNIH, (SEQ ID NO: 90; HCDR2)
MGTIYPGNDDTSYSQKFQG, (SEQ ID NO: 50; HCDR3)
GGFRAMDY, (SEQ ID NO: 55; LCDR1)
RSSQSLLHSNANTYLG, (SEQ ID NO: 52; LCDR2)
KGSNRFS, (SEQ ID NO: 53; LCDR3)
FQASHVPYT,
[Clone VH1.7/VL1.6];
or (q) the amino acid sequences
                      (SEQ ID NO: 48; HCDR1)
GYTFTNYAMH, (SEQ ID NO: 90; HCDR2)
MGTIYPGNDDTSYSQKFQG, (SEQ ID NO: 59; HCDR3)
GGYRAEDY, (SEQ ID NO: 51; LCDR1)
RSSQSLLHSNGNTYLG, (SEQ ID NO: 52; LCDR2)
KGSNRFS, (SEQ ID NO: 53; LCDR3)
FQASHVPYT,
[Clone VH1.6/VL1.1];
or (r) the amino acid sequences
                      (SEQ ID NO: 48; HCDR1)
GYTFTNYAMH, (SEQ ID NO: 90; HCDR2)
MGTIYPGNDDTSYSQKFQG, (SEQ ID NO: 59; HCDR3)
GGYRAEDY, (SEQ ID NO: 51; LCDR1)
RSSQSLLHSNGNTYLG, (SEQ ID NO: 52; LCDR2)
KGSNRFS, (SEQ ID NO: 54; LCDR3)
FQASQVPYT,
[Clone VH1.6/VL1.2];
or (s) the amino acid sequences
                      (SEQ ID NO: 48; HCDR1)
GYTFTNYAMH, (SEQ ID NO: 90; HCDR2)
MGTIYPGNDDTSYSQKFQG, (SEQ ID NO: 59; HCDR3)
GGYRAEDY, (SEQ ID NO: 51; LCDR1)
RSSQSLLHSNGNTYLG, (SEQ ID NO: 52; LCDR2)
KGSNRFS, (SEQ ID NO: 53; LCDR3)
FQASHVPYT,
[Clone VH1.9/VL1.1];
or (t) the amino acid sequences
                      (SEQ ID NO: 48; HCDR1)
GYTFTNYAMH, (SEQ ID NO: 91; HCDR2)
MGTIYPGNDDTKYSQKFQG, (SEQ ID NO: 59; HCDR3)
GGYRAEDY, (SEQ ID NO: 51; LCDR1)
RSSQSLLHSNGNTYLG, (SEQ ID NO: 52; LCDR2)
KGSNRFS, (SEQ ID NO: 54; LCDR3)
FQASQVPYT,
[Clone VH1.9/VL1.2];
or (u) the amino acid sequences
                      (SEQ ID NO: 57; HCDR1)
GYSFTNYNIH, (SEQ ID NO: 61; HCDR2)
MGTIYPGNSDTSYNPSFQG, (SEQ ID NO: 62; HCDR3)
GGVRAMDY, (SEQ ID NO: 51; LCDR1)
RSSQSLLHSNGNTYLG, (SEQ ID NO: 52; LCDR2)
KGSNRFS, (SEQ ID NO: 63; LCDR3)
MQASQVPYT,
[Clone D6];
or
```

-continued (v) the amino acid sequences
GYSFTNYNIH, (SEQ ID NO: 57; HCDR1)

MGTIYPGNSDTSYNPKFQG, (SEQ ID NO: 92; HCDR2)

GGKRAMDY, (SEQ ID NO: 93; HCDR3)

RSSQSLLHSNGNTYLG, (SEQ ID NO: 51; LCDR1)

KGSNRFS, (SEQ ID NO: 52; LCDR2)

MQASQVPYT, (SEQ ID NO: 63; LCDR3)
[Clone F-E5];
or (w) the amino acid sequences
GYSFTNYNIH, (SEQ ID NO: 57; HCDR1)

MGTIYPGDSDTSYNPKFQG, (SEQ ID NO: 94; HCDR2)

GGYRAQDY, (SEQ ID NO: 95; HCDR3)

RSSQSLLHSNGNTYLG, (SEQ ID NO: 51; LCDR1)

KGSNRFS, (SEQ ID NO: 52; LCDR2)

MQASHVPYT, (SEQ ID NO: 96; LCDR3)
[Clone E-C5];
or (x) the amino acid sequences
GYSFTNYNIH, (SEQ ID NO: 57; HCDR1)

MGTIYPGDSDTSYNPKFQG, (SEQ ID NO: 94; HCDR2)

GGYRAEDY, (SEQ ID NO: 59; HCDR3)

RSSQSLLHSNGNTYLG, (SEQ ID NO: 51; LCDR1)

KGSNRFS, (SEQ ID NO: 52; LCDR2)

MQGSHVPYT, (SEQ ID NO: 97; LCDR3)
[Clone E-D6];
or (y) the amino acid sequences
GYSFTNYNIH, (SEQ ID NO: 57; HCDR1)

MGTIYPGDSDTRYNQKFQG, (SEQ ID NO: 98; HCDR2)

GGIRAMDY, (SEQ ID NO: 99; HCDR3)

RSSQSLLHSNGNTYLG, (SEQ ID NO: 51; LCDR1)

KGSNRFS, (SEQ ID NO: 52; LCDR2)

FQGSHVPYI, (SEQ ID NO: 100; LCDR3)

[Clone B-A6];
or (z) the amino acid sequences
GYSFTNYNIH, (SEQ ID NO: 57; HCDR1)

MGTIYPGNSDTRYNPKFQG, (SEQ ID NO: 101; HCDR2)

GGFRAMDY, (SEQ ID NO: 50; HCDR3)

RSSQSLLHSNGNTYLG, (SEQ ID NO: 51; LCDR1)

KGSNRFS, (SEQ ID NO: 52; LCDR2)

MQGSHVPYT, (SEQ ID NO: 97; LCDR3)
[Clone D-C12];
or (zi) the amino acid sequences
GYSFTNYNIH, (SEQ ID NO: 57; HCDR1)

MGTIYPGDSDTRYNPKFQG, (SEQ ID NO: 58; HCDR2)

GGYRAEDY, (SEQ ID NO: 59; HCDR3)

RSSQSLLHSNGNTYLG, (SEQ ID NO: 51; LCDR1)

KGSNRFS, (SEQ ID NO: 52; LCDR2)

MQGSHVPYT, (SEQ ID NO: 97; LCDR3)
[Clone E-A1].

In some aspects, disclosed herein is an anti-CD47 antibody or an antigen-binding portion thereof, wherein the antibody comprises a heavy chain variable (VH) region and a light chain variable (VL) region, wherein (a) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASHVPYT (SEQ ID NO:53);

(b) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNGNTYLG (SEQ ID NO:51), LCDR2 of KGSNRFS (SEQ ID NO:52) and LCDR3 of FQASHVPYT (SEQ ID NO:53);

(c) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNAYNYLG (SEQ ID NO:56), LCDR2 of KGSNRFS (SEQ ID NO:52) and LCDR3 of FQASHVPYT (SEQ ID NO:53);

(d) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNAYNYLG (SEQ ID NO:56), LCDR2 of KGSNRFS (SEQ ID NO:52) and LCDR3 of FQASQVPYT (SEQ ID NO:54);

(e) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASQVPYT (SEQ ID NO:54);

(f) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNGNTYLG (SEQ ID NO:51), LCDR2 of KGSNRFS (SEQ ID NO:52) and LCDR3 of FQASQVPYT (SEQ ID NO:54);

(g) the VH region amino acid sequence comprises HCDR1 of GYSFTNYNIH (SEQ ID NO:57), HCDR2 of MGTIYPGNSDTSYNPSFQG (SEQ ID NO: 61) and HCDR3 of GGVRAMDY (SEQ ID NO:62); and the VL region amino acid sequence comprises LCDR1 of RSSQSLLHSNGNTYLG (SEQ ID NO:51), LCDR2 of KGSNRFS (SEQ ID NO:52) and LCDR3 of MQASQVPYT (SEQ ID NO:63); or (h) the VH region amino acid sequence comprises HCDR1 of GYSFTNYNIH (SEQ ID NO:57), HCDR2 of MGTIYPGDSDTRYNPKFQG (SEQ ID NO:58) and HCDR3 of GGYRAEDY (SEQ ID NO:59); and the VL region amino acid sequence comprises LCDR1 of RSSQSLLHSNGNTYLG (SEQ ID NO:51), LCDR2 of KGSNRFS (SEQ ID NO:52) and LCDR3 of MQGSHVPY (SEQ ID NO:60).

In some aspects, disclosed herein is anti-CD47 antibody or an antigen-binding portion thereof, wherein the antibody comprises a heavy chain variable (VH) region and a light chain variable (VL) region, wherein the VH region comprises any one of the VH region amino acid sequences in Table 7 and the VL region comprises any one of the VL region amino acid sequences in Table 7.

In some aspects, disclosed herein is an anti-CD47 antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6;

(d) the VH region amino acid sequence comprises SEQ ID NO:7 and the VL region amino acid sequence comprises SEQ ID NO:8;

(e) the VH region amino acid sequence comprises SEQ ID NO:9 and the VL region amino acid sequence comprises SEQ ID NO:10;

(f) the VH region amino acid sequence comprises SEQ ID NO:11 and the VL region amino acid sequence comprises SEQ ID NO:12;

(g) the VH region amino acid sequence comprises SEQ ID NO:13 and the VL region amino acid sequence comprises SEQ ID NO:14; or (h) the VH region amino acid sequence comprises SEQ ID NO:15 and the VL region amino acid sequence comprises SEQ ID NO:16.

In some aspects, disclosed herein is an anti-CD47 antibody or an antigen-binding portion thereof, wherein the antibody comprises a heavy chain variable (VH) region and a light chain variable (VL) region, wherein (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:1 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:2;

(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:3 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:4;

(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:5 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:6;

(d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:7 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:8;

(e) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:9 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:10;

(f) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:11 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:12;

(g) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:13 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:14; or (h) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:15 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:16.

In some aspects, the CDR amino acid sequences of an anti-CD47 antibody are 100% identical to the CDR amino acid sequences in the recited sequences while the FR amino acid sequences are less than 100% identical to the FR amino acid sequences in the recited sequences.

In some aspects, the antibody or antigen-binding portion as defined herein may be isolated.

The antibody molecule or antigen-binding portion as defined herein may cross-compete for binding to CD47 with an antibody or antigen-binding portion thereof comprising the sets of CDRs disclosed herein. In some embodiments, the invention provides an isolated anti-CD47 antibody or an antigen-binding portion thereof, wherein the antibody or antigen-binding portion cross-competes for binding to CD47 with the antibody or antigen-binding portion comprising the sets of CDRs disclosed herein; and (a) comprises fully germline human framework amino acid sequences; and/or (b) does not comprise an 'NG' high-risk deamidation site in the LCDR1; (c) does not comprise an 'NT' deamidation site in the LCDR1; and/or (d) comprises a human germline peptide sequence with high MHC class II binding affinity in HCDR1 and/or HCDR2; and/or (e) does not comprise a human T cell epitope sequence in the LCDR1; and/or (f) does not comprise a human T cell epitope sequence in the HCDR1 or in the HCDR1/Framework 2 region of the VH domain. In some embodiments, the human germline peptide sequence with high MHC class II binding affinity in the HCDR2 is FQGQVTISA (SEQ ID NO:102) or FQGRVTITA (SEQ ID NO:103).

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-CD47 antibodies of the invention to the target CD47 (e.g., human CD47). The extent to which an antibody or portion thereof is able to interfere with the binding of another to the target, and therefore whether it can be said to cross-block or cross-compete according to the invention, can be determined using competition binding assays. One example of a binding competition assay is an assay technology known under the trademark Homogeneous Time Resolved Fluorescence® (HTRF®). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the 5F9G4 murine LCDR1 (as defined herein, i.e. the amino acid sequence RSSQSIVYSNGNTYLG (SEQ ID NO:39)) has been identified to have a putative 'high-risk' deamidation motif at residues 10 and 11 (NG). Removal this site at equivalent positions in an LCDR1 of the invention, for example by substitution of residue 10 (such as to G, S or K), is envisaged (as for example in multiple clones in Table 3). Removal this site at equivalent positions in an LCDR1 of the invention, for example by substitution of residue 11 (such as to A or Y), is also envisaged (as for example in clones containing the VL1.4 v-domain sequence and multiple other clones found in Tables 3 and 4).

In a further example, the 5F9G4 murine LCDR1 (as defined herein, i.e. the amino acid sequence RSSQSIVYSNGNTYLG (SEQ ID NO:39)) has been identified to have a putative 'high-risk' deamidation motif at residues 12 and 13 (NT). Removal this risk site at equivalent positions in an LCDR1 of the invention, for example by substitution of residue 12 (such as to Q, Y), is envisaged (as for example in clones containing the VL1.4 v-domain sequence and multiple other clones found in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV5-51 human germline scaffold into which the corresponding HCDR sequences have been inserted. The antibody molecule or antigen-binding portion thereof may comprise a VH region that comprises an IGHV5-51 human germline scaffold amino acid sequence into which a set of corresponding HCDR1, HCDR2 and HCDR3 amino acid sequences have been inserted.

The antibody molecule or antigen-binding portion thereof may comprise an IGHV1-3 human germline scaffold into which the corresponding HCDR sequences have been inserted. The antibody molecule or antigen-binding portion thereof may comprise a VH region that comprises an IGHV1-3 human germline scaffold amino acid sequence into which a set of corresponding HCDR1, HCDR2 and HCDR3 amino acid sequences have been inserted.

The antibody molecule or antigen-binding portion thereof may comprise an IGKV2-28 human germline scaffold into which the corresponding LCDR sequences have been inserted. The antibody molecule or antigen-binding portion thereof may comprise a VL region that comprises an IGKV2-28 human germline scaffold amino acid sequence into which a set of corresponding LCDR1, LCDR2 and LCDR3 amino acid sequences have been inserted.

The antibody molecule or antigen-binding portion thereof may comprise an IGHV5-51 human germline scaffold into which the corresponding HCDR sequences have been inserted and an IGKV2-28 human germline scaffold into which the corresponding LCDR sequences have been inserted. The antibody molecule or antigen-binding portion thereof may comprise a VH region that comprises an IGHV5-51 human germline scaffold amino acid sequence into which a set of corresponding HCDR1, HCDR2 and HCDR3 amino acid sequences have been inserted and a VL region that comprises an IGKV2-28 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4. In some embodiments, all six CDR sequences are from the same clone in Table 4. In some embodiments, the HCDR1, HCDR2 and HCDR3 sequences are from a first clone in Table 4, and the LCDR1, LCDR2 and LCDR3 sequences are from a second clone in Table 4.

The antibody molecule or antigen-binding portion thereof may comprise an IGHV1-3 human germline scaffold into which the corresponding HCDR sequences have been inserted and an IGKV2-28 human germline scaffold into which the corresponding LCDR sequences have been inserted. The antibody molecule or antigen-binding portion thereof may comprise a VH region that comprises an IGHV1-3 human germline scaffold amino acid sequence into which a set of corresponding HCDR1, HCDR2 and HCDR3 amino acid sequences have been inserted and a VL region that comprises an IGKV2-28 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4. In some embodiments, all six CDR sequences are from the same clone in Table 4. In some embodiments, the HCDR1, HCDR2 and HCDR3 sequences are from a first clone in Table 4, and the LCDR1, LCDR2 and LCDR3 sequences are from a second clone in Table 4.

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG1null, IgG4(S228P), IgA1 or IgA2. The antibody molecule or antigen-binding portion thereof may comprise an immunologically inert constant region. In some aspects, an anti-CD47 antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-CD47 antibody or antigen-binding portion thereof may comprise an immunoglobulin constant region comprising a wild-type human IgG2 constant region or a wild-type human IgG4 constant region. In some aspects, an anti-CD47 antibody may comprise an immunoglobulin constant region comprising any one of the amino acid sequences in Table 8. The Fc region sequences in Table 8 begin at the CH1 domain. In some aspects, an anti-CD47 antibody may comprise an immunoglobulin constant region comprising an amino acid sequence of an Fc region of human IgG4, human IgG4(S228P), human IgG2, human IgG1, human IgG1-3M or human IgG1-4M. For example, the human IgG4(S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 Therap. Immunol. 2:77-94). In some aspects, an immunoglobulin constant region may comprise an RDELT (SEQ ID NO:26) motif or an REEM (SEQ ID NO:27) motif (underlined in Table 8). The REEM (SEQ ID NO:27) allotype is found in a smaller human population than the RDELT (SEQ ID NO:26) allotype. In some aspects, an anti-CD47 antibody may comprise an immunoglobulin constant region comprising any one of SEQ ID NOS:17-23. In some aspects, an anti-CD47 antibody may comprise the six CDR amino acid sequences of any one of the clones in Table 4 and any one of the Fc region amino acid sequences in Table 8. In some aspects, an anti-CD47 antibody may comprise an immunoglobulin heavy chain constant region comprising any one of the Fc region amino acid sequences in Table 8 and an immunoglobulin light chain constant region that is a kappa light chain constant region or a lambda light chain constant region.

In some aspects, disclosed herein is an anti-CD47 antibody or an antigen-binding portion thereof, wherein the antibody comprises a heavy chain variable (VH) region, a light chain variable (VL) region and a heavy chain constant region, wherein
(a) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); the VL region amino acid sequence comprises LCDR1 of RSSQSLLHSNANTYLG (SEQ ID NO:55), LCDR2 of KGSNRFS (SEQ ID NO:52) and LCDR3 of FQASHVPYT (SEQ ID NO:53); and the heavy chain constant region comprises any one of SEQ ID NOS: 17-23;
(b) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); the VL region amino acid sequence comprises LCDR1 of RSSQSLLHSNGNTYLG (SEQ ID NO:51), LCDR2 of KGSNRFS (SEQ ID NO:52) and LCDR3 of FQASHVPYT (SEQ ID NO:53); and the heavy chain constant region comprises any one of SEQ ID NOS: 17-23;
(c) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); the VL region amino acid sequence comprises LCDR1 of RSSQSLLHSNAYNYLG (SEQ ID NO:56), LCDR2 of KGSNRFS (SEQ ID NO:52) and LCDR3 of FQASHVPYT (SEQ ID NO:53); and the heavy chain constant region comprises any one of SEQ ID NOS: 17-23;
(d) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); the VL region amino acid sequence comprises LCDR1 of RSSQSLLHSNAYNYLG (SEQ ID NO:56), LCDR2 of KGSNRFS (SEQ ID NO:52) and LCDR3 of FQASQVPYT (SEQ ID NO:54); and the heavy chain constant region comprises any one of SEQ ID NOS: 17-23;
(e) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); the VL region amino acid sequence comprises LCDR1 of RSSQSLLHSNANTYLG (SEQ ID NO:55), LCDR2 of KGSNRFS (SEQ ID NO:52) and LCDR3 of FQASQVPYT (SEQ ID NO:54); and the heavy chain constant region comprises any one of SEQ ID NOS: 17-23;
(f) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); the VL region amino acid sequence comprises LCDR1 of RSSQSLLHSNGNTYLG (SEQ ID NO:51), LCDR2 of KGSNRFS (SEQ ID NO:52) and LCDR3 of FQASQVPYT (SEQ ID NO:54); and the heavy chain constant region comprises any one of SEQ ID NOS: 17-23;
(g) the VH region amino acid sequence comprises HCDR1 of GYSFTNYNIH (SEQ ID NO:57), HCDR2 of MGTIYPGNSDTSYNPSFQG (SEQ ID NO: 61) and HCDR3 of GGVRAMDY (SEQ ID NO:62); the VL region amino acid sequence comprises LCDR1 of RSSQSLLHSNGNTYLG (SEQ ID NO:51), LCDR2 of KGSNRFS (SEQ ID NO:52) and LCDR3 of MQASQVPYT (SEQ ID NO:63); and the heavy chain constant region comprises any one of SEQ ID NOS: 17-23; or
(h) the VH region amino acid sequence comprises HCDR1 of GYSFTNYNIH (SEQ ID NO:57), HCDR2 of MGTIYPGDSDTRYNPKFQG (SEQ ID NO:58) and HCDR3 of GGYRAEDY (SEQ ID NO:59); the VL region amino acid sequence comprises LCDR1 of RSSQSLLHSNGNTYLG (SEQ ID NO:51), LCDR2 of KGSNRFS (SEQ ID NO:52) and LCDR3 of MQGSHVPY (SEQ ID NO:60); and the heavy chain constant region comprises any one of SEQ ID NOS: 17-23.

In some aspects, disclosed herein is an anti-CD47 antibody or an antigen-binding portion thereof, wherein the antibody comprises a heavy chain variable (VH) region, a light chain variable (VL) region and a heavy chain constant region, wherein
a) the VH region amino acid sequence comprises or consists of SEQ ID NO:1; the VL region amino acid sequence comprises or consists of SEQ ID NO:2; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(b) the VH region amino acid sequence comprises or consists of SEQ ID NO:3; the VL region amino acid sequence comprises or consists of SEQ ID NO:4; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(c) the VH region amino acid sequence comprises or consists of SEQ ID NO:5; the VL region amino acid sequence comprises or consists of SEQ ID NO:6; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(d) the VH region amino acid sequence comprises or consists of SEQ ID NO:7; the VL region amino acid sequence comprises or consists of SEQ ID NO:8; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(e) the VH region amino acid sequence comprises or consists of SEQ ID NO:9; the VL region amino acid sequence comprises or consists of SEQ ID NO:10; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(f) the VH region amino acid sequence comprises or consists of SEQ ID NO:11; the VL region amino acid sequence comprises or consists of SEQ ID NO:12; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(g) the VH region amino acid sequence comprises or consists of SEQ ID NO:13; the VL region amino acid sequence comprises or consists of SEQ ID NO:14; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A; or (h) the VH region amino acid sequence comprises or consists of SEQ ID NO:15; the VL region amino acid sequence comprises or consists of SEQ ID NO:16; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A.

In some aspects, disclosed herein is an anti-CD47 antibody or an antigen-binding portion thereof, wherein the antibody comprises a heavy chain variable (VH) region, a light chain variable (VL) region and a heavy chain constant region, wherein a) the VH region amino acid sequence comprises or consists of SEQ ID NO:1; the VL region amino acid sequence comprises or consists of SEQ ID NO:2; and the heavy chain constant region comprises any one of SEQ ID NOS: 17-23;

(b) the VH region amino acid sequence comprises or consists of SEQ ID NO:3; the VL region amino acid sequence comprises or consists of SEQ ID NO:4; and the heavy chain constant region comprises any one of SEQ ID NOS: 17-23;

(c) the VH region amino acid sequence comprises or consists of SEQ ID NO:5; the VL region amino acid sequence comprises or consists of SEQ ID NO:6; and the heavy chain constant region comprises any one of SEQ ID NOS: 17-23;

(d) the VH region amino acid sequence comprises or consists of SEQ ID NO:7; the VL region amino acid sequence comprises or consists of SEQ ID NO:8; and the heavy chain constant region comprises any one of SEQ ID NOS: 17-23;

(e) the VH region amino acid sequence comprises or consists of SEQ ID NO:9; the VL region amino acid sequence comprises or consists of SEQ ID NO:10; and the heavy chain constant region comprises any one of SEQ ID NOS: 17-23;

(f) the VH region amino acid sequence comprises or consists of SEQ ID NO:11; the VL region amino acid sequence comprises or consists of SEQ ID NO:12; and the heavy chain constant region comprises any one of SEQ ID NOS: 17-23;

(g) the VH region amino acid sequence comprises or consists of SEQ ID NO:13; the VL region amino acid sequence comprises or consists of SEQ ID NO:14; and the heavy chain constant region comprises any one of SEQ ID NOS: 17-23; or (h) the VH region amino acid sequence comprises or consists of SEQ ID NO:15; the VL region amino acid sequence comprises or consists of SEQ ID NO:16; and the heavy chain constant region comprises any one of SEQ ID NOS: 17-23.

In some aspects, an anti-CD47 antibody may be immune effector null. In some aspects, an anti-CD47 antibody or an antigen-binding portion thereof does not induce immune effector function and, optionally, suppresses immune effector function. In some aspects, an anti-CD47 may lack measurable binding to human FcγRI, FcγRIIa, FcγRIIIa and FcγRIIIb receptors but maintain binding to human FcγRIIb receptor and optionally maintain binding to human FcRn receptor. FcγRI, FcγRIIa, FcγRIIIa and FcγRIIIb are examples of activating receptors. FcγRIIb is an example of an inhibitory receptor. FcRn is an example of a recycling receptor. In some aspects, binding affinity of an anti-CD47 antibody or an antigen-binding portion thereof for human Fc receptors may be measured by a biosensor system sold under the trademark Biacore® analysis. In some aspects, assay technology known under the trademark Homogeneous Time Resolved Fluorescence (HTRF®) can be used to study binding of an anti-CD47 antibody to human Fc receptors. In one example of the assay technology known under the trademark HTRF®, human IgG1 (wild type) is labelled, as is the full suite of Fc gamma receptors and then antibodies with engineered Fc fragments are used in titration competition. In some aspects, CD47-positive cells may be mixed with human white blood cells and anti-CD47 antibodies, and cell killing by CDC, ADCC and/or ADCP may be measured. In some aspects, an anti-CD47 antibody comprising an amino acid sequence of an Fc region of human IgG1-3M (see Table 8) is effector null. In some aspects, an anti-CD47 antibody comprising an amino acid sequence of an Fc region of human IgG1-3M (see Table 8) is not effector null.

The antibody molecule or antigen-binding portion thereof may be a Fab fragment, a F(ab)$_2$ fragment, an Fv fragment, an scFv (single-chain Fv) fragment, a tetrameric antibody, a tetravalent antibody, a multispecific antibody (for example, a bispecific antibody), a domain-specific antibody, a single domain antibody, a monoclonal antibody or a fusion protein. In one embodiment, an antibody may be a bispecific antibody that binds specifically to a first antigen and a second antigen, wherein the first antigen is CD47 and the second antigen is not CD47. Antibody molecules and methods for their construction and use are described, in for example Holliger & Hudson (2005, Nature Biotechnol. 23(9): 1126-1136).

In some aspects, the invention provides a heavy chain variable (VH) region sequence and a light chain variable (VL) region sequence that neutralizes the CD47-SIRPα interaction more potently in the single-chain Fv (scFv) format than in the IgG format. In some embodiments, the VH regions of such molecules are in the IGHV5-51 framework. In some embodiments, the invention encompasses a single-chain Fv (scFv) comprising a heavy chain variable (VH) region and a light chain variable (VL) region, wherein (a) the HCDR1 comprises G-Y-T-F-T-$X_1$-Y-$X_2$-$X_3$-$X_4$, wherein $X_1$ is N or a conservative substitution of N, $X_2$ is N or any other amino acid, $X_3$ is M or a conservative substitution of M and $X_4$ is H or any other amino acid (SEQ ID NO:104); (b) the HCDR2 comprises M-G-$X_1$-I-Y-P-G-$X_2$-$X_3$-$X_4$-T-$X_5$-Y-$X_6$-$X_7$-$X_8$-F-Q-G, wherein $X_1$ is T or any other amino acid, $X_2$ is N or a conservative substitution of N, $X_3$ is D or any other amino acid, $X_4$ is D or any other amino acid, $X_5$ is S or any other amino acid, $X_6$ is N or any other amino acid, $X_7$ is Q or any other amino acid and $X_8$ is K or any other amino acid (SEQ ID NO:105); (c) the HCDR3 comprises; $X_1$-G-$X_2$-R-$X_3$-$X_4$-D-Y, wherein $X_1$ is G or any other amino acid, $X_2$ is Y or any other amino acid, $X_3$ is A or any other amino acid and $X_4$ is M or any other amino acid (SEQ ID NO:44) (d) the LCDR1 comprises R-S-S-Q-S-$X_1$-$X_2$-$X_3$-S-$X_4$-$X_5$-$X_6$-$X_7$-Y-L-$X_8$, wherein $X_1$ is I or a conservative substitution of I, $X_2$ is V or a conservative substitution of V, $X_3$ is Y or a conservative substitution of Y, $X_4$ is N or any other amino acid, $X_5$ is G or any other amino acid, $X_6$ is N or any other amino acid, $X_7$ is T or any other amino acid and $X_8$ is G or any other amino acid (SEQ ID NO:45); (e) the LCDR2 comprises K-$X_1$-S-N-R-$X_2$-S, wherein $X_1$ is V or any other amino acid and $X_2$ is F or any other amino acid (SEQ ID NO:46); and (D the LCDR3 comprises $X_1$-Q-$X_2$-$X_3$-$X_4$-$X_5$-P-Y-$X_6$, wherein $X_1$ is F or any other amino acid, $X_2$ is G or any other amino acid, $X_3$ is S or any other amino acid, $X_4$ is H or any other amino acid, $X_5$ is V or any other amino acid, $X_6$ is T or any other amino acid (SEQ ID NO:47); and wherein the VH region comprises an IGHV5-51 human germline scaffold amino acid sequence into which the HCDR1, HCDR2 and HCDR3 amino acid sequences have been inserted. In one embodiment, an scFv of the invention may comprise (a) the VH amino acid sequence comprises the HCDR1 of GYSFTNYNIH (SEQ ID NO:57), the HCDR2 of MGTIYPGDSDTSYNPKFQG (SEQ ID NO:94) and the HCDR3 of GGYRAEDY (SEQ ID NO:59); and (b) the VH amino acid sequence comprises the LCDR1 of RSSQSLLHSNGNTYLG (SEQ ID NO:51), the LCDR2 of KGSNRFS (SEQ ID NO:52) and the LCDR3 of MQGSHVPYT (SEQ ID NO:97). In some aspects, an scFv comprises, in amino-terminal to carboxyl-terminal order, VH-VL or VL-VH. In some aspects, an scFv comprises a linker between the VH sequence and the VL sequence. In some embodiments, an scFv further comprises an immunoglobulin constant region or a portion of an immunoglobulin constant region. In some embodiments, the invention provides a multispecific (e.g., bispecific) CD47-binding molecule comprising one or more scFv disclosed herein. In some cases, the immunoglobulin constant region comprises any one of SEQ ID NOS:17-23.

In another aspect of the invention, there is provided an immunoconjugate comprising the antibody molecule or antigen-binding portion thereof of the invention as defined herein linked to a therapeutic agent.

Examples of suitable therapeutic agents include cytotoxins, radioisotopes, chemotherapeutic agents, immunomodulatory agents, anti-angiogenic agents, anti proliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the anti-folates, *vinca* alkaloids, and the anthracyclines. Plant toxins, other bioactive proteins, enzymes (i.e., Antibody-Directed Enzyme Prodrug Therapy (ADEPT)), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, down-regulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-CD47 antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-CD47 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

For example, the cancer may be Gastrointestinal Stromal cancer (GIST), pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

For example, the autoimmune disease or inflammatory disease may be arthritis, asthma, multiple sclerosis, psoriasis, Crohn's disease, inflammatory bowel disease, lupus, Grave's disease and Hashimoto's thyroiditis, or ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of a cardiovascular disease or a fibrotic disease.

The cardiovascular disease in any aspect of the invention may for example be coronary heart disease or atherosclerosis.

For example, the fibrotic disease in any aspect of the invention may be myocardial infarction, angina, osteoarthritis, pulmonary fibrosis, asthma, cystic fibrosis or bronchitis.

In one embodiment, the invention provides an anti-CD47 antibody or an antigen-binding portion thereof comprising the amino acid sequences disclosed herein for use in therapy.

The pharmaceutical composition of the invention may comprise a pharmaceutically acceptable excipient, carrier or diluent. A pharmaceutically acceptable excipient may be a compound or a combination of compounds entering into a pharmaceutical composition which does not provoke secondary reactions and which allows, for example, facilitation of the administration of the anti-CD47 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-CD47 antibody molecule.

In some embodiments, the anti-CD47 antibody molecule may be provided in a lyophilised form for reconstitution prior to administration. For example, lyophilised antibody molecules may be re-constituted in sterile water and mixed with saline prior to administration to an individual.

The anti-CD47 antibody molecules will usually be administered in the form of a pharmaceutical composition, which may comprise at least one component in addition to the antibody molecule. Thus pharmaceutical compositions may comprise, in addition to the anti-CD47 antibody molecule, a pharmaceutically acceptable excipient, carrier, buffer, stabilizer or other materials well known to those skilled in the art. Such materials should be non-toxic and should not interfere with the efficacy of the anti-CD47 antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-CD47 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non ionic surfactants, such as a non-ionic surfactant sold under the trademark TWEEN™, a non ionic surfactant sold under the trademark PLURONICS™ or polyethylene glycol (PEG).

A pharmaceutical composition comprising an anti-CD47 antibody molecule may be administered alone or in combination with other treatments, either simultaneously or sequentially dependent upon the condition to be treated.

An anti-CD47 antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-CD47 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-CD47 antibody molecules as described herein may be administered as sub-cutaneous injections. Sub-cutaneous injections may be administered using an auto-injector, for example for long or short-term prophylaxis/treatment.

In some preferred embodiments, the therapeutic effect of the anti-CD47 antibody molecule may persist for several multiples of the antibody half-life in serum, depending on the dose. For example, the therapeutic effect of a single dose of the anti-CD47 antibody molecule may persist in an individual for 1 month or more, 2 months or more, 3 months or more, 4 months or more, 5 months or more, or 6 months or more.

The invention also provides a method of producing an antibody molecule which specifically binds to human CD47 and optionally also to cynomolgus monkey CD47 or an antigen-binding portion thereof, comprising the steps of:
(1) grafting anti-CD47 CDRs from a non-human source into a human v-domain framework to produce a humanized anti-CD47 antibody molecule or antigen-binding portion thereof;
(2) generating a phage library of clones of the humanized anti-CD47 antibody molecule or antigen-binding portion thereof comprising one or more mutations in the CDRs;
(3) selecting the phage library for binding to human CD47 and optionally also to cynomolgus monkey CD47;
(4) screening clones from the selection step (3) having binding specificity to human CD47 and optionally also to cynomolgus monkey CD47; and
(5) producing an antibody molecule which specifically binds to human CD47 and optionally also to cynomolgus monkey CD47, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "CD47" refers to IAP (Integrin Associated Protein) and variants thereof that retain at least part of the biological activity of CD47. As used herein, CD47 includes all mammalian species of native sequence CD47, including human, rat, mouse and chicken. The term "CD47" is used to include variants, isoforms and species homologs of human CD47. Antibodies of the invention may cross-react with CD47 from species other than human, in particular CD47 from cynomolgus monkey (*Macaca fascicularis*). Examples of human and cynomolgus CD47 amino acid sequences are provided in Table 9. In certain embodiments, the antibodies may be completely specific for human CD47 and may not exhibit non-human cross-reactivity.

As used herein, an "antagonist" as used in the context of the antibody of the invention or an "anti-CD47 antagonist antibody" (interchangeably termed "anti-CD47 antibody") refers to an antibody which is able to bind to CD47 and inhibit CD47 biological activity and/or downstream pathway(s) mediated by CD47 signalling. An anti-CD47 antagonist antibody encompasses antibodies that can block, antagonize, suppress or reduce (including significantly) CD47 biological activity, including downstream pathways mediated by CD47 signalling, such as receptor binding and/or elicitation of a cellular response to CD47. For the purposes of the present invention, it will be explicitly understood that the term "anti-CD47 antagonist antibody" encompass all the terms, titles, and functional states and characteristics whereby CD47 itself, and CD47 biological activity (including but not limited to its ability to enhance the activation of phagocytosis by cells of the myeloid lineage), or the consequences of the activity or biological activity, are substantially nullified, decreased, or neutralized in any meaningful degree.

The antibody "specifically binds" "specifically interacts", "preferentially binds", "binds" or "interacts" with CD47 if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to CD47. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, and contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the 5F9G4 murine anti-CD47 antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | -1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding sub-sequences of antibodies) that contain minimal sequence derived from non human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody" or "fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to CD47, which is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a biosensor system sold under the trademark Biacore®.

The term "potency" is a measurement of biological activity and may be designated as $IC_{50}$, or effective concentration of an antibody or antibody drug conjugate to the antigen CD47 to inhibit 50% of activity measured in a CD47 activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to CD47.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neoadjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-CD47 Therapeutic Antibodies

Introduction

In this example, we successfully generate a panel of antagonistic, optimized anti-CD47 antibodies. These anti-CD47 antibodies are well expressed, biophysically stable, highly soluble and of maximized amino acid sequence identity to preferred human germlines.

Materials and Methods

IgG Cloning, Transient Expression, Purification

Antibody v-domain encoding DNA sequences were cloned via restriction-ligation cloning into separate IgG heavy and light-chain expression cassettes in separate plasmid vectors. Antibodies were expressed in two human IgG1 formats: IgG4(S228P) and IgG1null—IgG1 with the lower hinge mutations L234A/L235A/G237A, which minimise Fcγ receptor-driven effector functions. IgGs were expressed in HEK-293expi or CHO cells after transient transfection with endotoxin-free IgG expression plasmid preparations, per manufacturer's protocols. IgGs were purified using a single-step protocol: Conditioned media were loaded (neat) onto a 1 ml ProA sepharose column, pre-equilibrated in PBS pH7.4. The column was washed with 5 column volumes of PBS pH7.4, before the protein was eluted with 100 mM glycine, pH 2.7 and subjected to dialysis in PBS pH 7.4 using 30 kDa cutoff dialysis membrane.

IgG Titration Binding ELISAs

To coat ELISA plates sold under the name Greiner Bio-One High Binding ELISA plates, target proteins were diluted to 1 μg/ml in carbonate buffer and added at 100 μl per well, at 4° C., o/n. Coated plates were washed 3× with PBS pH7.4, blocked with 1% BSA in PBS (380 μl/well) for 1 hr at RT, then washed 3× with PBS-non-ionic surfactant sold under the trademark Tween® 20 (PBST). CD47 antibodies (100 μl/well; diluted in PBST) were then added and then incubated 1 hr at RT. Plates were then washed 3× with PBST and goat anti-human kappa chain-HRP added (100 μl/well) at RT, for 1 hr. Plates were then washed 3× with PBST and twice with PBS before the addition of 100 μl TMB per well. Reactions were stopped by adding 100 μl 2M $H_2SO_4$/well and OD was read on a plate reader at 450 nm.

Anti-CD47 antibodies were tested for polyreactivity by ELISA. Purified, recombinant, target and non-target antigens were coated in 96-well Nunc maxisorp plates at 100 ng per well in carbonate buffer, at 4° C. overnight. Plates were then washed 3x with PBS, blocked with 1% BSA in PBS, then washed 3x with PBS-non-ionic surfactant sold under the trademark Tween®20. A dilution series of primary antibodies was then applied, plates were washed 3x with PBS-Tween20 followed by application of goat anti-human kappa chain-HRP 1:4,000 secondary antibody. Wells were then washed 3x with PBS-non-ionic surfactant sold under the trademark Tween®20 and 2x with PBS, 100 µl TMB peroxidase substrate was added per well, the reaction was stopped by adding 100 µl 2M $H_2SO_4$ and absorbances were read at 450 nm. IgG binding analysis via ELISA on negatively charged biomolecular surfaces were performed as previously described (see Mouquet et al., 2010, Nature 467: 591-595).

CD47 Library Generation and Selection

The CD47 scFv repertoire was assembled by mass oligonucleotide synthesis and PCR. The amplified scFv repertoire was then cloned via restriction-ligation into a phagemid vector, transformed into E. coli TG-1 cells, and the phage repertoire rescued essentially as previously described in detail (Finlay et al., 2011, Methods Mol Biol 681: 383-401).

Phage selections were performed by coating streptavidin magnetic microbeads with CD47-Fc protein (either human or cyno), washing the beads thrice with PBS and resuspending in PBS pH7.4 plus 5% skim milk protein (MPBS). These beads were coated at 200 nM target protein in round 1 of selection, followed by 100, 50 and 10 nM in subsequent rounds.

Assay Technology Known Under the Trademark HTRF® Binding Competition Assay

A competition assay technology known under the trademark HTRF® was established to examine epitope competition against h5F9G4 IgG binding to human and/or cyno CD47-Fc by grafted and library-derived clones. The purified h5F9G4 IgG1 was labelled with terbium using a labelling kit sold under the name CisBio per the manufacturer's instructions. The final reaction mix contained biotinylated human or cyno CD47-Fc, SA-XL665 sold under the name CisBio, terbium-labelled parental h5F9G4 and competitor scFv or IgG of interest, prepared as described above, in a total reaction volume of 20 µl in 1x assay buffer [50 mM sodium phosphate, pH 7.5, 400 mM potassium fluoride, and 0.1% BSA (w/v)]. Reagents were added sequentially into 384-well low-volume black plates sold under the name Nunc. Reactions proceeded for 1 h at room temperature, and plates were subsequently read on a plate reader with excitation at 340 nm and two emission readings at 615 nm (measuring input donor fluorescence from h5F9G4-terbium) and 665 nm (measuring output acceptor fluorescence from SAXL665). Readings were expressed as 665 nm/615 nm ratios.

CD47-SIRPα Binding Competition Assay

A competition ELISA assay was established to examine the capacity of optimized leads to block the binding interaction of CD47 with SIRPα. To coat ELISA plates sold under the name Greiner Bio-One High Binding ELISA plates, 10 µg/ml human SIRPα-Fc in carbonate coating buffer was added at 100 µl per well, at 4° C., o/n. Coated plates were washed 3x with PBS pH7.4, blocked with 1% BSA in PBS (380 µl/well) for 1 hr at RT, then washed 3x with PBS-non-ionic surfactant sold under the trademark Tween®20 (PBST). Biotinylated human, mouse or cyno CD47-Fc was then added at 0.2 µg/ml in PBS, 100 µl per well, at room temperature for 60 minutes with or without the addition of competing scFv or IgGs. Plates were then washed 3x with PBST and Streptavidin-HRP added (100 µl/well) at room temperature, for 1 hr. Plates were then washed 3x with PBST and twice with PBS before the addition of 100 µl TMB per well. Reactions were stopped by adding 100 µl 2M $H_2SO_4$/well and OD was read on a plate reader at 450 nm.

Antibody v-Domain T Cell Epitope Content: In Silico Analyses

In silico technologies by the company known as Abzena, Ltd., which are based on identifying the location of T cell epitopes in therapeutic antibodies and proteins, were used for assessing potential immunogenicity in antibody v-domains. Immunogenicity assessment tool known under the trademark iTope™ was used to analyse the VL and VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The immunogenicity assessment tool known under the trademark iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using a database known under the trademark TCED™ (T Cell Epitope Database™) search for matches to T cell epitopes previously identified by in vitro human T cell epitope mapping analyses of other protein sequences. The database known under the trademark TCED™ is used to search any test sequence against a large (>10,000 peptides) database of peptides derived from unrelated protein and antibody sequences.

Phagocytosis Potency Assays Using Human Macrophages

Peripheral blood mononuclear cells (PBMCs) were isolated from whole blood by density gradient centrifugation. CD14 positive PBMCs were subsequently isolated via magnetic cell isolation using CD14 microbeads. In parallel, Jurkat cells were labelled using a green CFSE (carboxyfluorescein diacetate, succinimidyl ester) cell tracer dye. A total of $6.25 \times 10^5$ labelled Jurkat cells were pre incubated in the presence of UH2 antibodies in 96 well plates for 1 hour at 37 degrees C. in a humidified atmosphere containing 5% $CO_2$. Following incubation, $2.5 \times 10^5$ CD14 positive cells were added to each well and incubated for a further hour under the same culture conditions.

Cells were harvested by vigorous pipetting, stained with viability dye, fixed using ice-cold 4% paraformaldehyde for 10 minutes. Following fixation, cells were blocked with an Fc receptor binding inhibitor monoclonal antibody for 10 minutes and then incubated with a red fluorescent dye sold under the trademark Alexa Fluor® 647 (AF647) conjugated anti-human CD11b antibody at room temperature for 30 minutes and fixed a further time in 4% paraformaldehyde for 5 minutes.

Cells were analysed on a flow cytometer sold under the trademark BD LSRFortessa™ recording side scatter and forward scatter properties along with CFSE and AF647 fluorescence intensity data. Data was captured until at least $1 \times 10^4$ AF647 positive events were recorded. Data were analysed post-acquisition using software known under the trademark FlowJo™ (version 10.4.2). Briefly, cell debris was gated out by scatter properties (SSC-Area by FSC-Area). Single cells were also gated for by SSC-Area by SSC-Height and then by FSC-Area by FSC-Height. From the remaining single cell population, CFSE and CD11b double positives cells were gated using a quadrant gate placed based on the population of CD11b positive cells in the vehicle treated test. The percentage of CFSE positive cells from the CD11 b positive population was calculated and plotted.

RESULTS AND DISCUSSION

CDR Grafting onto Preferred Human Germline v-Genes

The CDRs of an antagonistic murine anti-CD47 IgG 5F9G4 (5F9G4; see WO2011143624A2 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV5-51 and IGKV2-28, which are known to be very well displayed and expressed in scFv format in phage display, have good solubility, high physical stability and are used at high frequency in the expressed human antibody repertoire. IGHV5-51 was also the preferred germline framework for grafting of the VH as it showed high sequence and structural motif homology with the m5F9G4 HCDR2 (FIG. 2).

Those scaffolds and grafted CDR definitions are outlined in Table 2. The heavy and light chain sequences for chimeric anti-CD47 antibody m5F9G4 and humanized h5F9G4 are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGKV2-28/IGHV5-51 graft was therefore taken forward as the template for CDR mutagenesis and selection of improved clones.

Library Generation and Screening

The CDR-grafted IGKV2-28/IGHV5-51 v-domain sequences were combined into a VL-VH scFv format and a mutagenesis library cassette was generated by mass oligonucleotide synthesis and assembly. The final scFv library was ligated into a phage display vector and transformed into E. coli via electroporation to generate $6.0 \times 10^8$ independent clones. Library build quality was verified by sequencing 96 clones. This sequencing data showed that the positions encoding either the murine or human germline residue at each position of variance had been effectively sampled at a frequency of approximately 50%. Libraries were rescued using helper phage M13 and selections performed on biotinylated human and cynomolgus monkey CD47-Fc proteins in multiple separate branches.

Post-selection screening (as shown in FIG. 1A-F) and DNA sequencing revealed the presence of 269 unique, human and mouse CD47-binding scFv clones that retained epitope binding competition with h5F9G4 IgG1, blocked the binding of hCD47 to hSIRPα and contained significantly increased human content within the CDRs, while the framework sequences remained fully germline. Amongst these 269 clones, germ-lining mutations were observed in all CDRs (Table 3). Lead clones were ranked based on the level of CDR germ-lining versus assay technology known under the trademark HTRF® signals for both human CD47-Fc and h5F9G4 (FIG. 1). The v-domains of the 11 top clones from this ranking were then sub-cloned into IgG expression vectors for further testing as below (Table 4). Unexpectedly however, in all analyses of both CD47-SIRPα and CD47-h5F9G4 neutralisation, none of the library derived clones, nor the IGKV2-28/IGHV5-51 graft scFv achieved the same potency as the IGKV2-28/IGHV1-3-grafted h5F9G4 scFv (FIG. 1A-F).

Figure 2A:
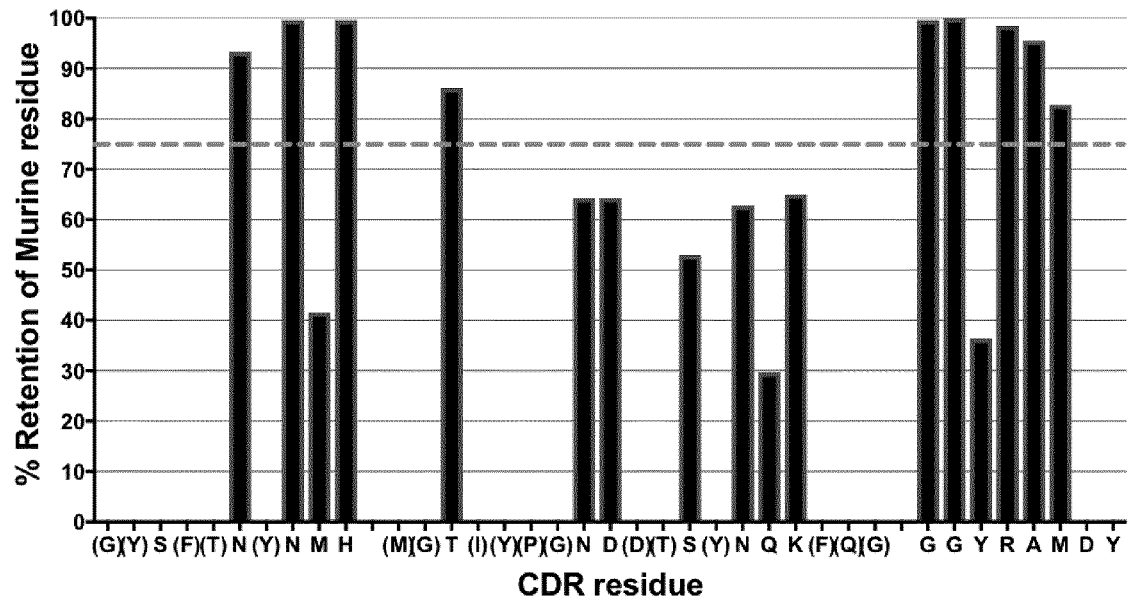
FIG. 2A-FIG. 2B. Analysis of CDR residue tolerance for mutation to germline. A plot of murine amino acid retention frequencies in the CDRs of the ELISA-positive population of 269 unique scFv clones is shown for $V_H$ (SEQ ID NOs: 64-66) (FIG. 2A) and $V_L$ (SEQ ID NOs: 67-69) (FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV2-28 and IGHV5-51). Those residues in the HCDR2 that are not in parentheses, but whose values are set at 0, were mutated to human germline during the grafting process. In both plots the dashed line in grey at 75% represents the cut off for tolerance of murine residue replacement by human germline.
Figure 2B:
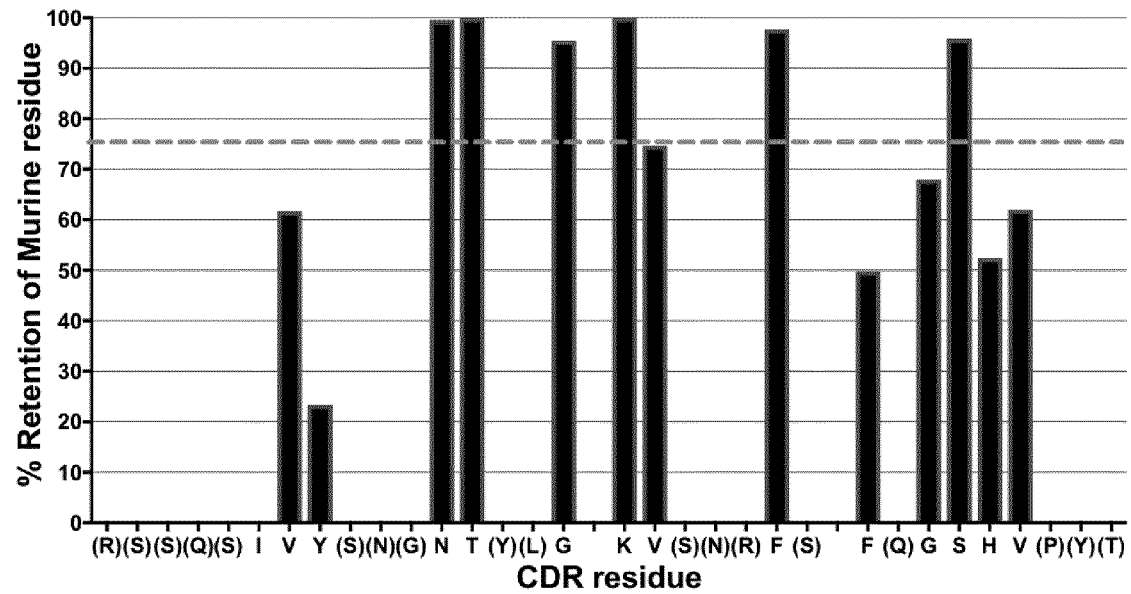

While germ-lining mutations were observed in all CDRs for the lead clones derived directly from library selections, it remained possible that sequence analyses might allow further clones to be designed to have maximal humanization and retain maximal CD47 binding affinity and antagonism potency. The 269 sequence-unique hits with binding signals against human and mouse protein were therefore used to analyse the retention frequency for murine amino acids in the CDRs of this functionally characterized population. Positional amino acid retention frequency was expressed as a percentage found in the $V_H$ and $V_L$ domains (FIG. 2A, 2B). Murine residues with RF<75% were regarded as positions that are possibly not essential to the target-binding paratope and are likely to be open to germ-lining, in a series of combinatorial designs. Importantly, as observed in the scFv screening data outlined above, the potency of the IGHV5-51-grafted VH domains was deemed likely to be lower than those on a IGHV1-3 framework. To examine whether or not this was the case, the paratope sampling information outlined in FIGS. 2 A and B was used to construct designer clones in the IGKV2-28 and IGHV1-3 frameworks for comparison alongside the heavily-humanized clones derived from the initial library (IGHV5-51 framework in the VH domain).

Ten VH designs containing principally those murine residues with RF>75%, in a number of combinations, were designated VH1.1-VH1.10. Six VL designs were also created (VL1.1-VL1.6) that combined the most humanized CDRs observed in the high-functioning population of scFv sequences, plus further-humanizing and deamidation motif-disrupting mutations in the LCDR1 (Table 4). These LCDR1 humanizing and stabilising mutations sampled positions 11, 12 and 13 (residues GNT), which had been observed to be variable positions (FIG. 2A, Table 3), but had not explicitly demonstrated that these potentially optimal sequences (e.g. the 'ANT' and especially 'AYN' motifs found in designer chain VL1.4 and others outlined in Table 4) could be tolerated while retaining target binding specificity and the ability to block CD47-SIRPα interaction.

The VH and VL clones were generated by gene synthesis (along with the 11 library-derived clones outlined above, positive controls IGHV5-51 graft, h5F9G4 and m5F9G4, and negative control non-CD47-reactive v-domains), then cloned into expression vectors for production as human IgG1null. To maximise the opportunity to find functional optimised sequences, the designer VH and VL clones were matrixed to combine all potential combinations of VH and VL sequences. To examine whether or not the observed reduced potency of the IGHV5-51-based scFvs observed above was due to scFv formatting and not the framework choice, the scFv of lead clone D6 was cloned as both IgG1 and scFv-Fc fusion formats. All IgGs and the D6 scFv-Fc fusion protein were readily expressed and purified from transient transfections of HEK-293 cells.

Library-Derived Lead IgG Specificity and Potency Characteristics

Figures 3A, 3B:
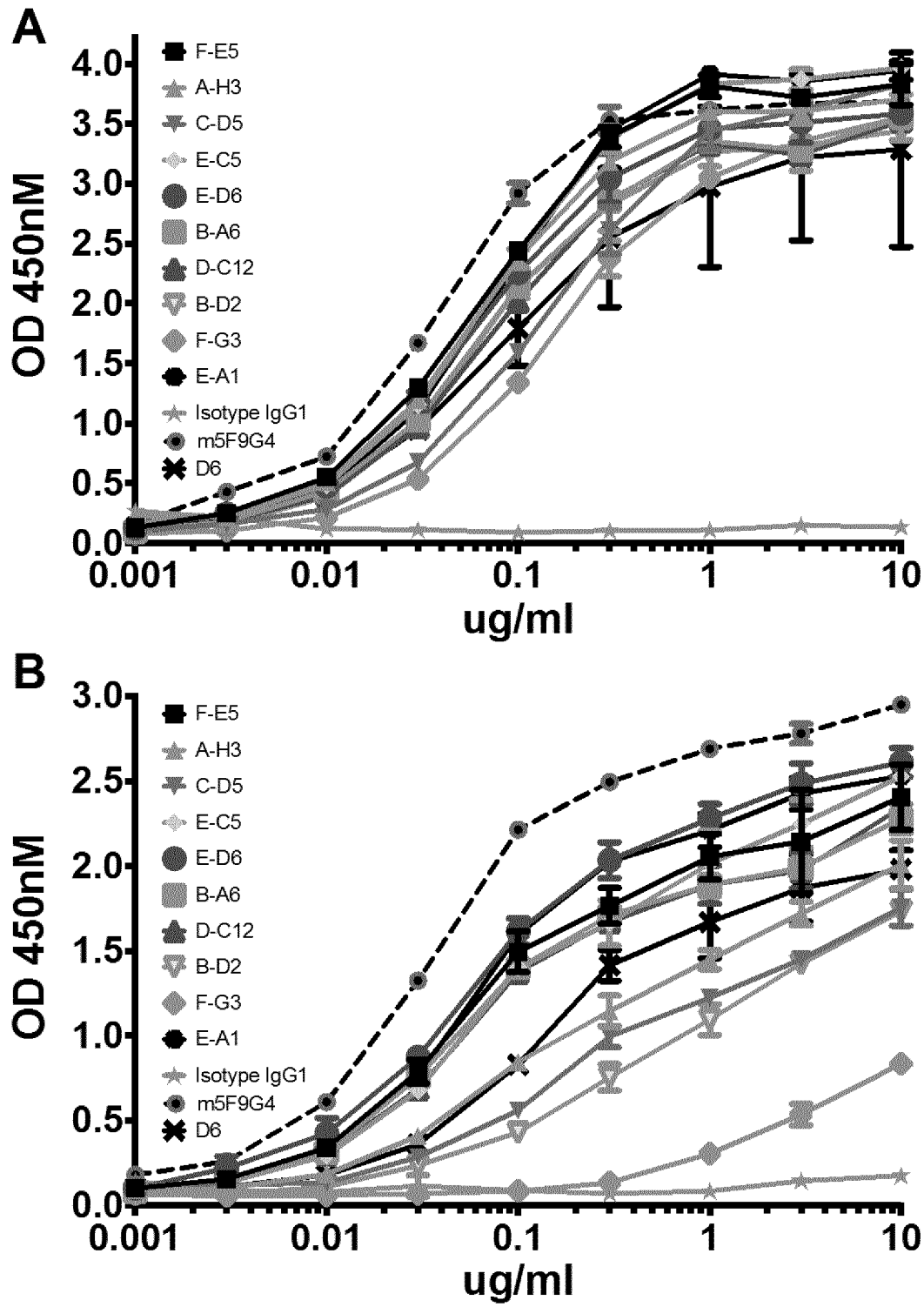
FIG. 3A-FIG. 3B. Direct titration ELISA for library-derived lead IgGs binding to human and cyno CD47-Fc proteins. Chimeric anti-CD47 (m5F9G4) and library-derived clones in human IgG1null format were titrated (in μg/ml) in a direct binding ELISA against human (FIG. 3A) and cyno (FIG. 3B) CD47-Fc proteins. The m5F9G4 and library-derived clones demonstrated binding activity against both orthologs of CD47.

The purified IgGs described above were then tested for binding to human and cyno CD47-Fc in direct titration ELISA format. This analysis demonstrated that while all library derived clones clones retained binding affinity for human CD47, none fully recapitulated the binding of m5F9G4 IgG1 (FIG. 3A). This reduced binding was more pronounced on cyno CD47, with clone F-G3 showing particularly weak reactivity (FIG. 3B).

Figures 4A, 4B:
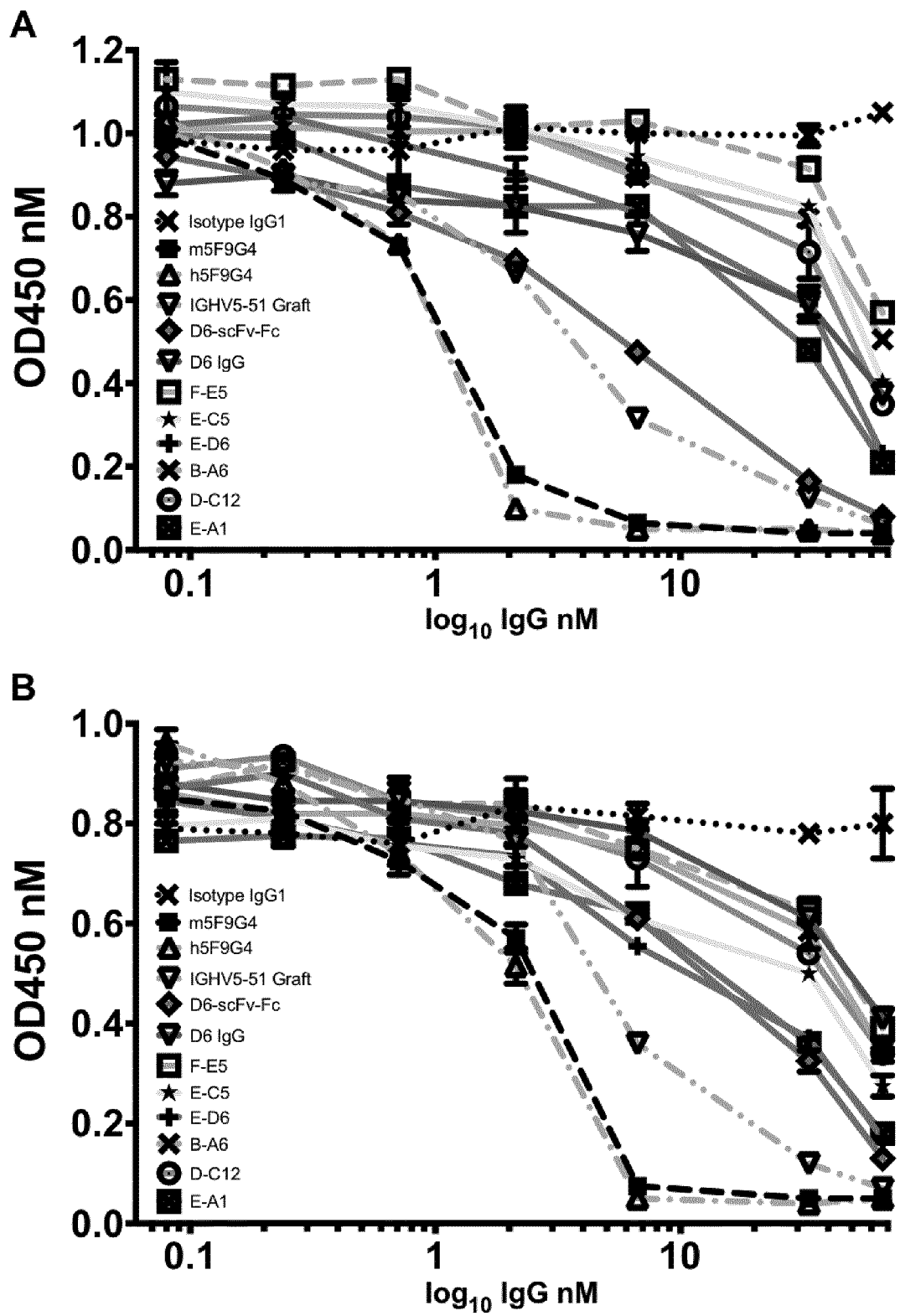
FIG. 4A-FIG. 4B. ELISA-based CD47-Fc-SIRPα competition assay for library-derived leads. ELISA binding signal for human (FIG. 4A) and cyno (FIG. 4B) CD47-Fc proteins to plate-bound human SIRPα was examined in the presence of titrated competitor IgGs in IgG1null format, D-A6 scFv-Fc, plus Isotype IgG1, IGHV5-51 graft, h5F9G4 and m5F9G4 in IgG1null format.

As direct ELISA binding signal is influenced by avidity and does not prove the maintenance a specific epitope, all IgGs were then examined in a CD47-SIRPα binding blockade assay (FIG. 4) and a solution-phase assay technology known under the trademark HTRF® competition assay of 5F9G4 binding to CD47 (FIG. 5). In the CD47-SIRPα binding blockade assay, all library-derived IgGs exhibited significantly reduced potency in comparison to h5F9G4, m5F9G4 and the IGHV5-51 grafted IgG, whether binding to human (FIG. 4A) or cyno CD47 (FIG. 4B). Importantly, the IGHV5-51-grafted IgG demonstrated the ability to fully block the binding of both human and cyno CD47 to SIRPα, but with demonstrably reduced potency in comparison to h5F9G4. This suggested that the grafting process of placing the 5F9G4 CDRs onto the IGHV5-51 framework had specifically reduced the potency of the molecule in comparison to h5F9G4, as the CDR sequences are maintained across both frameworks. In a further unexpected finding, the D6 scFv-Fc fusion protein maintained the starting CD47 blocking potency of the IGHV5-51 graft IgG against both orthologs, while the D-A6 IgG did not and was incapable of fully blocking either ortholog (FIG. 4A, 4B).

Figure 5A:
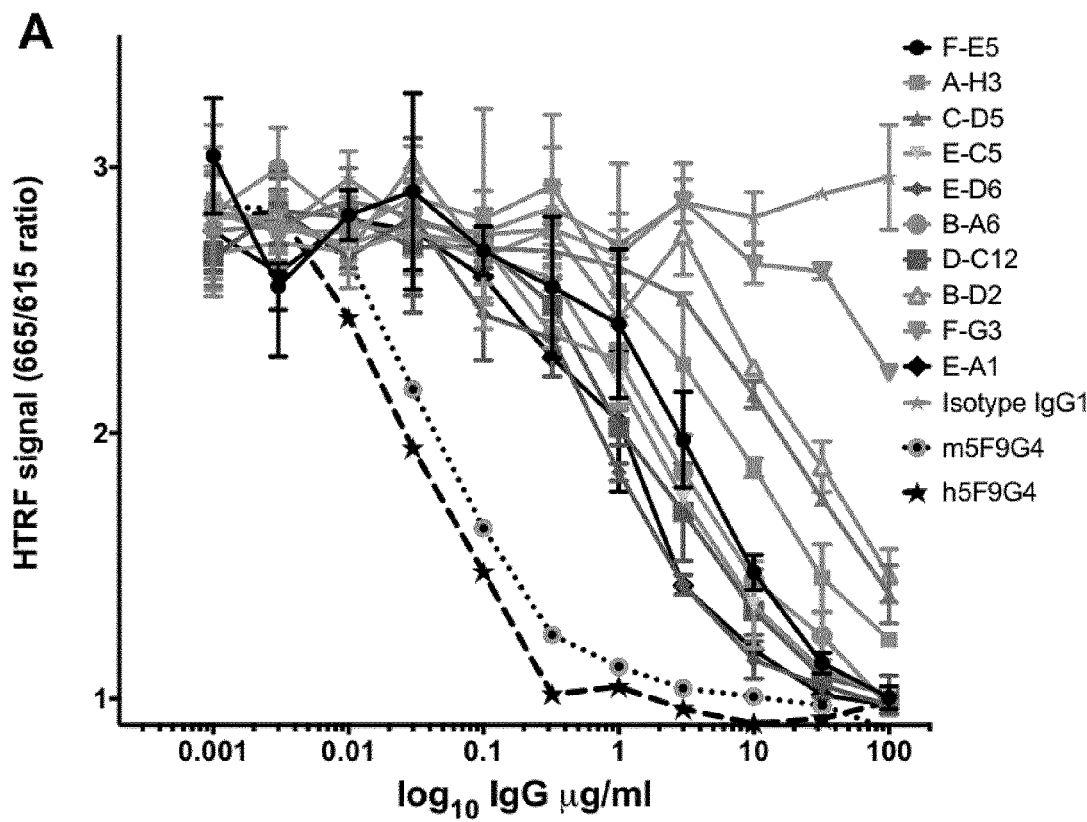
FIG. 5A-FIG. 5B. Assay technology known under the trademark HTRF®-based solution-phase, high-sensitivity, CD47 epitope competition assay for library-derived leads. Assay technology known under the trademark HTRF® binding signal for the h5F9G4 IgG to human or cyno CD47 was examined in the presence of titrated competitor IgGs including library-derived leads, plus Isotype IgG1 and unlabelled h5F9G4 and m5F9G4. All library-derived leads exhibited concentration-dependent inhibition of h5F9G4 binding to human CD47, suggesting maintenance of a shared epitope, but lower binding affinity (FIG. 5A). Both D-A6 proteins (IgG and scFv-Fc) demonstrated the ability to fully inhibit h5F9G4 binding to human CD47 (FIG. 5B), with the scFv-Fc fusion form of the identical v-domains being higher potency than the IgG.
Figure 5B:
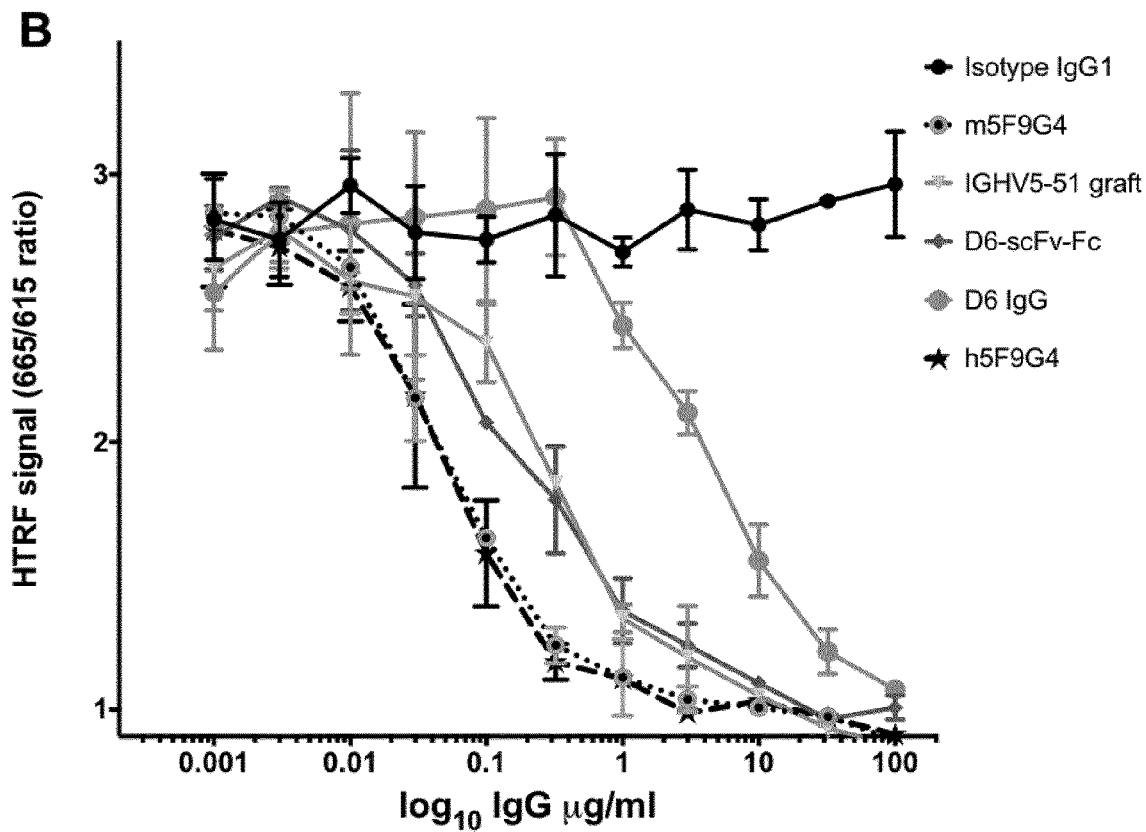
Figures 6A, 6B:
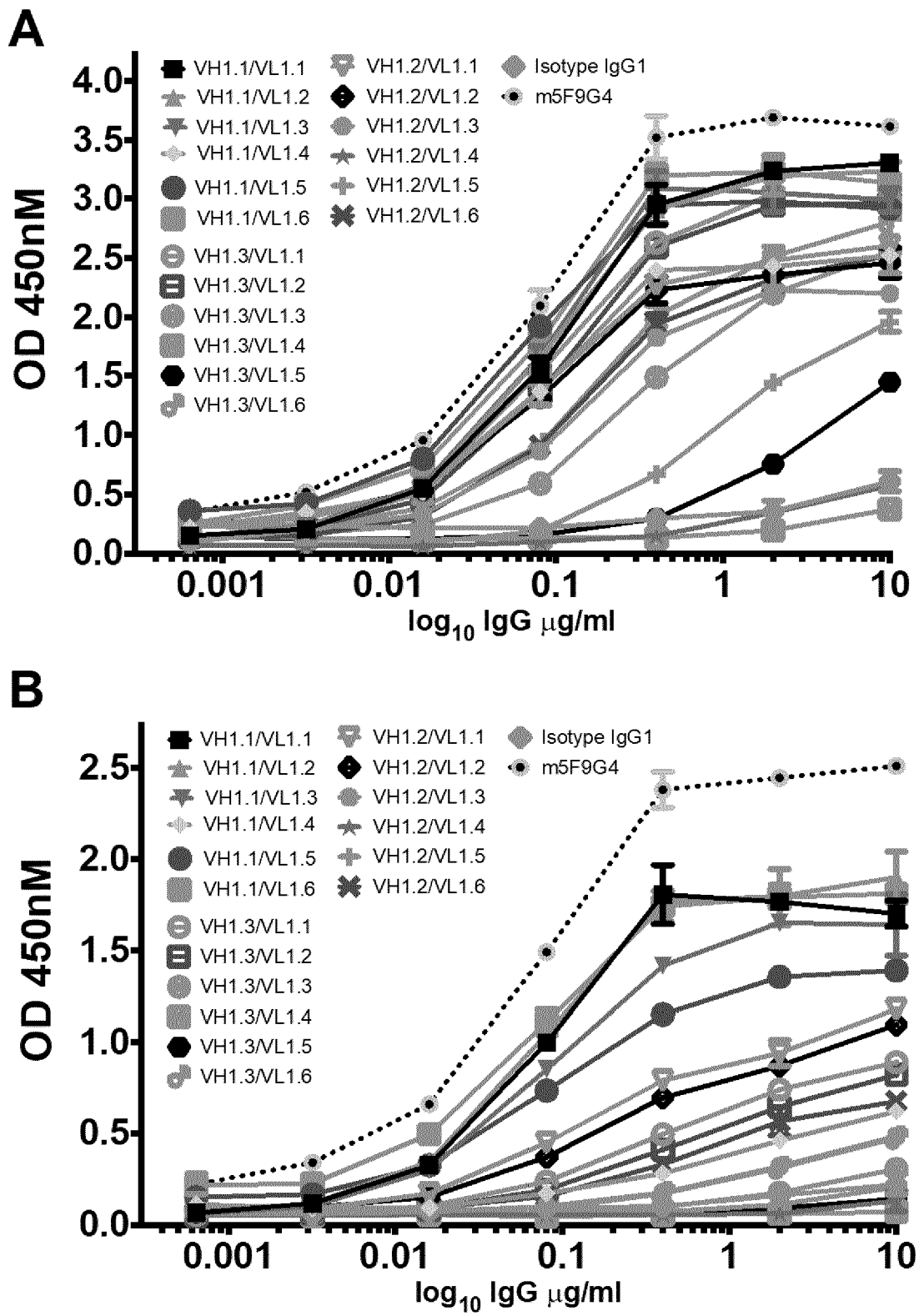
FIG. 6A-FIG. 6H. Direct titration ELISA for designer lead IgGs binding to human and cyno CD47-Fc proteins. Chimeric anti-CD47 (m5F9G4) and designer clones in human IgG1null format were titrated (in μg/ml) in a direct binding ELISA against human and cyno CD47-Fc proteins. The m5F9G4 and library-derived clones demonstrated binding activity against both orthologs of CD47: VH1.1-VH1.3 families versus human (FIG. 6A) and cyno (FIG. 6B); VH1.4-VH1.6 families versus human (FIG. 6C) and cyno (FIG. 6D); VH1.7, VH1.9 and VH1.10 families against human (FIG. 6E) and cyno (FIG. 6F); and VH1.8 family against human (FIG. 6G) and cyno (FIG. 6H).
Figure 6C:
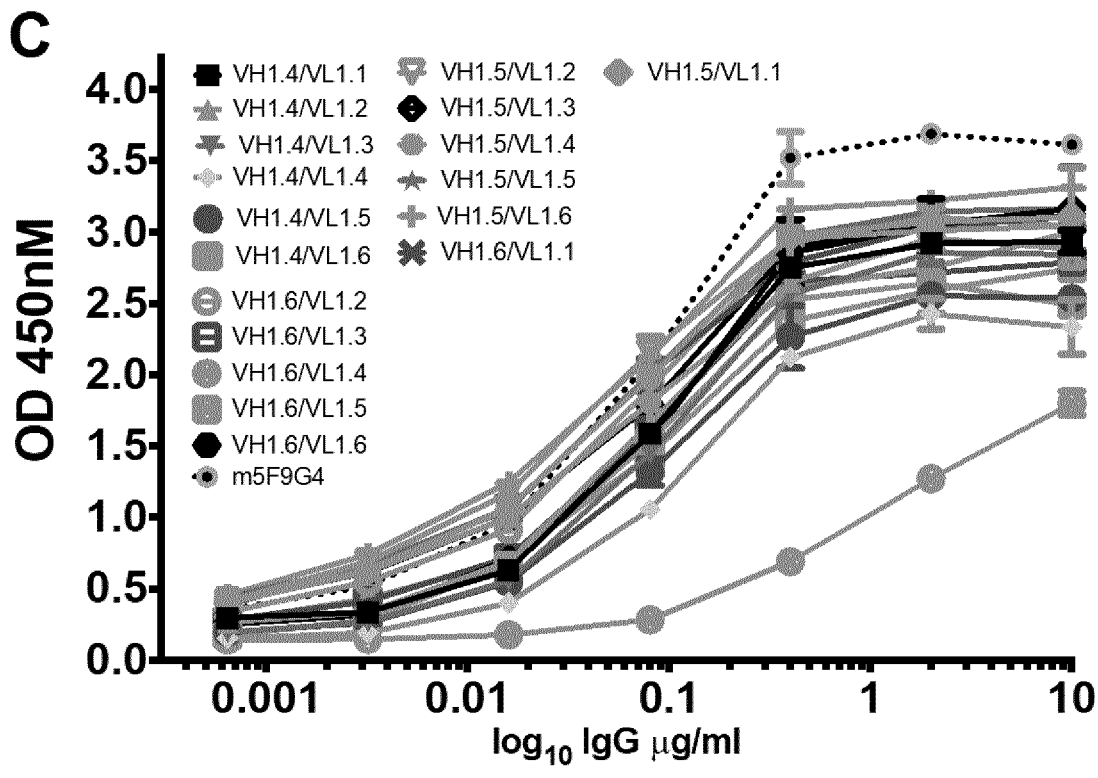
Figure 6D:
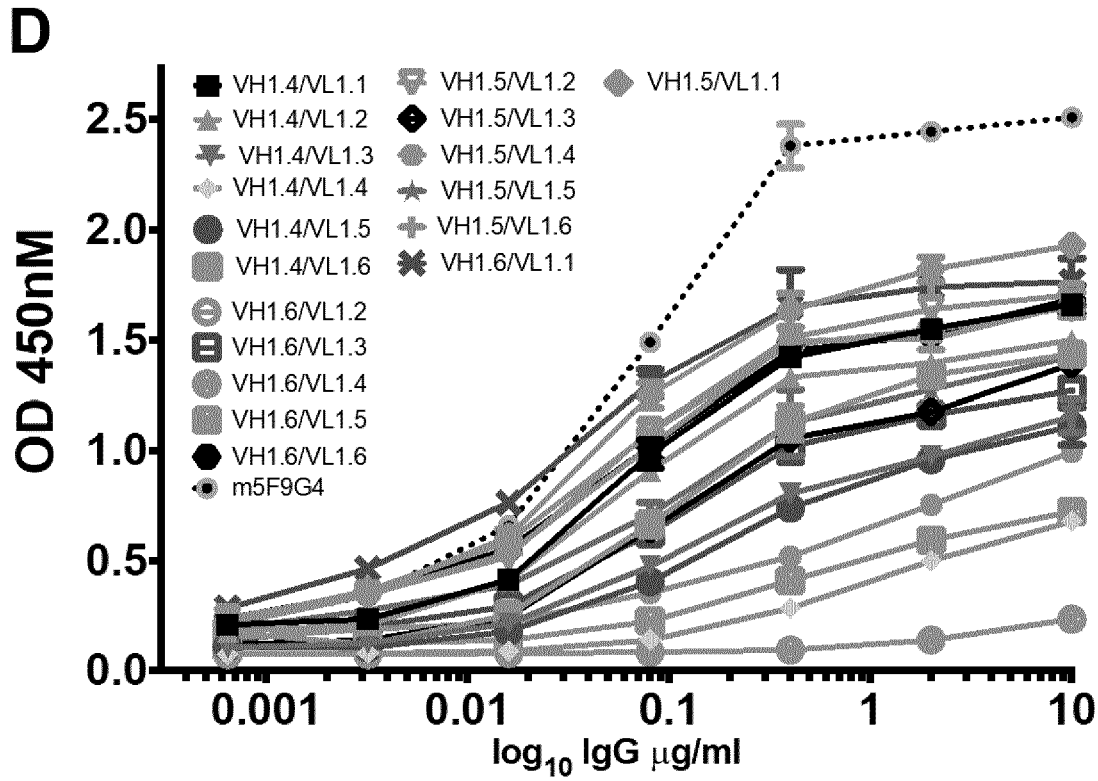
Figure 6E:
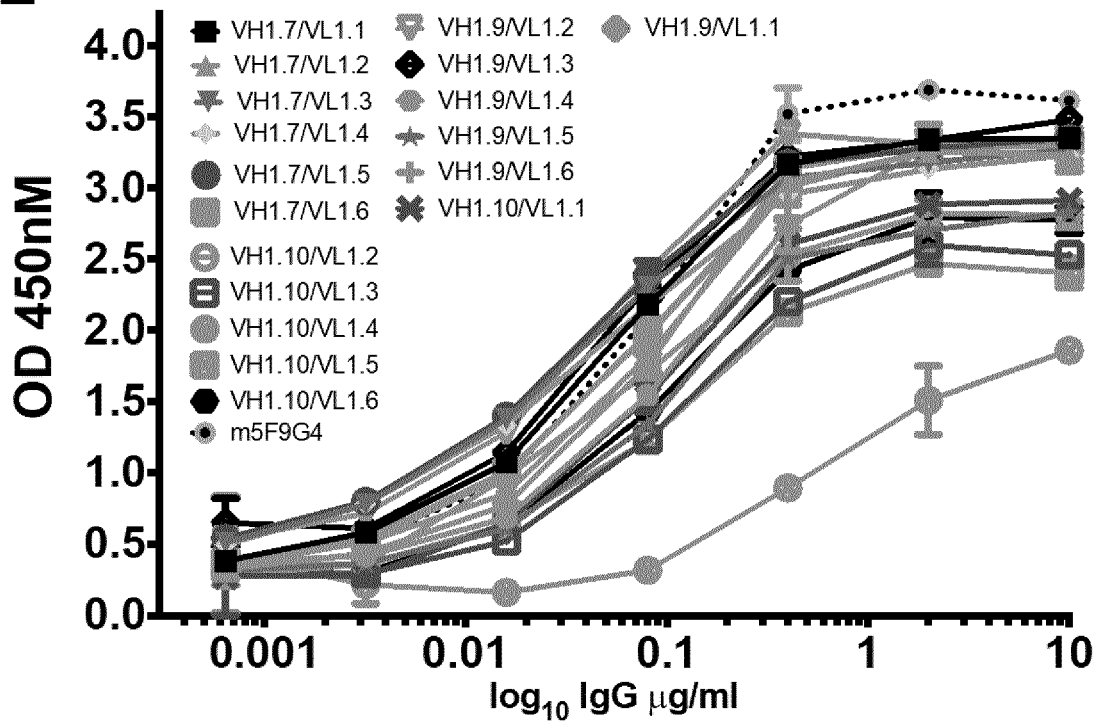
Figure 6F:
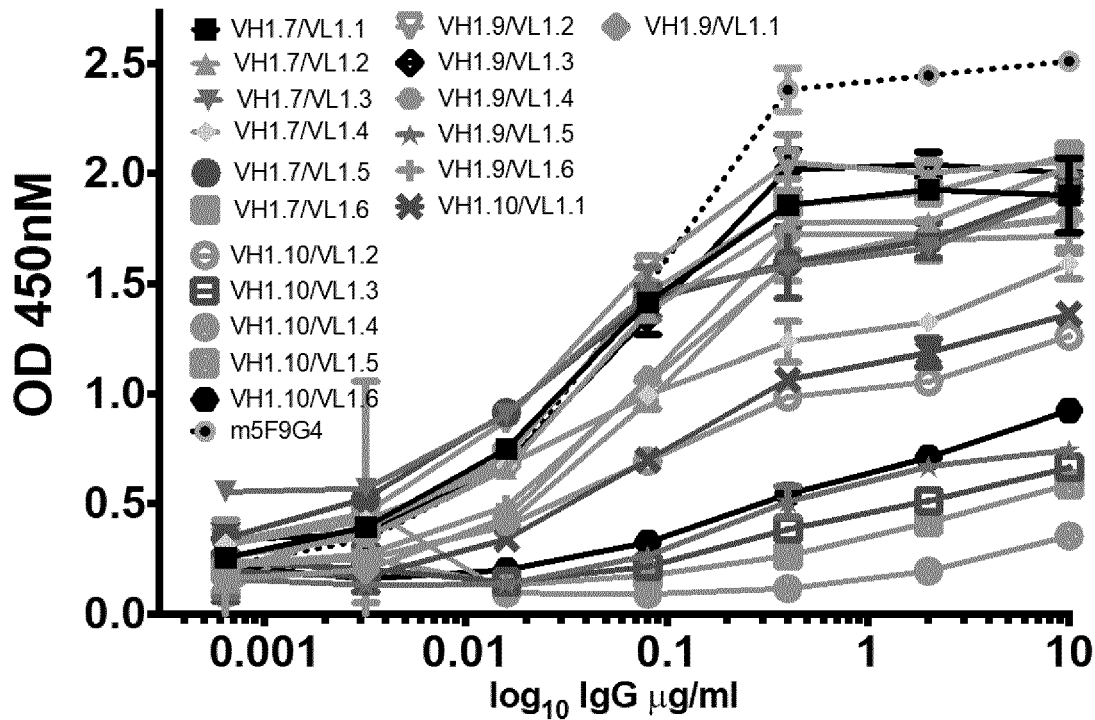
Figure 6G:
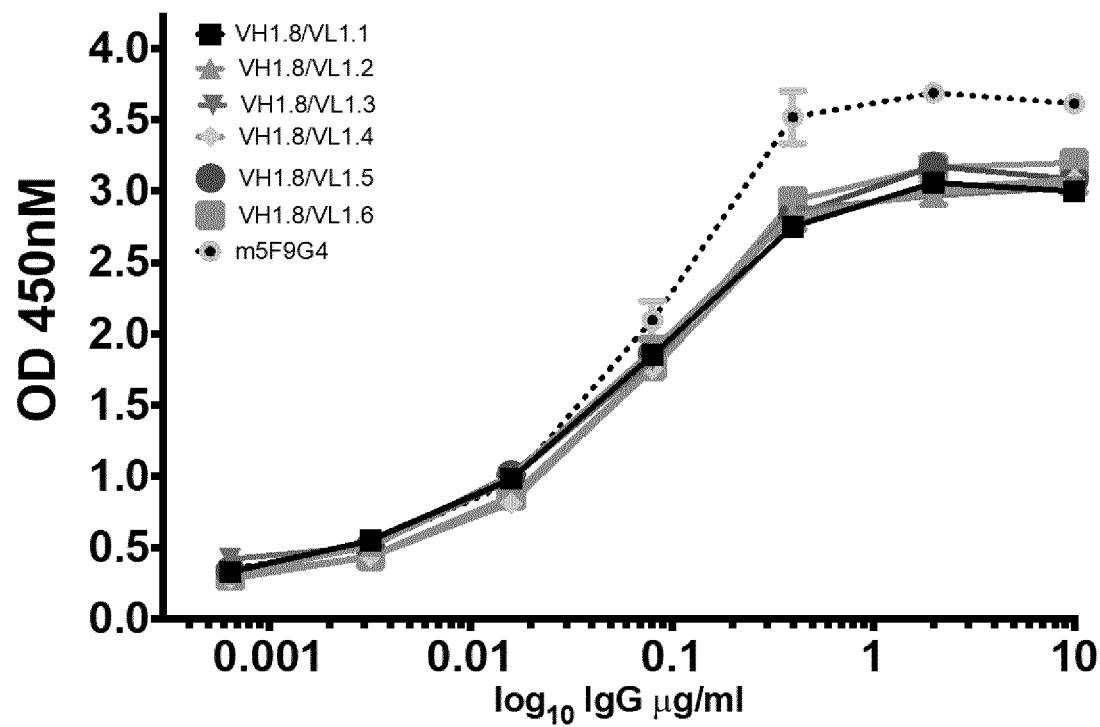
Figure 6H:
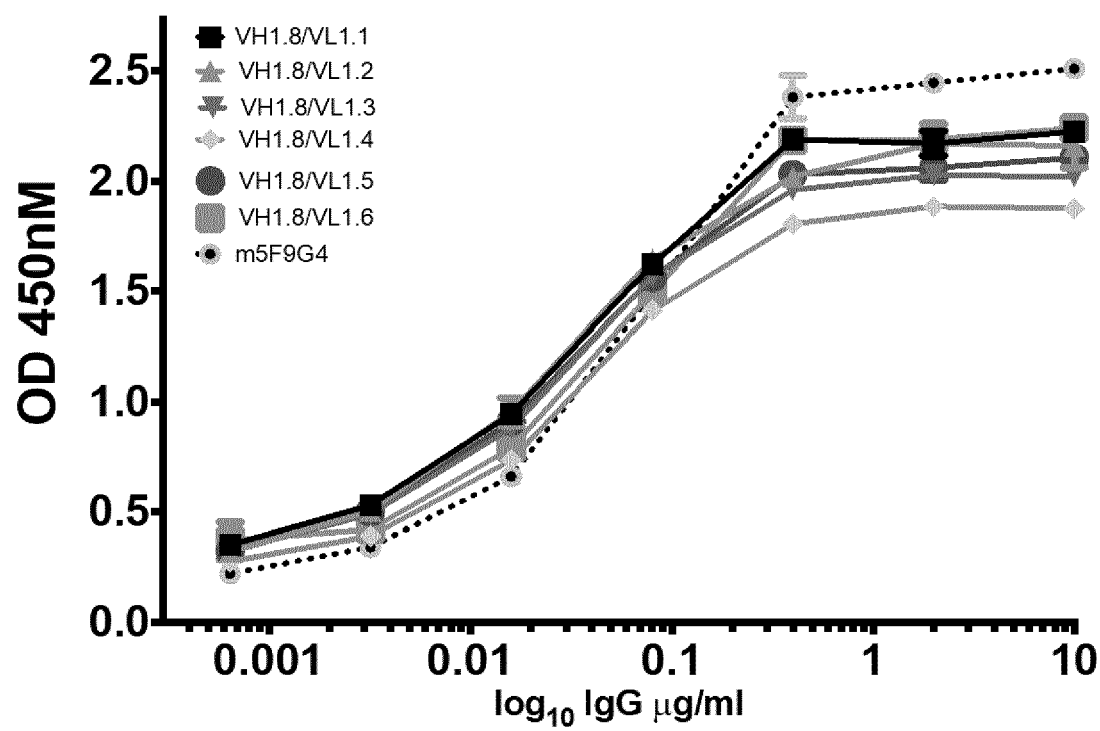

To ensure that the observed loss of CD47 blockade potency by some IGHV5-51-framework clones was not driven by the phenomenon of 'epitope shift', an assay technology known under the trademark HTRF® assay was performed. This assay examined the ability of these clones to compete for the binding of h5F9G4 to CD47. These analyses showed that almost all clones (F-G3 excepted) could cross-compete with h5F9G4, with most clones demonstrating full inhibition of binding at the highest concentration (FIG. 5A). Potency of inhibition was again reduced in comparison to h5F9G4 self-competition, however. This finding suggested maintenance of a shared epitope, but reduced binding affinity in the IGHV5-51 framework clones. Importantly, the improved function of the D6 scFv-Fc over the D6 IgG was again demonstrated, with the D6 scFv-Fc showing equivalent potency to the IGHV5-51 graft IgG, while the D-A6 IgG was clearly reduced potency (FIG. 5B).

The findings regarding D6 scFv-Fc fusion potency versus D6 IgG strongly suggested that the process of re-grafting the CDRs, coupled with scFv display and screening had unexpectedly selected for clones which are preferentially functional in scFv format, which are then impaired when reconfigured into IgG1. This observation renders such clones particularly attractive in bispecific antibody generation as scFv fragments can be successfully used as modular building blocks of multi-specific antibodies. In totality, however, these findings also illustrate that the original methods of Townsend et al. had failed to generate an improved version of h5F9G4

Designer IgG Specificity and Potency Characteristics

The purified designer IgGs described above were then tested for binding to human and cyno CD47-Fc in direct titration ELISA format. This analysis demonstrated that while many clones retained binding affinity for human and cyno CD47, the range of binding potencies was highly heterogeneous, with some clones being significantly reduced in binding signal, but with a subset of IgGs fully recapitulating the binding of m5F9G4 IgG1 (FIG. 6A-H). The family of clones containing the VH1.8 VH domain in combination with the VL1.1-1.6 domains demonstrated the most consistent recapitulation of the full binding potency of m59G4 and are shown separately in FIGS. 6G and H.

Figure 7A:
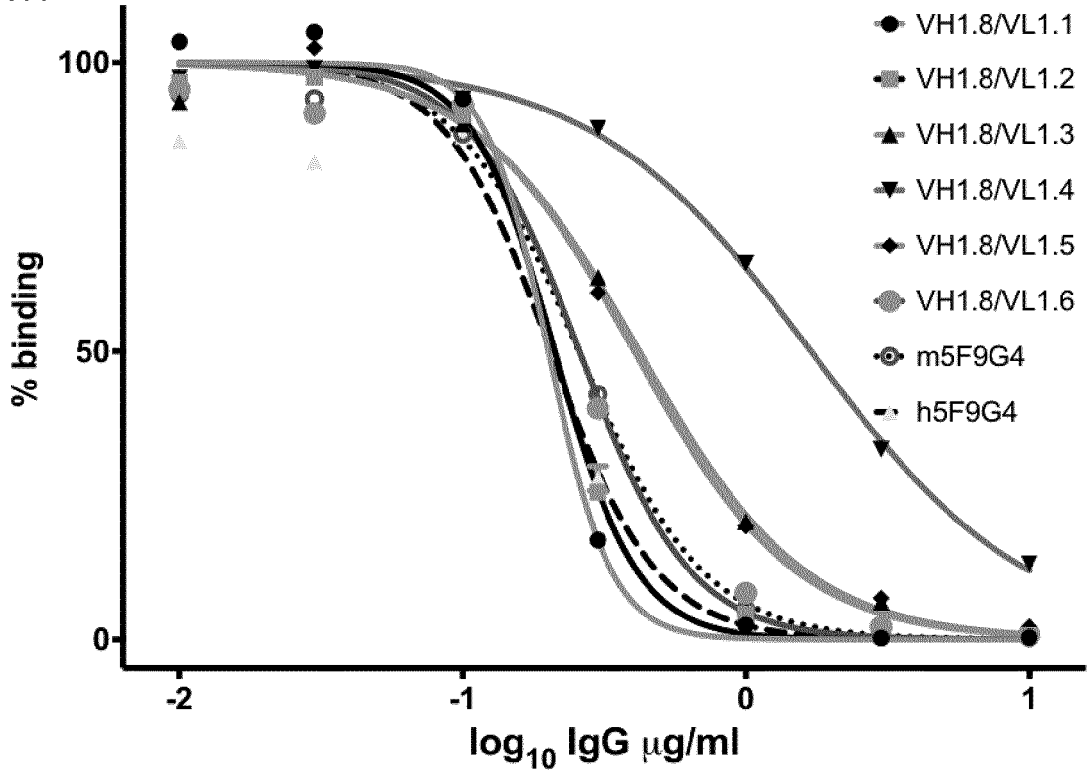
FIG. 7A-FIG. 7B. ELISA-based CD47-Fc-SIRPα competition assay for VH1.8 family designer leads. ELISA binding signal for human (FIG. 7A) and cyno (FIG. 7B); CD47-Fc proteins to plate-bound human SIRPα was examined in the presence of titrated competitor IgGs in IgG1null format, plus m5F9G4 and h5F9G4 in IgG1null format as positive controls.
Figure 7B:
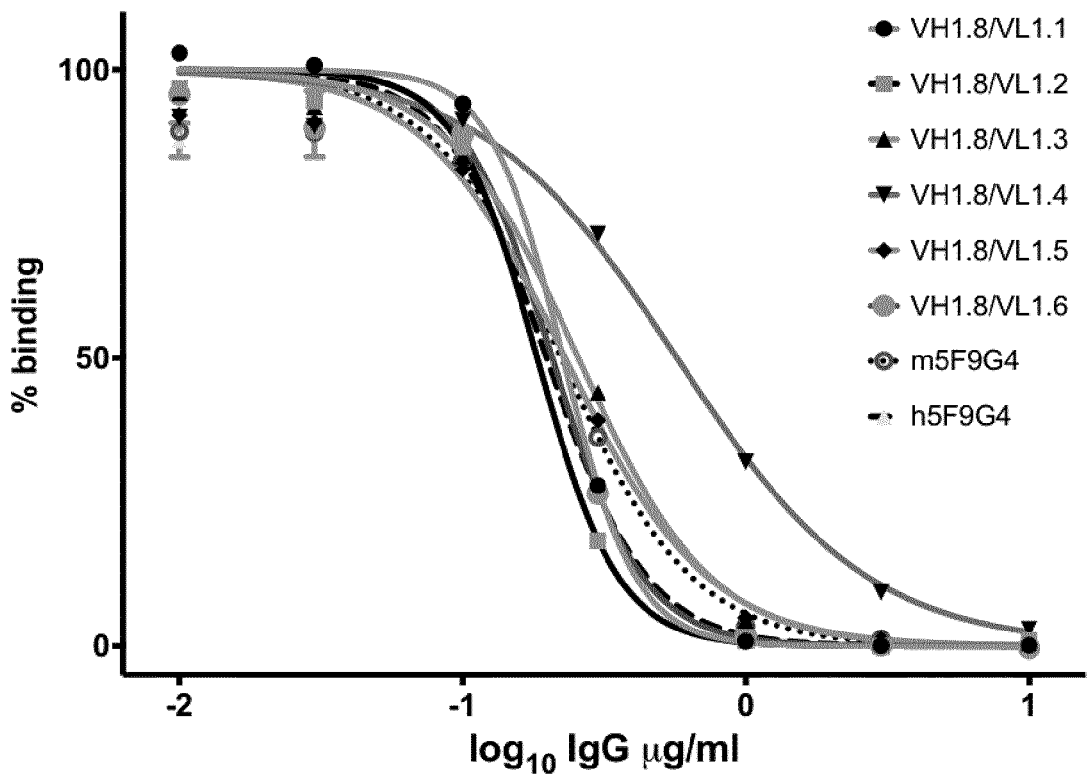
Figure 8:
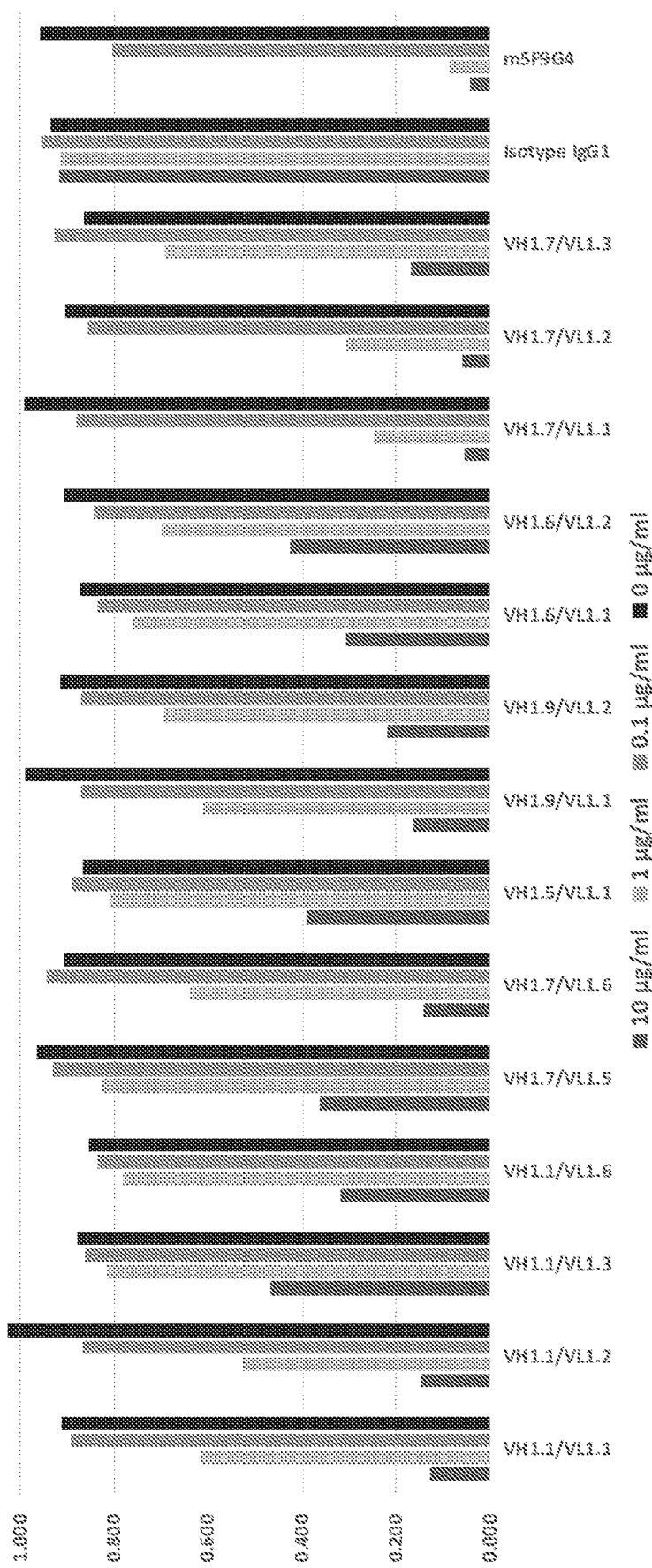
FIG. 8. ELISA-based CD47-Fc-SIRPα competition assay for further designer leads. ELISA binding signal for human CD47-Fc to plate-bound human SIRPα was examined in the presence of titrated competitor IgGs in IgG1null format, plus Isotype IgG1 and m5F9G4 in IgG1null format.

As direct ELISA binding signal is influenced by avidity and does not prove the maintenance a specific epitope, all IgGs were then examined in a CD47-SIRPα binding blockade assay (FIG. 7, FIG. 8). In the CD47-SIRPα binding blockade assay, all VH1.8 family IgGs exhibited high potency, with functional equivalency for all clones other than VH1.8/VL1.4, in comparison to h5F9G4 and m5F9G4, whether binding to human (FIG. 7A) or cyno CD47 (FIG. 7B). Several other designer clones which had performed well in ELISA also exhibited the ability to block hCD47-SIRPα binding (FIG. 8), albeit with lower potency than the VH1.8 family clones.

Figures 9A, 9B, 9C, 9D:
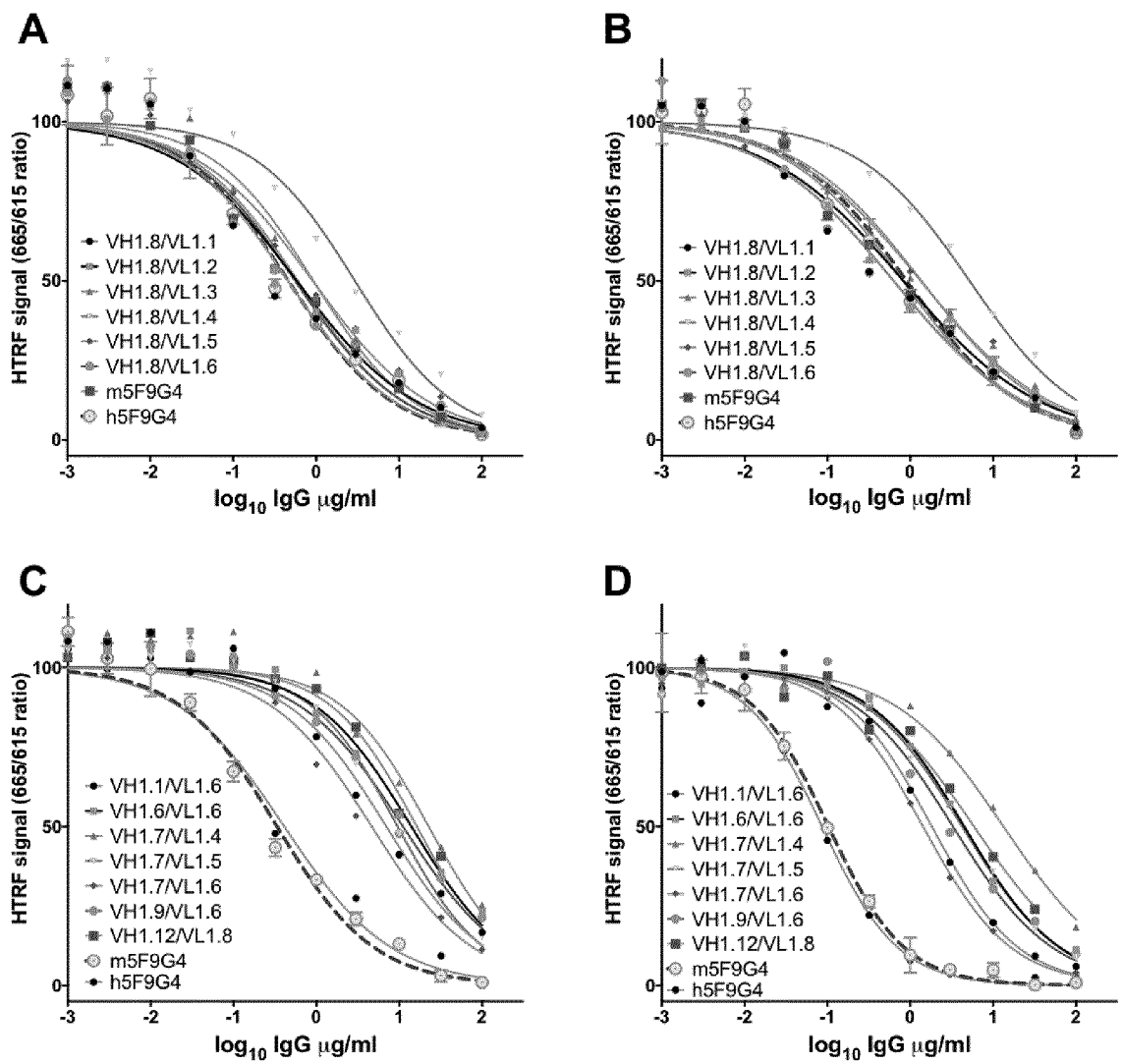
FIG. 9A-FIG. 9D. Assay technology known under the trademark HTRF®-based solution-phase, high-sensitivity, CD47 epitope competition assay for designer leads. Assay technology known under the trademark HTRF® binding signal for the h5F9G4 IgG to human or cyno CD47 was examined in the presence of titrated competitor IgGs including library-derived leads, plus unlabelled h5F9G4 and m5F9G4 as positive controls. All VH1.8-family designer leads exhibited potent concentration-dependent inhibition of h5F9G4 binding to human (FIG. 9A) and cyno (FIG. 9B) CD47. Other selected designer leads also exhibited concentration-dependent inhibition of h5F9G4 binding to human (FIG. 9C) and cyno (FIG. 9D) CD47, with reduced potency.
Figure 10A:
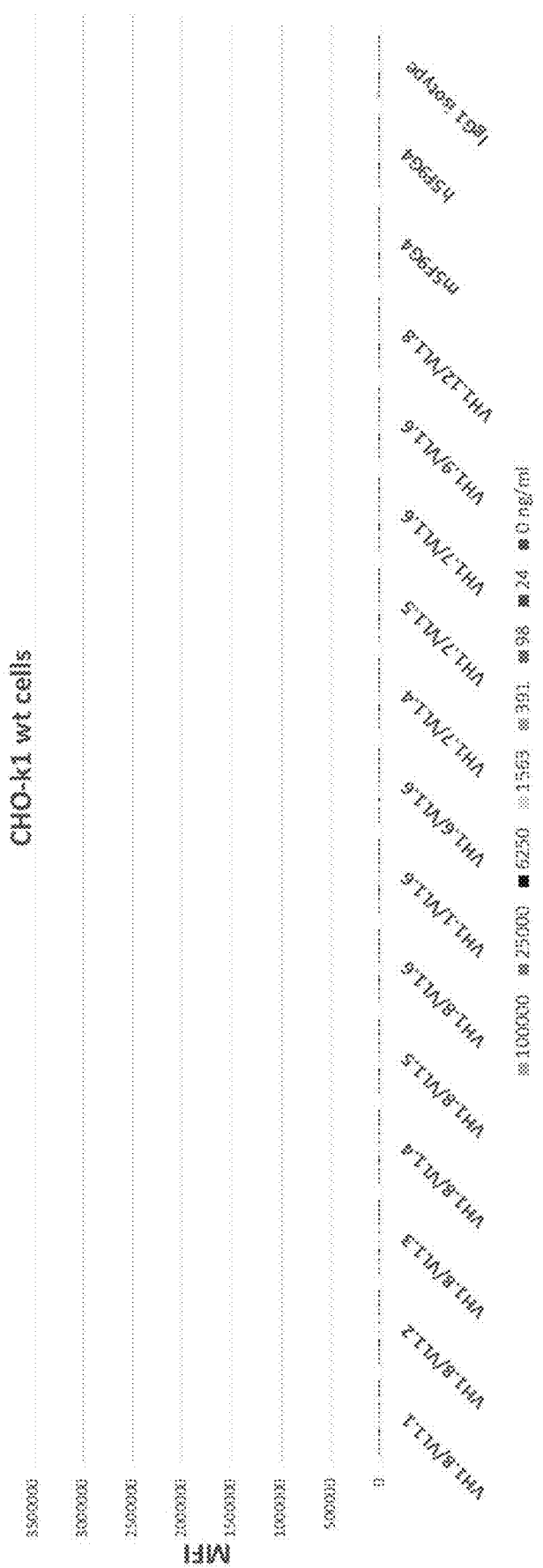
FIG. 10A-FIG. 10D. Flow cytometric binding to HL60, human and cyno CD47+ CHO-K1 cells for designer leads. Anti-CD47 controls m5F9G4 and h5F9G4, designer leads and Isotype control (all IgG1null) were examined for specific binding on wild type (WT, i.e. untransfected) CHO-K1 cells (FIG. 10A), human CD47-transfected CHO-K1 cells (FIG. 10C), cyno CD47-transfected CHO-K1 cells (FIG. 10B), and the human AML cell line HL60 (FIG. 10D). IgGs were tested at concentrations ranging from 24-100,000 ng/ml. Concentration-dependent binding was observed against human and cyno cell lines, plus HL60 cells, for all CD47-specific antibodies but not isotype controls. No binding signals above background were observed against wild type CHO-K1 cells.
Figure 10B:
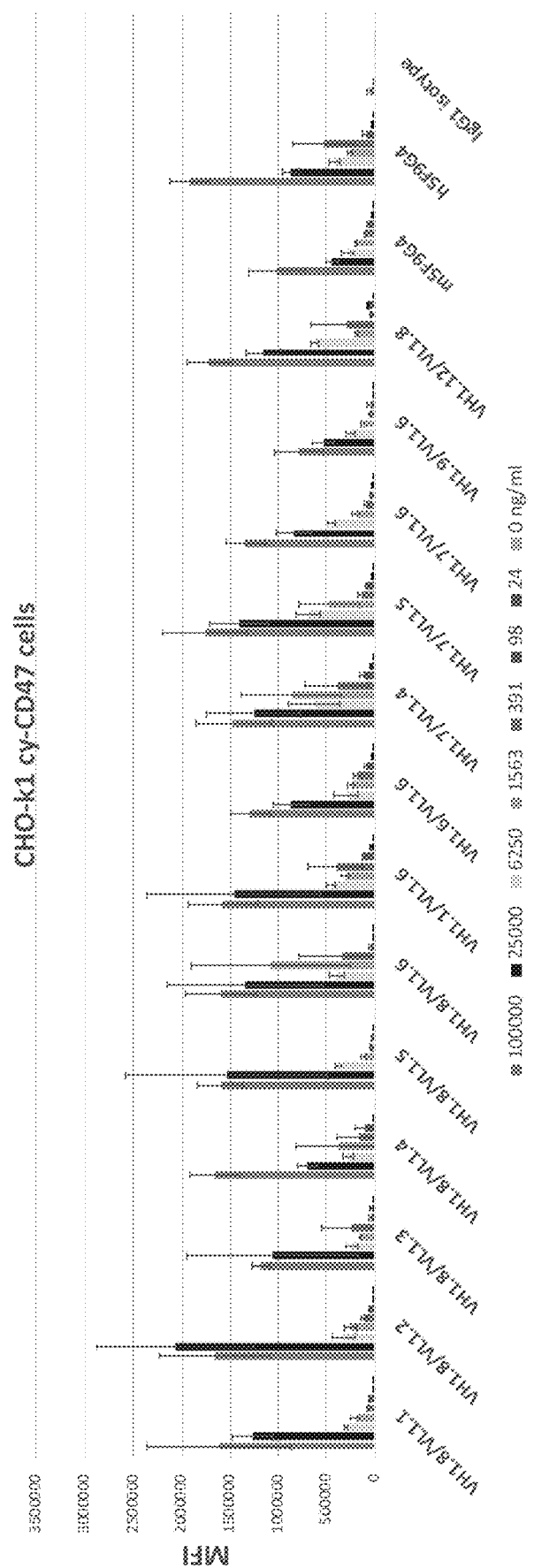
Figure 10C:
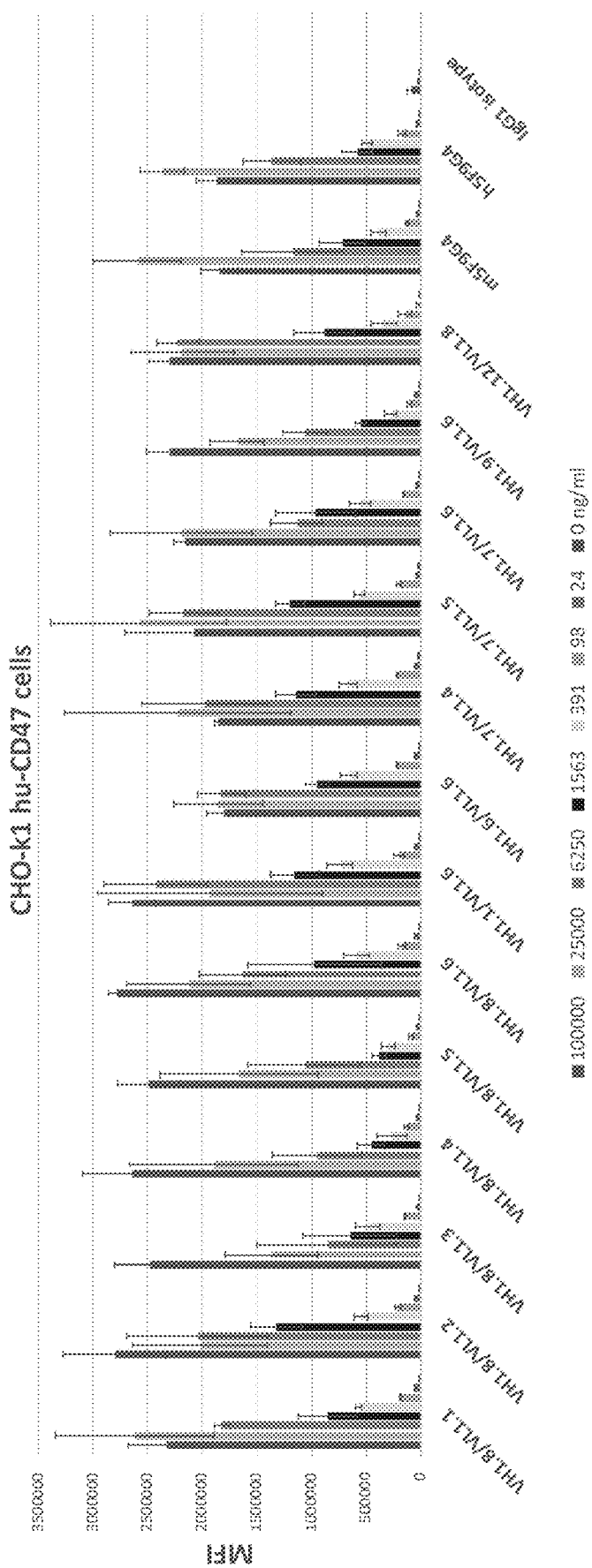
Figure 10D:
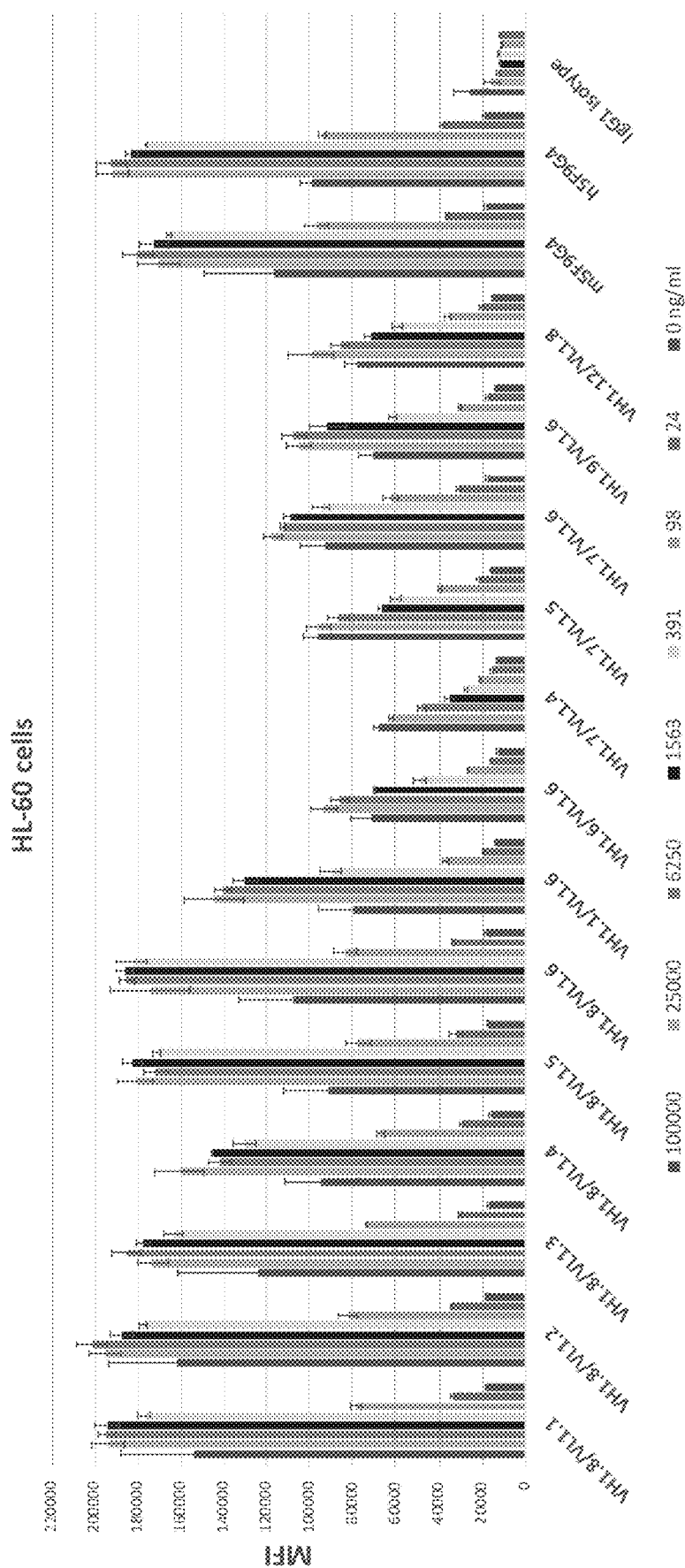

To ensure that the observed maintenance of CD47 blockade potency by high-functioning designer clones was coupled with maintained epitope specificity, a solution-phase assay technology known under the trademark HTRF® competition assay of 5F9G4 binding to CD47 was performed (FIG. 9). This assay examined the ability of the key designer clones to compete for the binding of h5F9G4 to CD47. These analyses showed that all VH1.8 family clones could cross-compete with h5F9G4, with multiple clones demonstrating equivalent (Table 5) potency against human (FIG. 9A) and cyno (FIG. 9B) CD47. The potency of inhibition for VH1.8/VL1.4, however, was again reduced in comparison to h5F9G4 self-competition. This finding suggested maintenance of a shared epitope, but reduced binding affinity for the VL1.4 domain-containing clones. Further assay technology known under the trademark HTRF® analyses showed that all non-VH1.8 family clones which demonstrated hCD47 blockade (FIG. 8) could also cross-compete with h5F9G4, but with all clones demonstrating reduced potency (Table 5) against human (FIG. 9C) and cyno (FIG. 9D) CD47. In an attempt to further sample CDR residues in the VH1.8 background, two further designs (VH1.11 and VH1.12) were generated, along with 3 more designer descendants of the VL1.5 sequence (VL1.7, VL1.8 and VL1.9). These designs were co-expressed in a matrix to produce 6 further IgGs, then examined in the CD47-SIRPα blockade assay. This analysis showed that all of the clones had lost all potency in antagonising CD47, other than VH1.12/VL1.8, which maintained minimal blocking (<50%) at 10 µg/ml. These findings showed that the mutation of F>A at position 6 of the LCDR2, or the mutation F>M at position 1 of the LCDR3 both led to the full ablation of CD47 antagonism.

Flow Cytometric Analyses of Lead IgG Binding Specificity at the Cell Membrane

Antibodies shown to retain binding to CD47 by ELISA were analysed for concentration-dependent binding at the cell surface via flow cytometry. CHO-K1 cells were stably transfected with either human or cyno CD47 full-length cDNAs. Anti-CD47 IgGs and an isotype control IgG1 were then all tested in IgG1null format, over a concentration range of 100-0.024 µg/ml for binding to human, cyno, or wild type control ('wt', i.e. untransfected) CHO-K1 (FIGS. 10A-D). All IgGs other than the isotype control showed concentration-dependent binding to human and cyno CD47+ cells, and also to human AML cell line HL60, with a maximum MFI in each case being >50-fold higher than observed background signals for binding to untransfected CHO-K1. Anti-CD47 antibodies exhibited no measurable background binding on untransfected CHO-K1 cells, comparable to the Isotype control IgG1 (FIGS. 10A-D).

Lead IgG Analyses in 'Developability' ELISA Assays

Figure 11A:
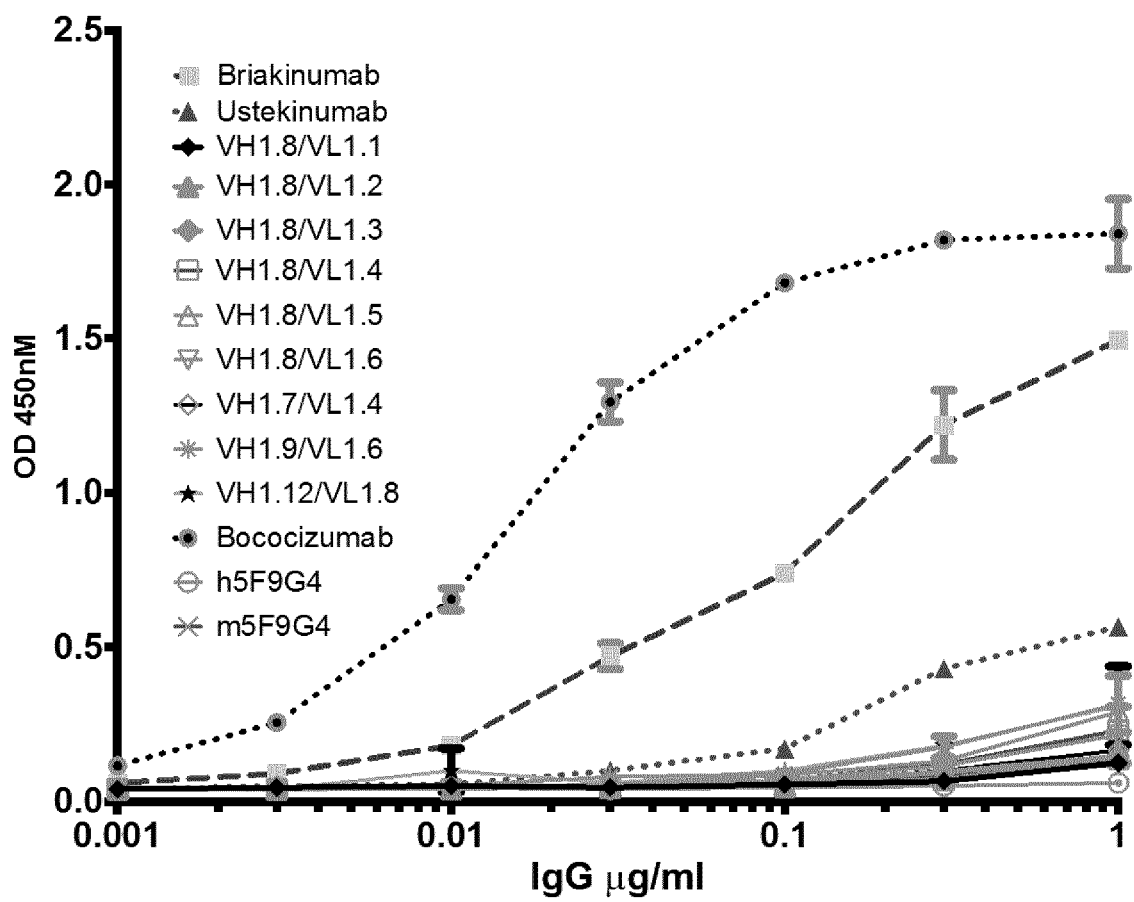
FIG. 11A-FIG. 11C. Development risk ELISAs. This assay showed that designer leads, h5F9G4 and m5F9G4 antibodies in IgG1 form exhibit equivalent or lower binding (with the exception of VH1.12/VL8) to the negatively charged biomolecules Insulin (FIG. 11A), double-stranded DNA (dsDNA) (FIG. 11B) and single-stranded DNA (ssDNA) (FIG. 11C) than the negative control IgG1 Ustekinumab analogue. Strong off-target binding to these molecules, as observed for Bococizumab and Briakinumab analogues has been shown to be a high-risk indicator of poor pharmacokinetics of therapeutic antibodies.
Figure 11B:
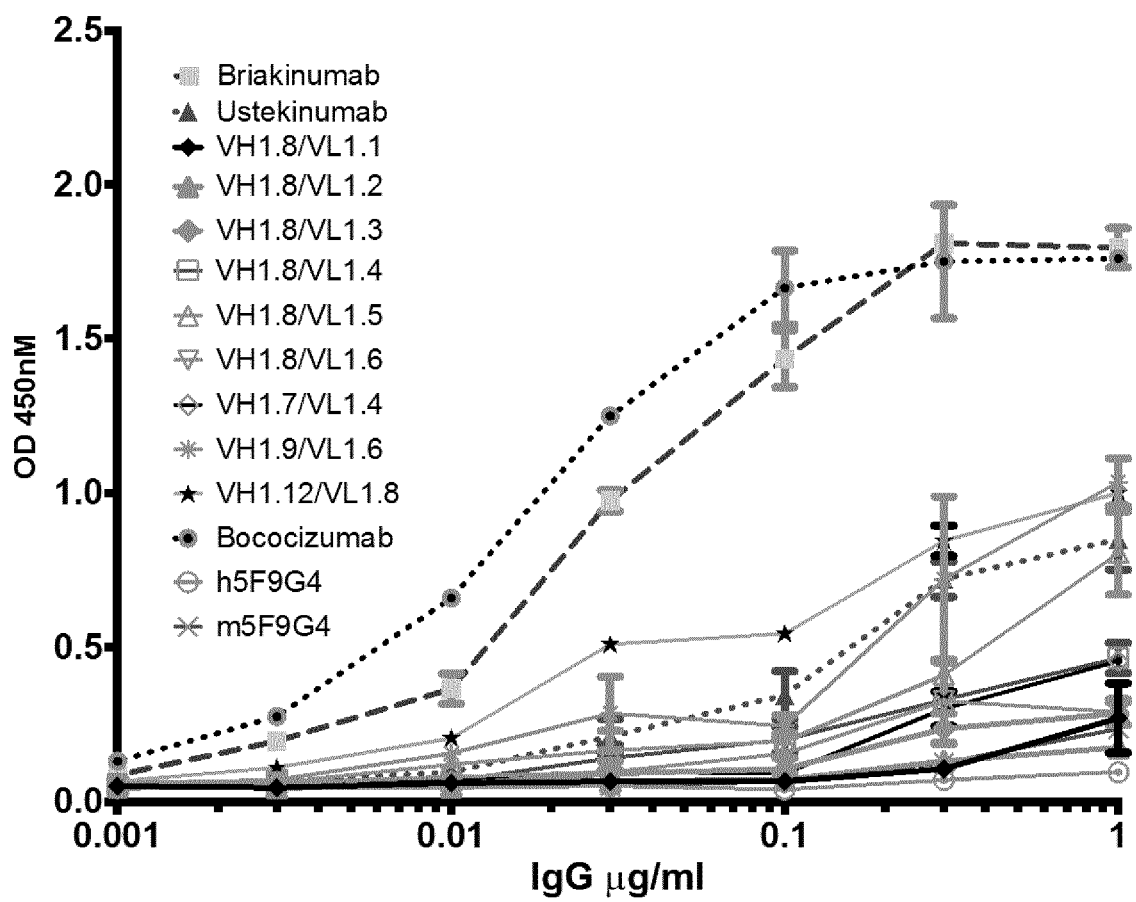
Figure 11C:
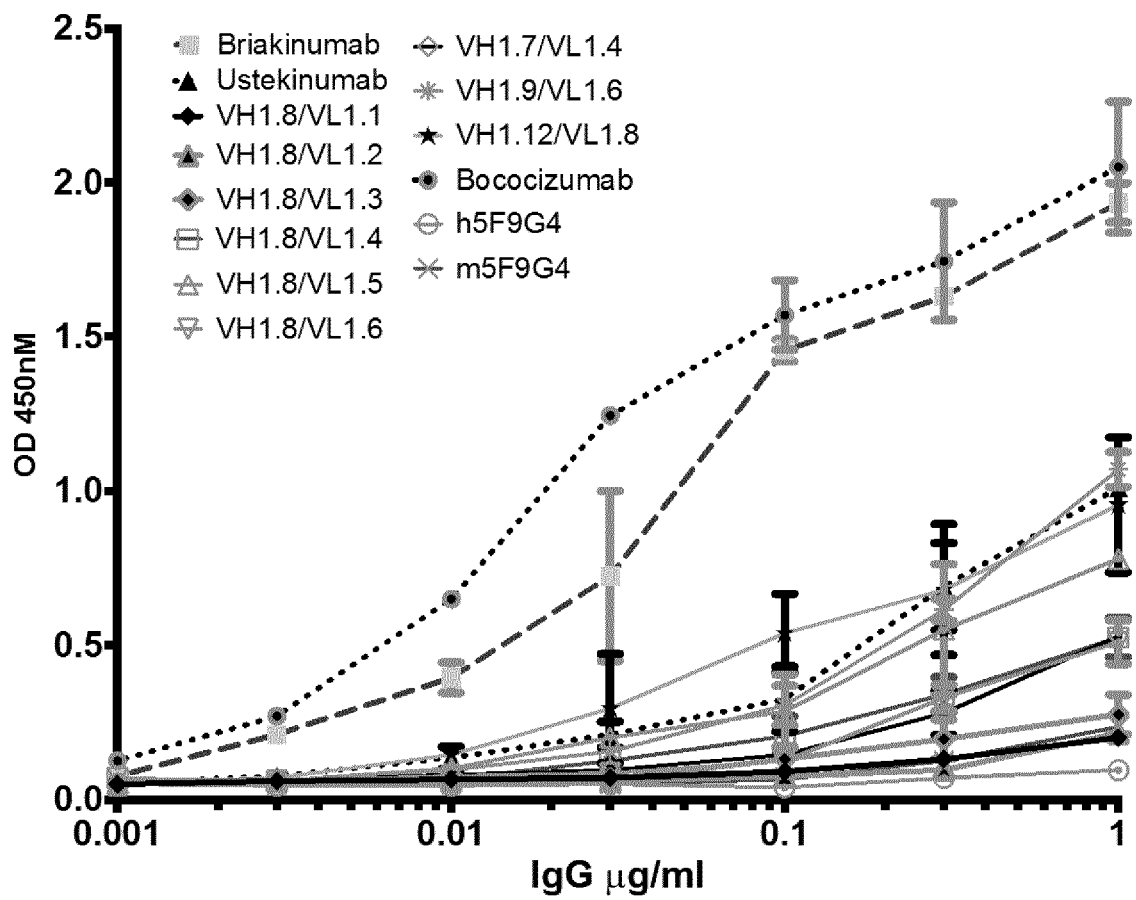

It is known in the art that the binding of IgGs intended for therapeutic use to several indicative biological substrates is an indicator of high risk for poor performance in patients due to poor bioavailability and short in vivo half-life. Three such biological substrates are Insulin, dsDNA and ssDNA (Avery et al. Mabs; 10:2; 244-255; 2018). These three substrates were therefore used to coat ELISA plates and examine the binding of the IgG1null versions of the optimised lead antibodies. Binding signals for these human IgG-based antibodies was compared to 'positive control' human IgG antibodies that have been found to have polyreactivity and poor performance, which stopped their progress in clinical trials (Bococizumab and Briakinumab human IgG1 analogues). For a negative control human IgG1 antibody, an IgG1 Ustekinumab analogue was used as it reacts with the same therapeutic target as Briakinumab, but has longer pK and was successfully approved as a therapeutic product. In the ELISA analyses shown in FIGS. 11A, B and C, the positive control antibodies exhibited the expected strong reactivity to all 3 substrates, while the negative control Ustekinumab showed low reactivity. Importantly, all of the IgG1 lead clones tested showed binding≤the negative control against all 3 substrates. This finding underlined the maintenance of highly specific, target-driven binding in the optimised clones VH1.8/VL1.1, VH1.8/VL1.2, VH1.8/VL1.3, VH1.8/VL1.4, VH1.8/VL1.5, VH1.8/VL1.6, VH1.7NL1.4, VH1.6NL1.9 and VH1.12/VL1.8.

Antibody v-Domain T Cell Epitope Analyses

In silico technologies by the company known as Abzena, Ltd., which are based on identifying the location of T cell epitopes in therapeutic antibodies and proteins, were used for assessing the immunogenicity of both the h5F9G4 and lead antibody v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the immunogenicity assessment tool known under the trademark iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the database known under the trademark TCED™. The sequences were used to interrogate the database known under the trademark TCED™ by BLAST search in order to identify any high sequence homology between peptides (T cell epitopes) from unrelated proteins/antibodies that stimulated T cell responses in previous in vitro T cell epitope mapping studies performed at the company known as Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in the database known under the trademark TCED™), and Germline Epitope ('GE'—human germline peptide sequence with high MHC Class II binding affinity). Germline Epitope 9mer peptides are unlikely to have immunogenic potential due to T cell tolerance (i.e. these peptides are recognised as 'self' in the host), as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic. On the other end of the scale, TCED+ peptides are very high risk for immunogenicity in the clinic, as they have the characteristics of experimentally-proven peptide epitopes that can be presented on MHC molecules and activate human t cells.

Figure 12A:
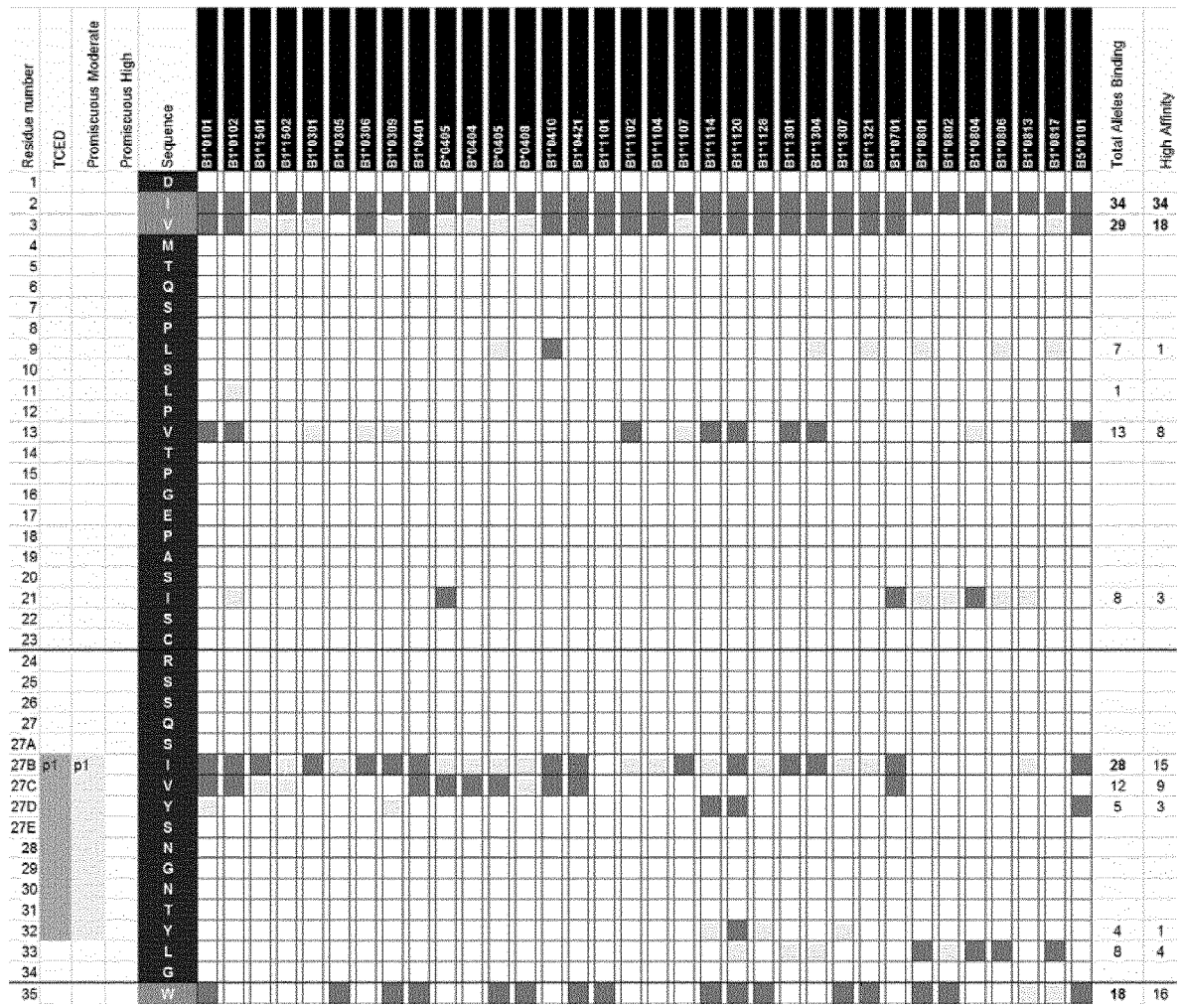
FIG. 12A-FIG. 12C. Summary analysis of the VH and VL sequences of h5F9G4 using immunogenicity assessment tool known under the trademark iTope™. Peptides spanning the full v-domain sequences were tested as 9mer peptides in one amino acid increments. Each row indicates the position of a p1 anchor residue of a 9mer peptide which is scored for MHC class II binding (core 9mer). Each box indicates a binding score of >0.6 between the aligned 9mer and MHC class II. A promiscuous binding peptide is defined as binding 17 or more alleles. Regions containing potentially immunogenic peptides are indicated in 'Promiscuous High' (HAF) and 'Promiscuous Moderate' (LAF) columns; dark grey vertical bars indicate HAF MHC class II binding peptides and light grey vertical bars indicate LAF MHC class II binding peptides. In the 'TCED' column, regions representing closely homologous peptides from the T cell epitope database are shown as vertical grey bars. Example analyses are shown for the key HAF and TCED+ epitopes found in the LCDR1 (SEQ ID NO: 70) (FIG. 12A), HCDR1 (SEQ ID NO: 71) (FIG. 12B) and HCDR3 (SEQ ID NO: 72) (FIG. 12C).

Key lead v-domains exhibited significant beneficial changes in peptide epitope content in comparison to h5F9G4. The v-domain engineering process undertaken here had therefore successfully selected for antibodies that maintained anti-CD47 potency, while removing multiple HAF and LAF epitopes that were TCED+ and found in both the heavy and light chain v-domains of h5F9G4. Importantly, these foreign epitopes were specifically eliminated by germlining mutations found in the CDRs of lead clones. For example, a TCED+ peptide 'IVYSNGNTY' (SEQ ID NO:106) (FIG. 12A) found in the LCDR-1 of h5F9G4 (and, therefore, in any forms of h5F9G4 humanized by CDR grafting) was eliminated in the majority of lead clones by the mutation I>L and V>L at positions 1 and 2, as found in all lead clones in Table 4. This finding illustrated that germlining and non-germlining mutations in the LCDR1 alone are sufficient to remove not only asparagine deamidation risk motifs, but also a proven human T cell epitope.

Figure 12B:
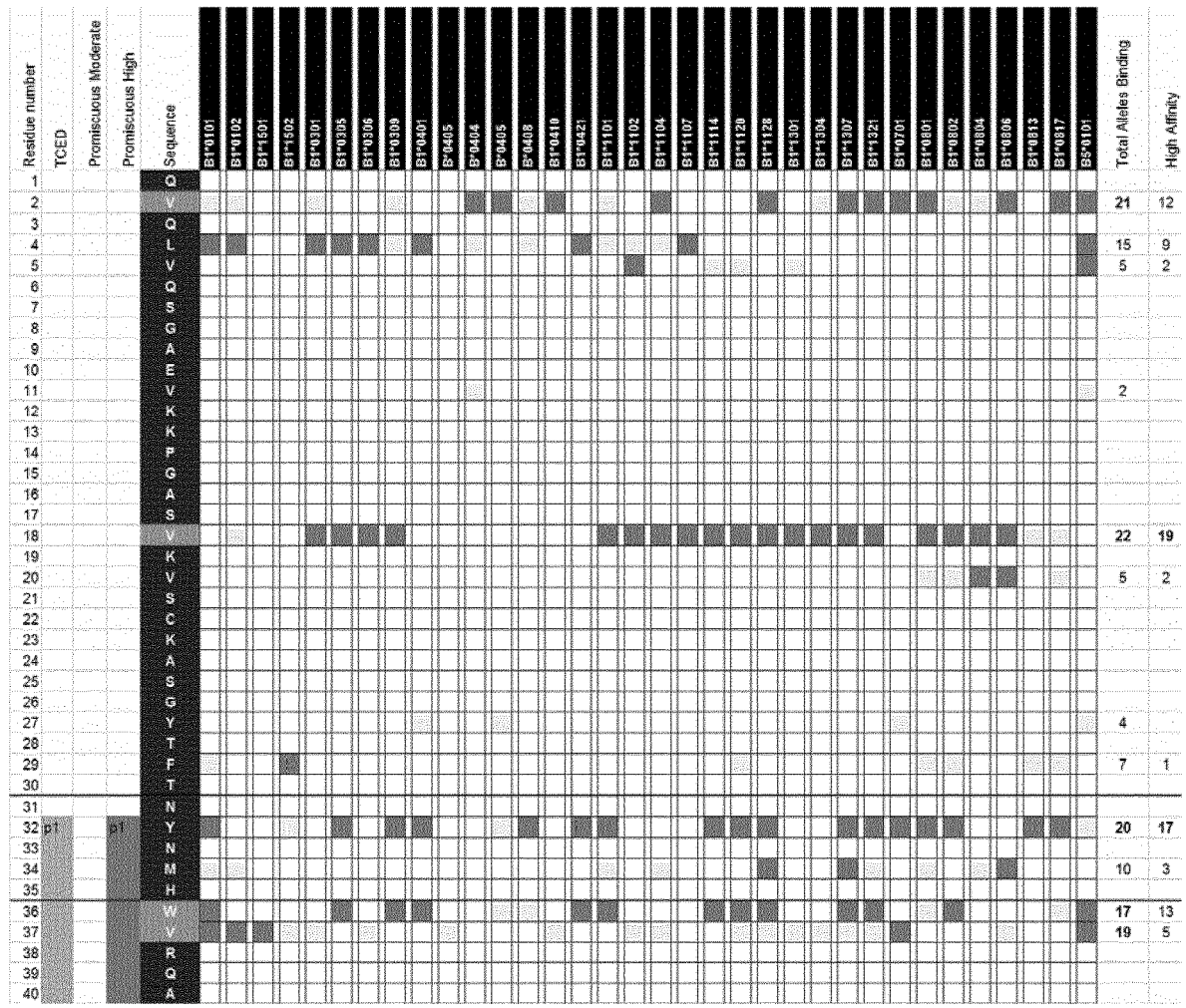

Similarly, the HCDR1/Framework 2 region from the h5F9G4 sequence encoded for a HAF and TCED+ peptide 'YNMHWVRQA' (SEQ ID NO:107) (FIG. 12B). This epitope was ablated in a number of lead sequences found in Table 4, such as antibodies containing the sequence 'YAMHWVRQA' (SEQ ID NO:108) (e.g. VH1.1, VH1.6, VH1.8, VH1.9, VH1.11, VH1.12), or 'YNIHWVRQA' (SEQ ID NO:109) (e.g. VH1.7). Importantly, the mutations N>A at position 2 and M>I at position 3 not only ablated the TCED+ epitope, but converted this epitope into GE peptides. In addition, the germlining of the last residues of the HCDR2 of all leads described in Table 4 (mutation D>G at the final c-terminal HCDR2 position as defined in Table 2), also reinstated GE peptides that are found in the germlines of both IGHV5-51 ('FQGQVTISA' SEQ ID NO:102) and IGHV1-3 ('FQGRVTITA' SEQ ID NO:103).

Figure 12C:
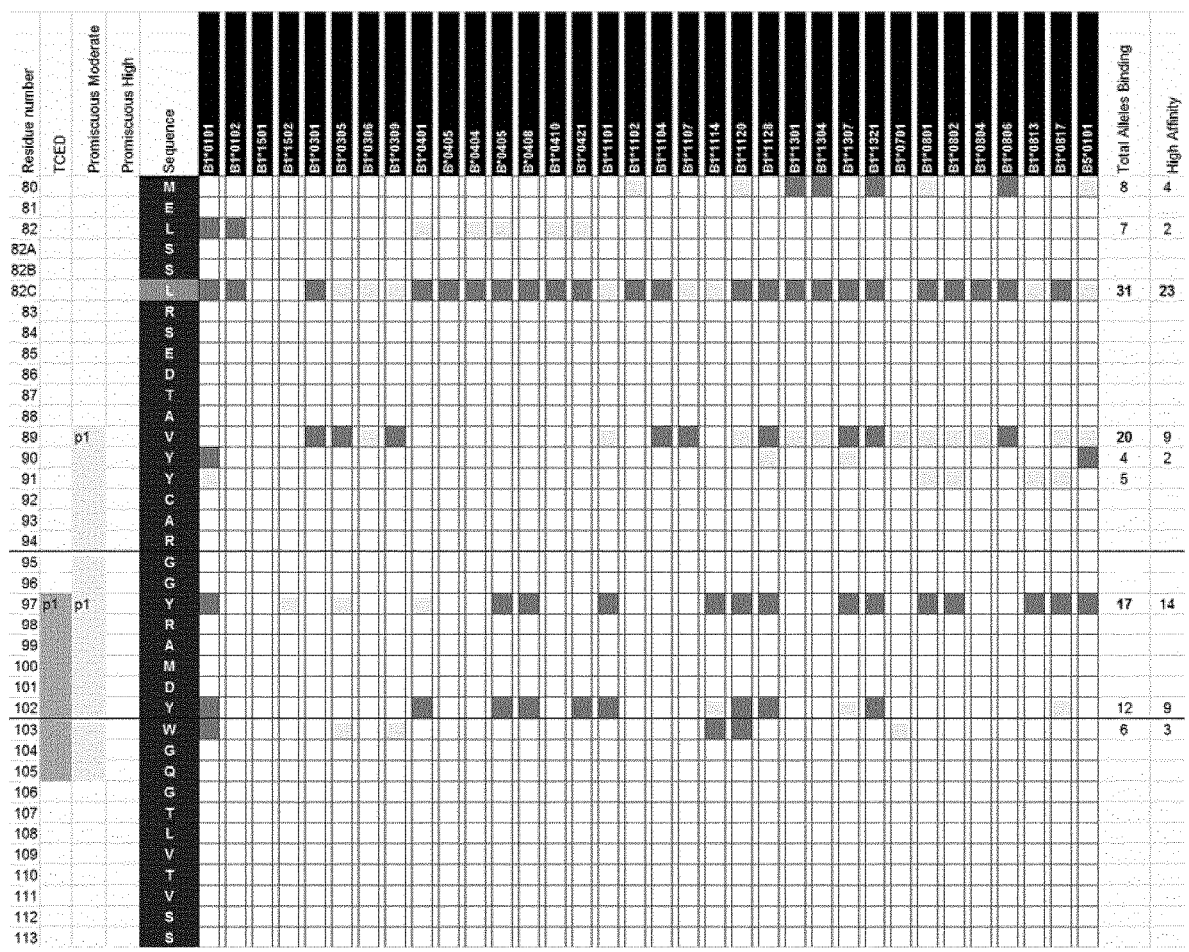

In the HCDR3/Framework 4 sequence of h5F9G4 VH domain, a further TCED+ peptide 'YRAMDYWGQ' (SEQ ID NO:110) was identified (FIG. 12C). This epitope was ablated in a number of lead sequences found in Table 4, such as antibodies containing the sequence 'YRAEDYWGQ' (SEQ ID NO:111) (e.g. VH1.1, VH1.2, VH1.3, VH1.6, VH1.9).

Critically, non-germline and germline mutations that were predicted not to be tolerated in CD47-binding clones according to the data in FIGS. 2A and 2B were included in several key leads, as exploratory, novel substitutions. For example, in the LCDR-1 of h5F9G4 the development risk motif-removing mutations found in light chain sequences VL1.3, VL 1.4, VL 1.5 and VL 1.6 (Table 4) should not be tolerated (FIG. 2B). Similarly, the single, deimmunising, non-conservative, N>A mutation in the HCDR1 of clones based on the VH1.8 sequence and others (Table 4) was strongly predicted to be not tolerated in the data of FIG. 2A). These findings illustrate that beneficial mutations are contextual, v-gene framework-dependent and in this case could not be fully predicted either a priori, or by the method of Townsend et al.

Figure 13A:
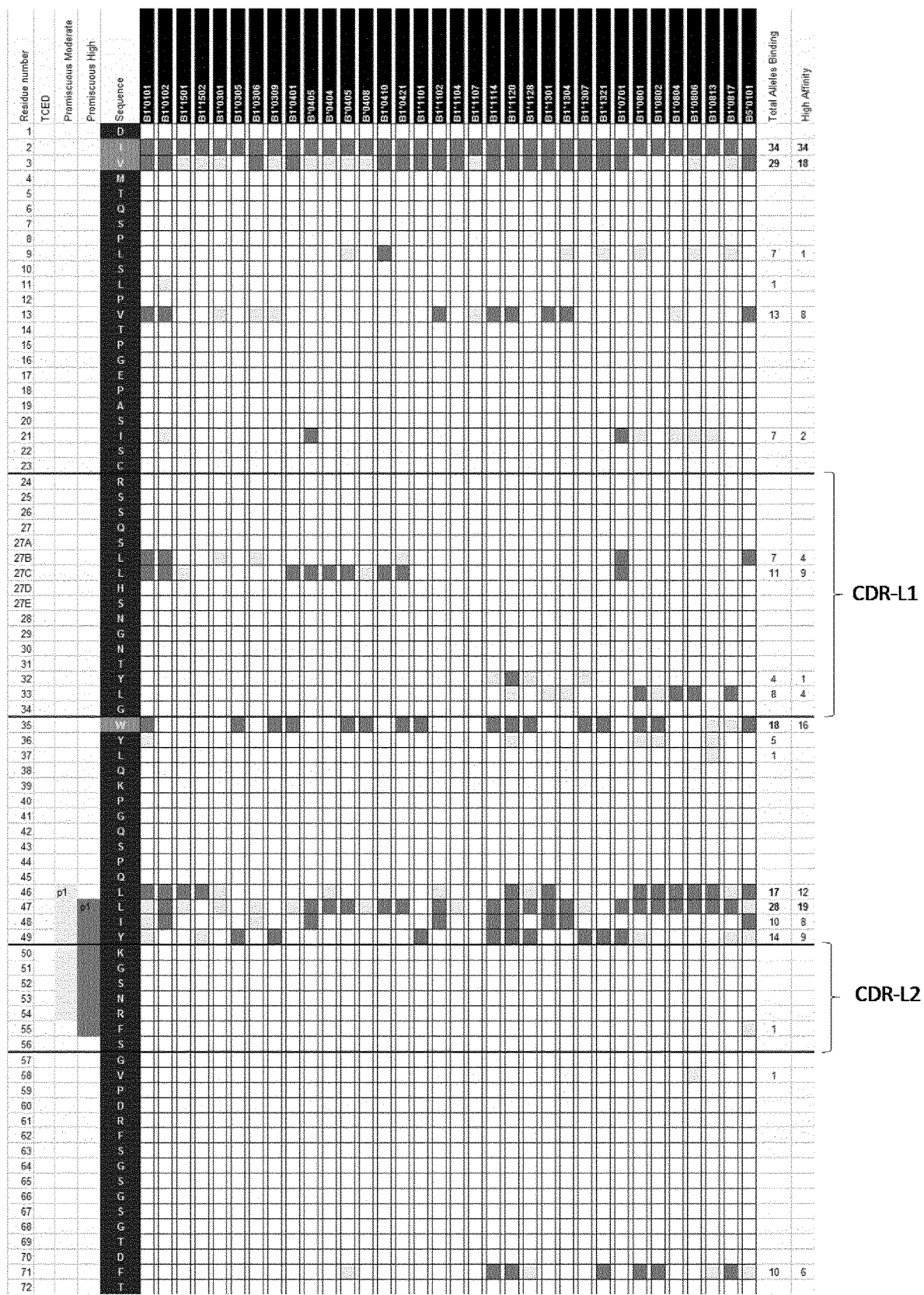
FIG. 13A-FIG. 13B. Summary analysis of the VL sequences of key leads using immunogenicity assessment tool known under the trademark iTope™. Peptides spanning the full v-domain sequences were tested as 9mer peptides in one amino acid increments across the full v-domains (VL1.1 shown here as an example). Data is represented as in FIG. 13A-FIG. 13B. Example analyses are shown for the key HAF and TCED+ epitopes found in the LCDR2 (SEQ ID NO: 73) (FIG. 13A) and LCDR3 (SEQ ID NO: 74) (FIG. 13B).
Figure 13B:
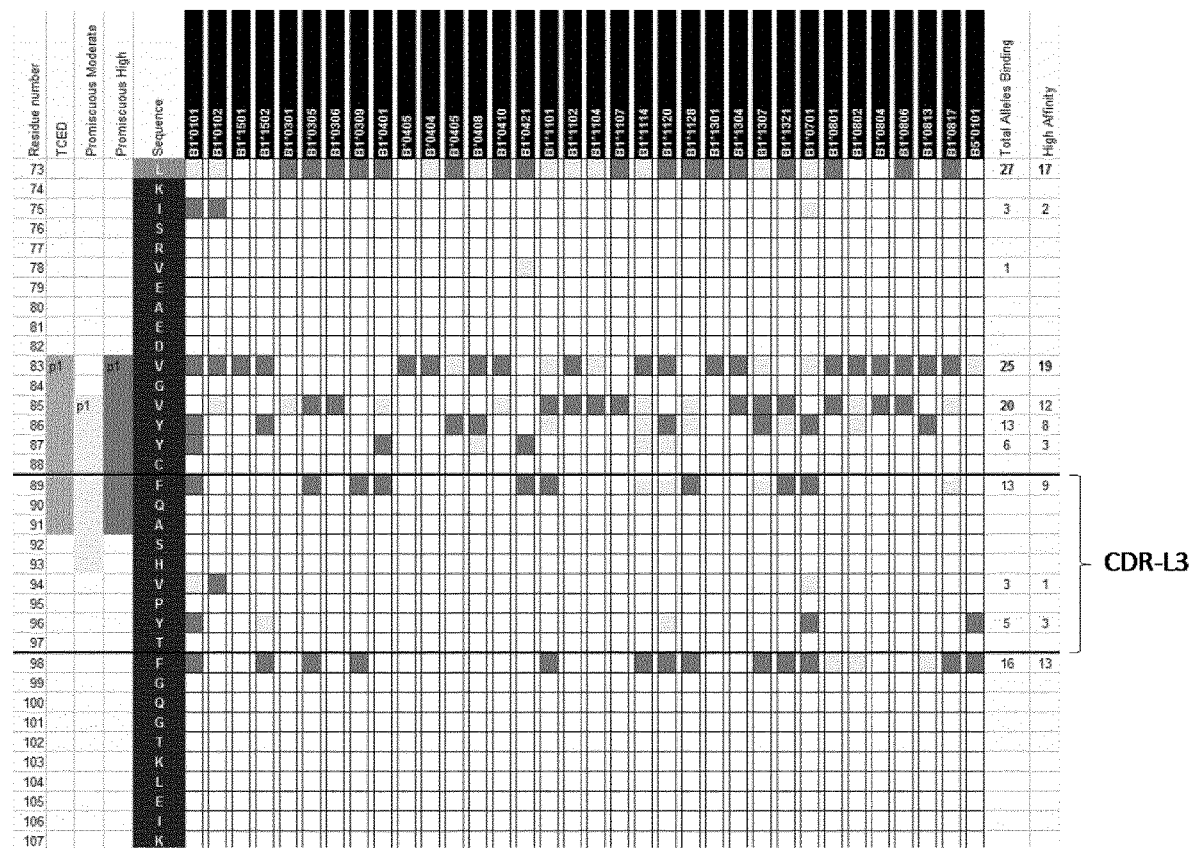

Finally, two remaining HAF peptides were found in the VL sequences VL1.1-1.9. The first HAF peptide 'LIYKGSNRF' (SEQ ID NO:112), spanning the Framework2/LCDR2 regions was identified in the analysis shown in FIG. 13A. The second HAF peptide 'VGVYYCFQA' (SEQ ID NO:113), spanning the Framework3/LCDR3 regions was identified in the analysis shown in FIG. 13A. Both HAF peptides could be fully ablated by mutation of the residues at position 1 to alanine (L>A and V>A, respectively). To sample these substitutions, a new clone 'VH1.8/VL1.6-DI' was constructed, containing both alanine substitutions in the VL domain.

Potency and Affinity Analyses of Key Leads

Clones h5F9G4, VH1.8/VL1.1, VH1.8/VL1.6, and VH1.8/VL1.6-DI were readily expressed and purified in the human IgG4(S228P) format. For all clones the Fab domains were also expressed as soluble monomers and purified for binding affinity analyses. These Fabs were then examined for affinity to human and cyno CD47 by a biosensor system sold under the trademark Biacore® using steady state affinity analysis. Steady state was used as the binding affinity analysis as the on and off rates of all Fabs were too fast for reliable 1:1 modelling. As shown in Table 6, all 4 clones exhibited accurate, well-fitted data, as evidenced by very low Chi2 values. All clones were found to have binding affinities in the low nM range, within 2-fold of h5F9G4.

Figure 14A:
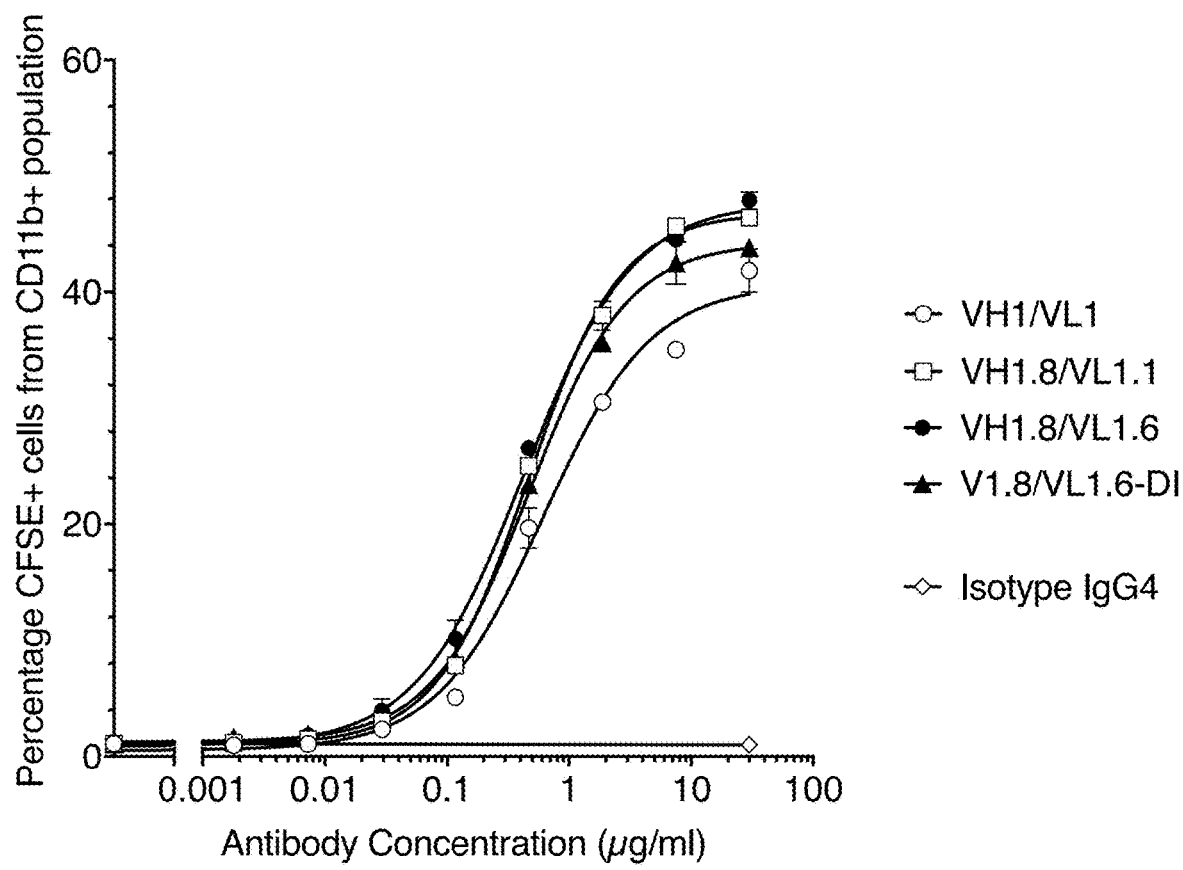
FIG. 14A-FIG. 14C. Phagocytosis potency assays using human macrophage and Jurkat cells. Clones h5F9G4, VH1.8/VL1.1, VH1.8/VL1.6, and VH1.8/VL1.6-DI in IgG4 (S228P) format were examined for their relative potencies in a flow cytometric assay of phagocytosis, using human monocyte-derived macrophages derived from 3 separate donors and Jurkat human cancer cells as the CD47+ target cells. Phagocytosis was measured as Percentage CFSE+ cells from CD11b+ population for Donors 1 (FIG. 14A), 2 (FIG. 14B) and 3 (FIG. 14C).
Figure 14B:
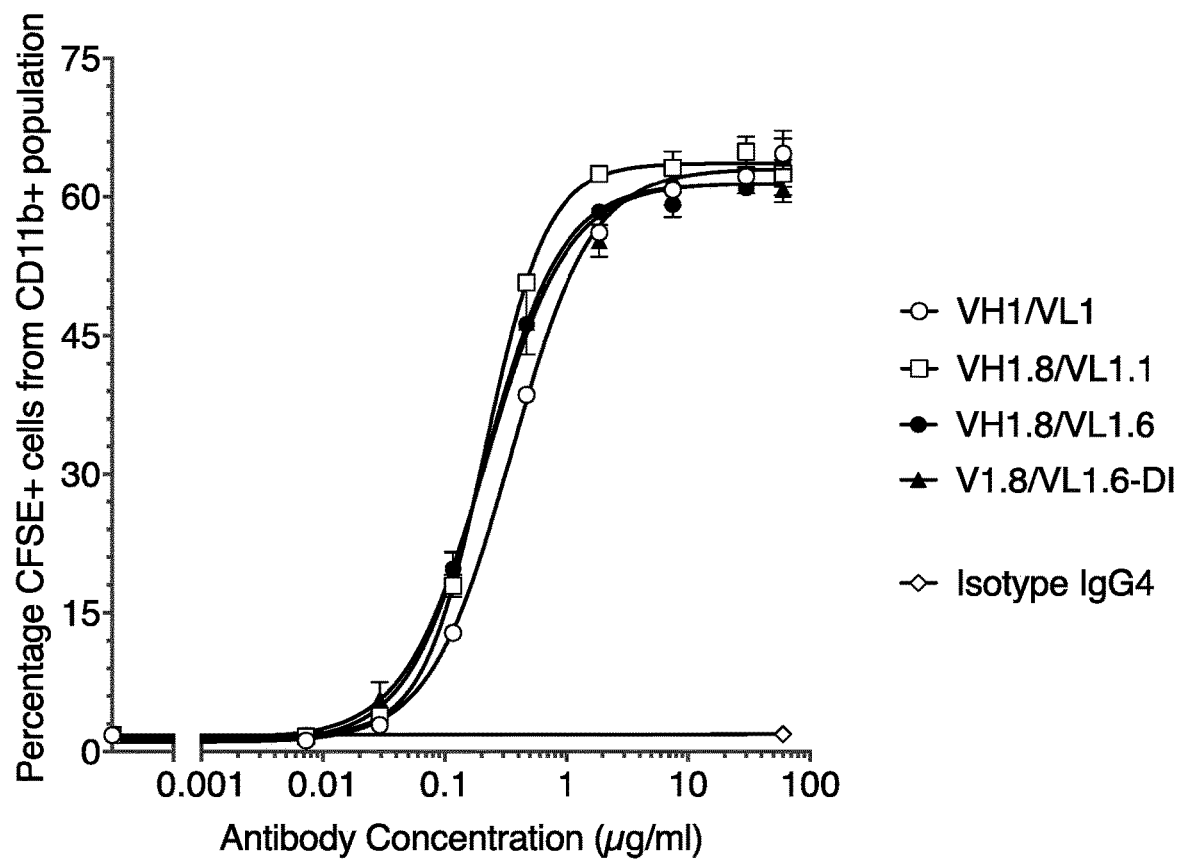
Figure 14C:
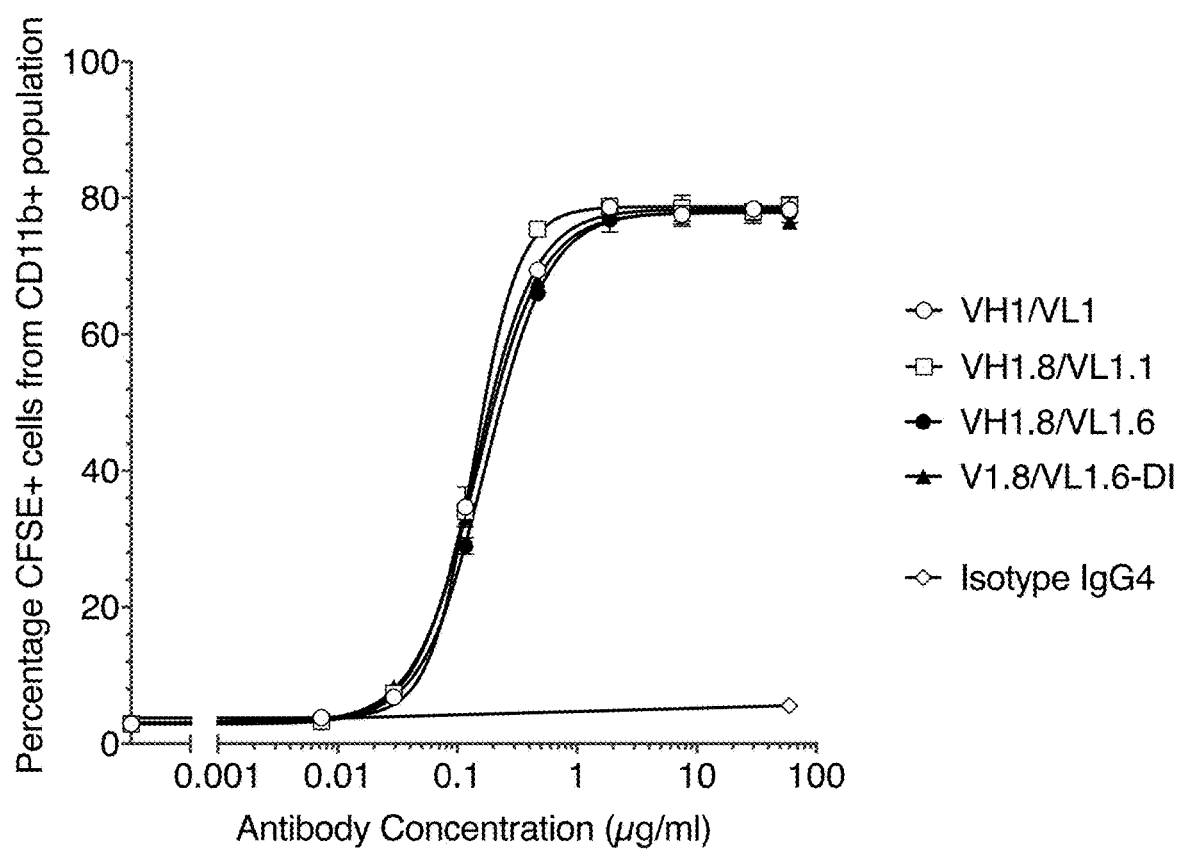

As final analysis of retained potency, clones h5F9G4, VH1.8/VL1.1, VH1.8/VL1.6, and VH1.8/VL1.6-DI in IgG4 (S228P) format were examined for their relative potencies in a flow cytometric assay of phagocytosis, using human monocyte-derived macrophages derived from 3 separate donors and Jurkat human cancer cells as the CD47+ target cells. For all clones analysed against cells from Donor 1 (FIG. 14A), Donor 2 (FIG. 14B) and Donor 3 (FIG. 14C), all clones had fully retained or improved over the potency of h5F9G4, as evidenced by fully overlapping response curves.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

No limitation with respect to the specific embodiments disclosed herein and set forth in the appended claims is intended nor should any be inferred. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

TABLE 1

Amino acid sequences murine anti-CD47 CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GYTFTNYNMH (SEQ ID NO: 114) | MGTIYPGNDDTSYNQKFKD (SEQ ID NO: 119) | GGYRAMDY (SEQ ID NO: 126) | RSSQSIVYSNGNTYLG (SEQ ID NO: 130) | KVSNRFS (SEQ ID NO: 134) | FQGSHVPYT (SEQ ID NO: 136) |
| Kabat | NYNMH (SEQ ID NO: 115) | TIYPGNDDTSYNQKFKD (SEQ ID NO: 120) | GGYRAMDY (SEQ ID NO: 126) | RSSQSIVYSNGNTYLG (SEQ ID NO: 130) | KVSNRFS (SEQ ID NO: 134) | FQGSHVPYT (SEQ ID NO: 136) |
| Chotia | GYTFTNY (SEQ ID NO: 116) | YPGNDD (SEQ ID NO: 121) | GGYRAMDY (SEQ ID NO: 126) | RSSQSIVYSNGNTYLG (SEQ ID NO: 130) | KVSNRFS (SEQ ID NO: 134) | FQGSHVPYT (SEQ ID NO: 136) |
| IMGT | GYTFTNYN (SEQ ID NO: 117) | IYPGNDDT (SEQ ID NO: 122) | ARGGYRAMDY (SEQ ID NO: 127) | QSIVYSNGNTY (SEQ ID NO: 131) | KVS | FQGSHVPYT (SEQ ID NO: 136) |
| AHo | GYTFTNYNMH (SEQ ID NO: 114) | IYPGNDDTSYNQKFKD (SEQ ID NO: 123) | GGYRAMD (SEQ ID NO: 128) | SSQSIVYSNGNTY (SEQ ID NO: 132) | KVSNRFS (SEQ ID NO: 134) | GSHVPY (SEQ ID NO: 137) |

TABLE 1-continued

Amino acid sequences murine anti-CD47 CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| AbM | GYTFTNYN MH (SEQ ID NO: 114) | TIYPGNDDTS (SEQ ID NO: 124) | GGYRAMDY (SEQ ID NO: 126) | RSSQSIVYSNGNTYLG (SEQ ID NO: 130) | KVSNRFS (SEQ ID NO: 134) | FQGSHVPY T (SEQ ID NO: 136) |
| Contact | TNYNMH (SEQ ID NO: 118) | MGTIYPGNDDTS (SEQ ID NO: 125) | ARGGYRAM D (SEQ ID NO: 129) | VYSNGNTYLGWY (SEQ ID NO: 133) | ALIYKVSN RF (SEQ ID NO: 135) | FQGSHVPY (SEQ ID NO: 138) |

TABLE 2

Amino acid sequence of 5F9G4 murine anti-CD47 v-domains (m5F9G4) and human germline CDR grafts (h5F9G4).

| V DOMAIN | Human germline[1] | Amino acid sequence[2] |
|---|---|---|
| m5F9G4-VH | na | QVQLQQPGAELVKPGASVMM SCKASGYTFTNYNMHWVKQT PGQGLEWIGTIYPGNDDTSY NQKFKDKATLTADKSSSAAY MQLSSLTSEDSAVYYCARGG YRAMDYWGQGTSVTVSS (SEQ ID NO: 139) |
| h5F9G4-VH | IGHV1-3 | QVQLVQSGAEVKKPGASVKV SCKASGYTFTNYNMHWVRQA PGQRLEWMGTIYPGNDDTSY NQKFKDRVTITADTSASTAY MELSSLRSEDTAVYYCARGG YRAMDYWGQGTLVTVSS (SEQ ID NO: 140) |
| VH graft | IGHV5-51[3] | EVQLVQSGAEVKKPGESLKI SCKGSGYSFTNYNMHWVRQM PGKGLEWMGTIYPGNDDTSY NQKFQGQVTISADKSISTAY LQWSSLKASDTAMYYCARGG YRAMDYWGQGTLVTVSS (SEQ ID NO: 141) |
| m5F9G4-VL | na | DVLMTQTPLSLPVSLGDQAS ISCRSSQSIVYSNGNTYLGW YLQKPGQSPKLLIYKVSNRF SGVPDRFSGSGSGTDFTLKI SRVEAEDLGVYHCFQGSHVP YTFGGGTKVEIK (SEQ ID NO: 142) |
| h5F9G4-VL | IGKV2-28 | DIVMTQSPLSLPVTPGEPAS ISCRSSQSIVYSNGNTYLGW YLQKPGQSPQLLIYKVSNRF SGVPDRFSGSGSGTDFTLKI SRVEAEDVGVYYCFQGSHVP YTFGQGTKLEIK (SEQ ID NO: 143) |
| VL graft | IGKV2-28[3] | DIVMTQSPLSLPVTPGEPAS ISCRSSQSIVYSNGNTYLGW YLQKPGQSPQLLIYKVSNRF SGVPDRFSGSGSGTDFTLKI SRVEAEDVGVYYCFQGSHVP YTFGQGTKLEIK (SEQ ID NO: 144) |

[1] Human germline definitions used for grafting, based on IMGT system.
[2] CDR residues are in bold and underlined. As noted above, the "Unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.
[3] Grafts are fully germline in the framework regions, used as the template for CDR mutant library construction.

TABLE 3

Amino acid sequences of unique CDRs from 269 unique anti-CD47 v-domains in the IGKV2-28/IGHV5-51 background.

| LCDR1 | LCDR2 | LCDR3 | HCDR1 | HCDR2 | HCDR2 | HCDR2 | HCDR3 |
|---|---|---|---|---|---|---|---|
| RSSQSLLH SGGNTYLD (SEQ ID NO: 145) | KGSNRFS (SEQ ID NO: 52) | FQALHVPYT (SEQ ID NO: 165) | GYSFTNYNIG (SEQ ID NO: 195) | IGTIYPGDDD TRYNPKFQG (SEQ ID NO: 200) | MGTIYPGDDD TSYSQKFQG (SEQ ID NO: 232) | MGTIYPGNDD TSYNQSFQG (SEQ ID NO: 262) | GGARAMDY (SEQ ID NO: 289) |
| RSSQSLLH SGGNTYLG (SEQ ID NO: 146) | KVSNRAS (SEQ ID NO: 163) | FQAMQTPYT (SEQ ID NO: 166) | GYSFTNYNIH (SEQ ID NO: 57) | MGIIYPGDDD TRYNPKFQG (SEQ ID NO: 201) | MGTIYPGDGD TSYNPSFQG (SEQ ID NO: 233) | MGTIYPGDDD TSYSPKFQG (SEQ ID NO: 263) | GGCRALDY (SEQ ID NO: 290) |
| RSSQSLLH SGYNTYLG (SEQ ID NO: 147) | KVSNRSS (SEQ ID NO: 164) | FQASHIPYT (SEQ ID NO: 167) | GYSFTNYNMH (SEQ ID NO: 196) | MGIIYPGDDD TRYNPSFQG (SEQ ID NO: 202) | MGTIYPGDND TSYNPSFQG (SEQ ID NO: 234) | MGTIYPGNDD TSYSPRFQG (SEQ ID NO: 264) | GGCRAMDY (SEQ ID NO: 291) |

TABLE 3-continued

Amino acid sequences of unique CDRs from 269 unique anti-CD47 v-domains in the IGKV2-28/IGHV5-51 background.

| LCDR1 | LCDR2 | LCDR3 | HCDR1 | HCDR2 | HCDR2 | HCDR2 | HCDR3 |
|---|---|---|---|---|---|---|---|
| RSSQSLLH SNGNTYLD (SEQ ID NO: 148) | | FQASHTPYT (SEQ ID NO: 168) | GYSFTNYSIH (SEQ ID NO: 197) | MGIIYPGDDD TSYNPKFQG (SEQ ID NO: 203) | MGTIYPGDSD TKYNPKFQG (SEQ ID NO: 235) | MGTIYPGNDD TSYSPSFQG (SEQ ID NO: 265) | GGCRAMGY (SEQ ID NO: 292) |
| RSSQSLLH SNGNTYLG (SEQ ID NO: 51) | | FQASHVPYT (SEQ ID NO: 53) | GYSFTSYNIH (SEQ ID NO: 198) | MGIIYPGDDD TSYNQKFQG (SEQ ID NO: 204) | MGTIYPGDSD TRYNPKFQG (SEQ ID NO: 58) | MGTIYPGNDD TSYSQKFQG (SEQ ID NO: 90) | GGDRAMDY (SEQ ID NO: 293) |
| RSSQSLLH SNYNTYLG (SEQ ID NO: 149) | | FQASQIPYT (SEQ ID NO: 169) | GYSFTSYNMH (SEQ ID NO: 199) | MGIIYPGDSD TRYNPKFQG (SEQ ID NO: 205) | MGTIYPGDSD TRYNPSFQG (SEQ ID NO: 236) | MGTIYPGNDD TSYSQSFQG (SEQ ID NO: 266) | GGERAMDY (SEQ ID NO: 294) |
| RSSQSLLQ SNGNTYLG (SEQ ID NO: 150) | | FQASQTPYT (SEQ ID NO: 170) | | MGIIYPGDSD TRYNPSFQG (SEQ ID NO: 206) | MGTIYPGDSD TRYNQKFQG (SEQ ID NO: 98) | MGTIYPGNDG TRYNQKFQG (SEQ ID NO: 267) | GGFRAEDY (SEQ ID NO: 295) |
| RSSQSLLY SGGNTYLG (SEQ ID NO: 151) | | FQASQVPYT (SEQ ID NO: 54) | | MGIIYPGDSD TRYNQKFQG (SEQ ID NO: 207) | MGTIYPGDSD TRYSPKFQG (SEQ ID NO: 237) | MGTIYPGNGD TSYNHKFQG (SEQ ID NO: 268) | GGFRAMDY (SEQ ID NO: 50) |
| RSSQSLLY SNGNTYLG (SEQ ID NO: 152) | | FQASRVPYT (SEQ ID NO: 171) | | MGIIYPGDSD TSYNQSFQG (SEQ ID NO: 208) | MGTIYPGDSD TRYSPRFQG (SEQ ID NO: 238) | MGTIYPGNGD TSYNQKFQG (SEQ ID NO: 269) | GGFRAQDY (SEQ ID NO: 296) |
| RSSQSLVH SGGNTYLG (SEQ ID NO: 153) | | FQATQVPYT (SEQ ID NO: 172) | | MGIIYPGNDD TRYNPKFQG (SEQ ID NO: 209) | MGTIYPGDSD TRYSPSFQG (SEQ ID NO: 239) | MGTIYPGNND TSYNPKFQG (SEQ ID NO: 270) | GGGRAMDY (SEQ ID NO: 297) |
| RSSQSLVH SGYNTYLG (SEQ ID NO: 154) | | FQGLQVPYT (SEQ ID NO: 173) | | MGIIYPGNDD TRYNPSFQG (SEQ ID NO: 210) | MGTIYPGDSD TRYSQKFQG (SEQ ID NO: 240) | MGTIYPGNSD TRYNHSFQG (SEQ ID NO: 271) | GGHRAEDY (SEQ ID NO: 298) |
| RSSQSLVH SNGNTYLD (SEQ ID NO: 155) | | FQGSHIPYT (SEQ ID NO: 174) | | MGIIYPGNDD TRYNQKFQG (SEQ ID NO: 211) | MGTIYPGDSD TRYSQSFQG (SEQ ID NO: 241) | MGTIYPGNSD TRYNPKFQG (SEQ ID NO: 101) | GGHRAMDY (SEQ ID NO: 299) |
| RSSQSLVH SNGNTYLG (SEQ ID NO: 156) | | FQGSHTPYT (SEQ ID NO: 175) | | MGIIYPGNSD TRYNPKFQG (SEQ ID NO: 212) | MGTIYPGDSD TSYNHKFQG (SEQ ID NO: 242) | MGTIYPGNSD TRYNPSFQG (SEQ ID NO: 272) | GGIRAMDY (SEQ ID NO: 99) |
| RSSQSLVH SNGQTYLG (SEQ ID NO: 157) | | FQGSHVPYI (SEQ ID NO: 100) | | MGIIYPGNSD TRYNPSFQG (SEQ ID NO: 213) | MGTIYPGDSD TSYNPKFHG (SEQ ID NO: 243) | MGTIYPGNSD TRYNQKFQG (SEQ ID NO: 273) | GGKRAMDY (SEQ ID NO: 93) |
| RSSQSLVH SNYNTYLG (SEQ ID NO: 158) | | FQGSQTPYT (SEQ ID NO: 176) | | MGIIYPGNSD TRYNQKFQG (SEQ ID NO: 214) | MGTIYPGDSD TSYNPKFQG (SEQ ID NO: 94) | MGTIYPGNSD TRYNQSFQG (SEQ ID NO: 274) | GGLRAMDY (SEQ ID NO: 300) |
| RSSQSLVH SSGNTYLG (SEQ ID NO: 159) | | FQGSQVPYT (SEQ ID NO: 177) | | MGIIYPGNSD TRYNQRFQG (SEQ ID NO: 215) | MGTIYPGDSD TSYSPKFQG (SEQ ID NO: 244) | MGTIYPGNSD TRYSPRFQG (SEQ ID NO: 275) | GGLRTMDY (SEQ ID NO: 301) |
| RSSQSLVQ SNGNTYLG (SEQ ID NO: 160) | | LQGSHIPYT (SEQ ID NO: 178) | | MGIIYPGNSD TRYNQSFQG (SEQ ID NO: 216) | MGTIYPGDSD TSYNPSFQG (SEQ ID NO: 245) | MGTIYPGNSD TRYSPSFQG (SEQ ID NO: 276) | GGMRAMDY (SEQ ID NO: 302) |
| RSSQSLVY SNGNTYLG (SEQ ID NO: 161) | | LQGSHTPYT (SEQ ID NO: 179) | | MGIIYPGNSD TRYSPKFQG (SEQ ID NO: 217) | MGTIYPGDSD TSYNQKFQG (SEQ ID NO: 246) | MGTIYPGNSD TRYSQKFQG (SEQ ID NO: 277) | GGNRAKDY (SEQ ID NO: 303) |

TABLE 3-continued

Amino acid sequences of unique CDRs from 269 unique anti-CD47 v-domains in the IGKV2-28/IGHV5-51 background.

| LCDR1 | LCDR2 | LCDR3 | HCDR1 | HCDR2 | HCDR2 | HCDR2 | HCDR3 |
|---|---|---|---|---|---|---|---|
| RSSQSLVY SNYNTYLG (SEQ ID NO: 162) | | LQGSHVPYT (SEQ ID NO: 180) | | MGIIYPGNSD TRYSPSFQG (SEQ ID NO: 218) | MGTIYPGDSD TSYNQSFQG (SEQ ID NO: 247) | MGTIYPGNSD TSYNPKFQG (SEQ ID NO: 92) | GGNRAMDY (SEQ ID NO: 304) |
| | | LQGSQTPYT (SEQ ID NO: 181) | | MGIIYPGNSD TSYNPKFQG (SEQ ID NO: 219) | MGTIYPGDSD TSYSPKFQG (SEQ ID NO: 248) | MGTIYPGNSD TSYNPRFQG (SEQ ID NO: 278) | GGQRAMDY (SEQ ID NO: 305) |
| | | LQGSQVPYT (SEQ ID NO: 182) | | MGIIYPGNSD TSYNPRFQG (SEQ ID NO: 220) | MGTIYPGDSD TSYSPSFQG (SEQ ID NO: 249) | MGTIYPGNSD TSYNPSFQG (SEQ ID NO: 61) | GGRRAMDY (SEQ ID NO: 306) |
| | | MQALQVPYT (SEQ ID NO: 183) | | MGIIYPGNSD TSYNPSFQG (SEQ ID NO: 221) | MGTIYPGDSD TSYSQKFQG (SEQ ID NO: 250) | MGTIYPGNSD TSYNQKFQG (SEQ ID NO: 279) | GGSRAKDY (SEQ ID NO: 307) |
| | | MQASHIPYT (SEQ ID NO: 184) | | MGIIYPGNSD TSYNQKFQG (SEQ ID NO: 222) | MGTIYPGNDD TKYSPKFQG (SEQ ID NO: 251) | MGTIYPGNSD TSYNQSFQG (SEQ ID NO: 280) | GGSRAMDY (SEQ ID NO: 308) |
| | | MQASHTPYT (SEQ ID NO: 185) | | MGIIYPGNSD TSYSPKFQG (SEQ ID NO: 223) | MGTIYPGNDD TRYNPKFQG (SEQ ID NO: 252) | MGTIYPGNSD TSYSPKFQG (SEQ ID NO: 281) | GGTRAMDY (SEQ ID NO: 309) |
| | | MQASHVPYT (SEQ ID NO: 96) | | MGTIYPGDDD TRYNPKFQG (SEQ ID NO: 224) | MGTIYPGNDD TRYNPSFQG (SEQ ID NO: 253) | MGTIYPGNSD TSYSPSFQG (SEQ ID NO: 282) | GGVRAMDY (SEQ ID NO: 62) |
| | | MQASQIPYT (SEQ ID NO: 186) | | MGTIYPGDDD TRYNPSFQG (SEQ ID NO: 225) | MGTIYPGNDD TRYSQKFQG (SEQ ID NO: 254) | MGTIYPGNSD TSYSQKFQG (SEQ ID NO: 283) | GGVRATDY (SEQ ID NO: 310) |
| | | MQASQTPYT (SEQ ID NO: 187) | | MGTIYPGDDD TRYNQKFQG (SEQ ID NO: 226) | MGTIYPGNDD TRYNQSFQG (SEQ ID NO: 255) | MGTIYSGNSD TSYSPSFQG (SEQ ID NO: 284) | GGWRAMDY (SEQ ID NO: 311) |
| | | MQASQVPYT (SEQ ID NO: 63) | | MGTIYPGDDD TRYNQNFQG (SEQ ID NO: 227) | MGTIYPGNDD TRYSPKFQG (SEQ ID NO: 256) | MGTIYPGNDD TRYSQSFQG (SEQ ID NO: 285) | GGYHAMDY (SEQ ID NO: 312) |
| | | MQGLHVPYT (SEQ ID NO: 188) | | MGTIYPGDDD TRYNQSFQG (SEQ ID NO: 228) | MGTIYPGNDD TRYSPSFQG (SEQ ID NO: 257) | MGTIYPGNDD TSYNHKFQG (SEQ ID NO: 286) | GGYKAMDY (SEQ ID NO: 313) |
| | | MQGLQVPYT (SEQ ID NO: 189) | | MGTIYPGDDD TRYSPKFQG (SEQ ID NO: 229) | MGTIYPGNDD TRYSQKFQG (SEQ ID NO: 258) | MGTIYPGNDD TSYNPKFQG (SEQ ID NO: 287) | GGYRAADY (SEQ ID NO: 314) |
| | | MQGSHIPYT (SEQ ID NO: 190) | | MGTIYPGDDD TRYSPSFQG (SEQ ID NO: 230) | MGTIYPGDDD TSYNPKFQG (SEQ ID NO: 259) | MGTIYPGNDD TSYNPSFQG (SEQ ID NO: 288) | GGYRAEDY (SEQ ID NO: 59) |
| | | MQGSHTPYT (SEQ ID NO: 191) | | MGTIYPGDDD TRYSQKFQG (SEQ ID NO: 231) | MGTIYPGDDD TSYNPSFQG (SEQ ID NO: 260) | | GGYRALDY (SEQ ID NO: 315) |
| | | MQGSHVPYT (SEQ ID NO: 97) | | | MGTIYPGDDD TSYNQKFQG (SEQ ID NO: 261) | | GGYRAPDY (SEQ ID NO: 316) |

TABLE 3-continued

Amino acid sequences of unique CDRs from 269 unique
anti-CD47 v-domains in the IGKV2-28/IGHV5-51 background.

| LCDR1 | LCDR2 | LCDR3 | HCDR1 | HCDR2 | HCDR2 | HCDR2 | HCDR3 |
|---|---|---|---|---|---|---|---|
| | | MQGSQIPYT (SEQ ID NO: 192) | | | | | GGYRAQDY (SEQ ID NO: 95) |
| | | MQGSQTPYT (SEQ ID NO: 193) | | | | | GGYRARDY (SEQ ID NO: 317) |
| | | MQGSQVPYT (SEQ ID NO: 194) | | | | | GGYRASDY (SEQ ID NO: 318) |
| | | | | | | | GGYRATDY (SEQ ID NO: 319) |
| | | | | | | | GGYRAVDY (SEQ ID NO: 320) |
| | | | | | | | GGYRIMDY (SEQ ID NO: 321) |
| | | | | | | | GGYRTEDY (SEQ ID NO: 322) |
| | | | | | | | GGYRTMDY (SEQ ID NO: 323) |
| | | | | | | | GGYRTTDY (SEQ ID NO: 324) |
| | | | | | | | GGYRVMDY (SEQ ID NO: 325) |
| | | | | | | | GGYRWMDY (SEQ ID NO: 326) |
| | | | | | | | QGYRAMDY (SEQ ID NO: 327) |

TABLE 4

Amino acid sequences of CDRs of unique, library-derived and
designer, human/cyno cross-reactive anti-CD47 IgGs.

| Clone name | LCDR1 | LCDR2 | LCDR3 | HCRD1 | HCDR2 | HCDR3 |
|---|---|---|---|---|---|---|
| F-E5 | RSSQSLLHSNGNTYLG (SEQ ID NO: 51) | KGSNRFS (SEQ ID NO: 52) | MQASQVPYT (SEQ ID NO: 63) | GYSFTNYNIH (SEQ ID NO: 57) | MGTIYPGNSDTSYNPKFQG (SEQ ID NO: 92) | GGKRAMDY (SEQ ID NO: 93) |
| A-H3 | RSSQSLLHSKGNTYLG (SEQ ID NO: 328) | KGSNRFS (SEQ ID NO: 52) | MQASQVPYT (SEQ ID NO: 63) | GYSFTNYNIH (SEQ ID NO: 57) | MGTIYPGNSDTSYNPSFQG (SEQ ID NO: 61) | GGVRAMDY (SEQ ID NO: 62) |
| C-D5 | RSSQSLLHSNYNTYLG (SEQ ID NO: 329) | KGSNRFS (SEQ ID NO: 52) | FQGSQTPYT (SEQ ID NO: 176) | GYSFTNYNIH (SEQ ID NO: 57) | MGTIYPGDSDTRYNPKFQG (SEQ ID NO: 58) | GGIRAMDY (SEQ ID NO: 99) |
| E-C5 | RSSQSLLHSNGNTYLG (SEQ ID NO: 51) | KGSNRFS (SEQ ID NO: 52) | MQASHVPYT (SEQ ID NO: 96) | GYSFTNYNIH (SEQ ID NO: 57) | MGTIYPGDSDTSYNPKFQG (SEQ ID NO: 94) | GGYRAQDY (SEQ ID NO: 95) |

TABLE 4-continued

Amino acid sequences of CDRs of unique, library-derived and designer, human/cyno cross-reactive anti-CD47 IgGs.

| Clone name | LCDR1 | LCDR2 | LCDR3 | HCRD1 | HCDR2 | HCDR3 |
|---|---|---|---|---|---|---|
| E-D6 | RSSQSLLHSNGNTYLG (SEQ ID NO: 51) | KGSNRFS (SEQ ID NO: 52) | MQGSHVPYT (SEQ ID NO: 97) | GYSFTNYNIH (SEQ ID NO: 57) | MGTIYPGDSDTSYNPKFQG (SEQ ID NO: 94) | GGYRAEDY (SEQ ID NO: 59) |
| B-A6 | RSSQSLLHSNGNTYLG (SEQ ID NO: 51) | KGSNRFS (SEQ ID NO: 52) | FQGSHVPYI (SEQ ID NO: 100) | GYSFTNYNIH (SEQ ID NO: 57) | MGTIYPGDSDTRYNQKFQG (SEQ ID NO: 98) | GGIRAMDY (SEQ ID NO: 99) |
| D-C12 | RSSQSLLHSNGNTYLG (SEQ ID NO: 51) | KGSNRFS (SEQ ID NO: 52) | MQGSHVPYT (SEQ ID NO: 97) | GYSFTNYNIH (SEQ ID NO: 57) | MGTIYPGNSDTRYNPKFQG (SEQ ID NO: 101) | GGFRAMDY (SEQ ID NO: 50) |
| B-D2 | RSSQSLLHSNGNTYLG (SEQ ID NO: 51) | KGSNRFS (SEQ ID NO: 52) | FQASQVPYT (SEQ ID NO: 54) | GYSFTNYNIH (SEQ ID NO: 57) | MGTIYPGNSDTRYNPSFQG (SEQ ID NO: 272) | GGERAMDY (SEQ ID NO: 294) |
| F-G3 | RSSQSLLHSNGNTYLG (SEQ ID NO: 51) | KGSNRFS (SEQ ID NO: 52) | MQASQVPYT (SEQ ID NO: 63) | GYSFTNYNIH (SEQ ID NO: 57) | MGTIYPGNSDTSYNHKFQG (SEQ ID NO: 331) | GGNRAEDY (SEQ ID NO: 333) |
| E-A1 | RSSQSLLHSNGNTYLG (SEQ ID NO: 51) | KGSNRFS (SEQ ID NO: 52) | MQGSHVPYT (SEQ ID NO: 97) | GYSFTNYNIH (SEQ ID NO: 57) | MGTIYPGDSDTRYNPKFQG (SEQ ID NO: 58) | GGYRAEDY (SEQ ID NO: 59) |
| D6 | RSSQSLLHSNGNTYLG (SEQ ID NO: 51) | KGSNRFS (SEQ ID NO: 52) | MQASQVPYT (SEQ ID NO: 63) | GYSFTNYNIH (SEQ ID NO: 57) | MGTIYPGNSDTSYNPSFQG (SEQ ID NO: 61) | GGVRAMDY (SEQ ID NO: 62) |
| VH1.1 | | | | GYTFTNYAMH (SEQ ID NO: 48) | MGTIYPGNDDTKYNQKFQG (SEQ ID NO: 49) | GGYRAEDY (SEQ ID NO: 59) |
| VH1.2 | | | | GYTFTDYNMH (SEQ ID NO: 88) | MGTIYPGNDDTKYNQKFQG (SEQ ID NO: 49) | GGYRAEDY (SEQ ID NO: 59) |
| VH1.3 | | | | GYTFTDYNMH (SEQ ID NO: 88) | MGTIYPGNDDTKYSQKFQG (SEQ ID NO: 91) | GGYRAEDY (SEQ ID NO: 59) |
| VH1.4 | | | | GYTFTDYNMH (SEQ ID NO: 88) | MGTIYPGNDDTKYSQKFQG (SEQ ID NO: 91) | GGFRAMDY (SEQ ID NO: 50) |
| VH1.5 | | | | GYTFTDYNMH (SEQ ID NO: 88) | MGTIYPGNDDTKYNQKFQG (SEQ ID NO: 49) | GGFRAMDY (SEQ ID NO: 50) |
| VH1.6 | | | | GYTFTNYAMH (SEQ ID NO: 48) | MGTIYPGNDDTSYSQKFQG (SEQ ID NO: 90) | GGYRAEDY (SEQ ID NO: 59) |
| VH1.7 | | | | GYTFTNYNIH (SEQ ID NO: 89) | MGTIYPGNDDTSYSQKFQG (SEQ ID NO: 90) | GGFRAMDY (SEQ ID NO: 50) |
| VH1.8 | | | | GYTFTNYAMH (SEQ ID NO: 48) | MGTIYPGNDDTKYNQKFQG (SEQ ID NO: 49) | GGFRAMDY (SEQ ID NO: 50) |
| VH1.9 | | | | GYTFTNYAMH (SEQ ID NO: 48) | MGTIYPGNDDTKYSQKFQG (SEQ ID NO: 91) | GGYRAEDY (SEQ ID NO: 59) |
| VH1.10 | | | | GYTFTDYNMH (SEQ ID NO: 88) | MGTIYPGNDDTSYSQKFQG (SEQ ID NO: 90) | GGFRAMDY (SEQ ID NO: 50) |
| VH1.11 | | | | GYTFTNYAMH (SEQ ID NO: 48) | MGTIYPGNDDTKYSQKFQG (SEQ ID NO: 91) | GGFRAMDY (SEQ ID NO: 50) |

TABLE 4-continued

Amino acid sequences of CDRs of unique, library-derived and designer, human/cyno cross-reactive anti-CD47 IgGs.

| Clone name | LCDR1 | LCDR2 | LCDR3 | HCRD1 | HCDR2 | HCDR3 |
|---|---|---|---|---|---|---|
| VH1.12 | | | | GYTFTNYAMH (SEQ ID NO: 48) | MGTIYPGNDNTKYNQKFQG (SEQ ID NO: 332) | GGFRAMDY (SEQ ID NO: 50) |
| VL1.1 | RSSQSLLHSNGNTYLG (SEQ ID NO: 51) | KGSNRFS (SEQ ID NO: 52) | FQASHVPYT (SEQ ID NO: 53) | | | |
| VL1.2 | RSSQSLLHSNGNTYLG (SEQ ID NO: 51) | KGSNRFS (SEQ ID NO: 52) | FQASQVPYT (SEQ ID NO: 54) | | | |
| VL1.3 | RSSQSLLHSNANTYLG (SEQ ID NO: 55) | KGSNRFS (SEQ ID NO: 52) | FQASQVPYT (SEQ ID NO: 54) | | | |
| VL1.4 | RSSQSLLHSNAYNYLG (SEQ ID NO: 56) | KGSNRFS (SEQ ID NO: 52) | FQASQVPYT (SEQ ID NO: 54) | | | |
| VL1.5 | RSSQSLLHSNAYNYLG (SEQ ID NO: 56) | KGSNRFS (SEQ ID NO: 52) | FQASHVPYT (SEQ ID NO: 53) | | | |
| VL1.6 | RSSQSLLHSNANTYLG (SEQ ID NO: 55) | KGSNRFS (SEQ ID NO: 52) | FQASHVPYT (SEQ ID NO: 53) | | | |
| VL1.7 | RSSQSLLHSNAYNYLG (SEQ ID NO: 56) | KGSNRAS (SEQ ID NO: 330) | FQASHVPYT (SEQ ID NO: 53) | | | |
| VL1.8 | RSSQSLLHSNAYNYLG (SEQ ID NO: 56) | KGSNRFS (SEQ ID NO: 52) | MQASHVPYT (SEQ ID NO: 96) | | | |
| VL1.9 | RSSQSLLHSNAYNYLG (SEQ ID NO: 56) | KGSNRAS (SEQ ID NO: 330) | MQASHVPYT (SEQ ID NO: 96) | | | |

TABLE 5

Assay technology known under the trademark HTRF® epitope competition IC50 values for designer lead IgGs.

| | IC50 µg/ml | |
|---|---|---|
| Antibody | hCD47 | cCD47 |
| m5F9G4 | 0.601 | 0.809 |
| h5F9G4 | 0.464 | 0.899 |
| VH1.8/VL1.1 | 0.459 | 0.629 |
| VH1.8/VL1.2 | 0.586 | 0.824 |
| VH1.8/VL1.3 | 0.928 | 1.327 |
| VH1.8/VL1.4 | 2.944 | 5.169 |
| VH1.8/VL1.5 | 0.911 | 1.36 |
| VH1.8/VL1.6 | 0.56 | 0.626 |
| VH1.1/VL1.6 | 6.963 | 1.818 |
| VH1.6/VL1.6 | 13.981 | 4.457 |
| VH1.7/VL1.4 | 22.624 | 13.241 |
| VH1.7/VL1.5 | 9.534 | 4.203 |
| VH1.7/vL1.6 | 4.637 | 1.422 |
| VH1.9/VL1.6 | 11.051 | 3.26 |
| VH1.12/VL1.8 | 16.259 | 5.843 |

TABLE 6

Steady State KD binding affinities for monomeric Fabs to human and cyno CD47.

| | Cyno CD47 | | Human CD47 | |
|---|---|---|---|---|
| Analyte | KD (nM) | Chi2 | KD (nM) | Chi2 |
| FAB h5F9G4 | 17.1 | 0.00827 | 11.9 | 0.0265 |
| FAB VH1.8/1.1 | 17.9 | 0.0366 | 7.4 | 0.0126 |
| FAB VH1.8/1.6 | 25.9 | 0.0564 | 15.9 | 0.00446 |
| FAB VH1.8/1.6DI | 27.8 | 0.00741 | 20.3 | 0.00696 |

TABLE 7

Examples of antibody variable region amino acid sequences.

VH1.8/VL1.6
heavy chain variable (VH) region
(SEQ ID NO: 1)
QVQLVQSGAEVKKPGASVKVSCKASGYTFTNYAMHWVRQAPGQRLEW

MGTIYPGNDDTKYNQKFQGRVTITADTSASTAYMELSSLRSEDTAVY

YCARGGFRAMDYWGQGTLVTVSS

TABLE 7-continued

Examples of antibody variable region amino acid sequences.

light chain variable (VL) region
(SEQ ID NO: 2)
DIVMTQSPLSLPVTPGEPASISCRSSQSLLHSNANTYLGWYLQKPGQ
SPQLLIYKGSNRFSGVPDRFSGSGSGTDFTLKISRVEAEDVGVYYCF
QASHVPYTFGQGTKLEIK VH1.8/VL1.6-DI
heavy chain variable (VH) region
(SEQ ID NO: 3)
QVQLVQSGAEVKKPGASVKVSCKASGYTFTNYAMHWVRQAPGQRLEW
MGTIYPGNDDTKYNQKFQGRVTITADTSASTAYMELSSLRSEDTAVY
YCARGGFRAMDYWGQGTLVTVSS light chain variable (VL) region
(SEQ ID NO: 4)
DIVMTQSPLSLPVTPGEPASISCRSSQSLLHSNANTYLGWYLQKPGQ
SPQLAIYKGSNRFSGVPDRFSGSGSGTDFTLKISRVEAEDAGVYYCF
QASHVPYTFGQGTKLEIK VH1.8/VL1.1
heavy chain variable (VH) region
(SEQ ID NO: 5)
QVQLVQSGAEVKKPGASVKVSCKASGYTFTNYAMHWVRQAPGQRLEW
MGTIYPGNDDTKYNQKFQGRVTITADTSASTAYMELSSLRSEDTAVY
YCARGGFRAMDYWGQGTLVTVSS light chain variable (VL) region
(SEQ ID NO: 6)
DIVMTQSPLSLPVTPGEPASISCRSSQSLLHSNGNTYLGWYLQKPGQ
SPQLLIYKGSNRFSGVPDRFSGSGSGTDFTLKISRVEAEDVGVYYCF
QASHVPYTFGQGTKLEIK VH1.8/VL1.5
heavy chain variable (VH) region
(SEQ ID NO: 7)
QVQLVQSGAEVKKPGASVKVSCKASGYTFTNYAMHWVRQAPGQRLEW
MGTIYPGNDDTKYNQKFQGRVTITADTSASTAYMELSSLRSEDTAVY
YCARGGFRAMDYWGQGTLVTVSS light chain variable (VL) region
(SEQ ID NO: 8)
DIVMTQSPLSLPVTPGEPASISCRSSQSLLHSNAYNYLGWYLQKPGQ
SPQLLIYKGSNRFSGVPDRFSGSGSGTDFTLKISRVEAEDVGVYYCF
QASHVPYTFGQGTKLEIK VH1.8/VL1.4
heavy chain variable (VH) region
(SEQ ID NO: 9)
QVQLVQSGAEVKKPGASVKVSCKASGYTFTNYAMHWVRQAPGQRLEW
MGTIYPGNDDTKYNQKFQGRVTITADTSASTAYMELSSLRSEDTAVY
YCARGGFRAMDYWGQGTLVTVSS light chain variable (VL) region
(SEQ ID NO: 10)
DIVMTQSPLSLPVTPGEPASISCRSSQSLLHSNAYNYLGWYLQKPGQ
SPQLLIYKGSNRFSGVPDRFSGSGSGTDFTLKISRVEAEDVGVYYCF
QASQVPYTFGQGTKLEIK

TABLE 7-continued

Examples of antibody variable region amino acid sequences.

VH1.8/VL1.3
heavy chain variable (VH) region
(SEQ ID NO: 11)
QVQLVQSGAEVKKPGASVKVSCKASGYTFTNYAMHWVRQAPGQRLEW
MGTIYPGNDDTKYNQKFQGRVTITADTSASTAYMELSSLRSEDTAVY
YCARGGFRAMDYWGQGTLVTVSS light chain variable (VL) region
(SEQ ID NO: 12)
DIVMTQSPLSLPVTPGEPASISCRSSQSLLHSNANTYLGWYLQKPGQ
SPQLLIYKGSNRFSGVPDRFSGSGSGTDFTLKISRVEAEDVGVYYCF
QASQVPYTFGQGTKLEIK VH1.8/VL1.2
heavy chain variable (VH) region
(SEQ ID NO: 13)
QVQLVQSGAEVKKPGASVKVSCKASGYTFTNYAMHWVRQAPGQRLEW
MGTIYPGNDDTKYNQKFQGRVTITADTSASTAYMELSSLRSEDTAVY
YCARGGFRAMDYWGQGTLVTVSS light chain variable (VL) region
(SEQ ID NO: 14)
DIVMTQSPLSLPVTPGEPASISCRSSQSLLHSNGNTYLGWYLQKPGQ
SPQLLIYKGSNRFSGVPDRFSGSGSGTDFTLKISRVEAEDVGVYYCF
QASQVPYTFGQGTKLEIK D6
heavy chain variable (VH) region
(SEQ ID NO: 15)
EVQLVQSGAEVKKPGESLKISCKGSGYSFTNYNIHWVRQMPGKGLEW
MGTIYPGNSDTSYNPSFQGQVTISADKSISTAYLQWSSLKASDTAMY
YCARGGVRAMDYWGQGTLVTVSS light chain variable (VL) region
(SEQ ID NO: 16)
DIVMTQSPLSLPVTPGEPASISCRSSQSLLHSNGNTYLGWYLQKPGQ
SPQLLIYKGSNRFSGVPDRFSGSGSGTDFTLKISRVEAEDVGVYYCM
QASQVPYTFGQGTKLEIK

TABLE 8

Examples of antibody Fc region amino acid sequences.

Human IgG4 wild type
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK (SEQ ID NO: 17)

Human IgG4(S228P)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK (SEQ ID NO: 18)

TABLE 8-continued

Examples of antibody Fc region amino acid sequences.

Human IgG1 wild type
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 19)

Human IgG1-3M
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 20)

Human IgG2 wild type
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDISVEWESNGQPENNYKTTPPMLDSDGSFFLYSKLTVDKSRWQQGN
VFSCSVMHEALHNHYTQKSLSLSPGK (SEQ ID NO: 21)

Human IgG1 wild type "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 22)

Human IgG1-3M "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMKNQVSLTCL VKGFYPSDIAVEWESNGQPENNYKTTPPVLDSDGSFFLYSKLTVDKSRWQ
QGNVFSCSVMHEALHNHYTQKSLSLSPGK (SEQ ID NO: 23)

TABLE 9

Examples of CD47 protein amino acid sequences.

Human CD47 sequence
(SEQ ID NO: 24)
MWPLVAALLLGSACCGSAQLLFNKTKSVEFTFCNDTVVIPCFVTNME

AQNTTEVYVKWKFKGRDIYTFDGALNKSTVPTDFSSAKIEVSQLLKG

DASLKMDKSDAVSHTGNYTCEVTELTREGETIIELKYRVVSWFSPNE

NILIVIFPIFAILLFWGQFGIKTLKYRSGGMDEKTIALLVAGLVITV

IVIVGAILFVPGEYSLKNATGLGLIVTSTGILILLHYYVFSTAIGLT

SFVIAILVIQVIAYILAVVGLSLCIAACIPMHGPLLISGLSILALAQ

LLGLVYMKFVASNQKTIQPPRKAVEEPLNAFKESKGMMNDE

Cynomolgus monkey CD47 sequence
(SEQ ID NO: 25)
MWPLVAALLLGSACCGSAQLLFNKTKSVEFTFCNDTVVIPCFVTNME

AQNTTEVYVKWKFKGRDIYTFDGALNKSTAPANFSSAKIEVSQLLKG

DASLKMDKSDAVSHTGNYTCEVTELTREGETIIELKYRVVSWFSPNE

NILIVIFPIFAILLFWGQFGIKTLKYRSGGMDEKTIALLVAGLMITV

IVIVGAILFVPGEYSLKNATGLGLIVTSTGILILLHYYVFSTAIGLT

SFVIAILVIQVIAYILAVVGLSLCIAACIPMHGPLLISGLSILALAQ

LLGLVYMKFVASNQKTIQPPRKAVEEPLNAFKESKGMMNDE

The invention claimed is:

1. An anti-CD47 antibody or an antigen-binding portion thereof, wherein the antibody or antigen-binding portion comprises a heavy chain variable (VH) region and a light chain variable (VL) region, wherein
   (a) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASHVPYT (SEQ ID NO:53);
   (b) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNGNTYLG (SEQ ID NO:51), LCDR2 of KGSNRFS (SEQ ID NO:52) and LCDR3 of FQASHVPYT (SEQ ID NO:53);
   (c) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNAYNYLG (SEQ ID NO:56), LCDR2 of KGSNRFS (SEQ ID NO:52) and LCDR3 of FQASHVPYT (SEQ ID NO:53);
   (d) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNAYNYLG (SEQ ID NO:56), LCDR2 of KGSNRFS (SEQ ID NO:52) and LCDR3 of FQASQVPYT (SEQ ID NO:54);
   (e) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASQVPYT (SEQ ID NO:54);
   (f) the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNGNTYLG (SEQ ID NO:51), LCDR2 of KGSNRFS (SEQ ID NO:52) and LCDR3 of FQASQVPYT (SEQ ID NO:54); or
   (g) the VH region amino acid sequence comprises HCDR1 of GYSFTNYNIH (SEQ ID NO:57), HCDR2 of MGTIYPGNSDTSYNPSFQG (SEQ ID NO: 61) and HCDR3 of GGVRAMDY (SEQ ID NO:62); and the VL region amino acid sequence comprises LCDR1 of RSSQSLLHSNGNTYLG (SEQ ID NO:51), LCDR2 of KGSNRFS (SEQ ID NO:52) and LCDR3 of MQASQVPYT (SEQ ID NO:63).

2. The antibody or antigen-binding portion of claim 1, wherein
   (a) the VH region amino acid sequence comprises SEQ ID NO: 1 and the VL region amino acid sequence comprises SEQ ID NO:2;
   (b) the VH region amino acid sequence comprises SEQ ID NO:3 and the VL region amino acid sequence comprises SEQ ID NO:4;
   (c) the VH region amino acid sequence comprises SEQ ID NO:5 and the VL region amino acid sequence comprises SEQ ID NO:6;
   (d) the VH region amino acid sequence comprises SEQ ID NO:7 and the VL region amino acid sequence comprises SEQ ID NO:8;

(e) the VH region amino acid sequence comprises SEQ ID NO:9 and the VL region amino acid sequence comprises SEQ ID NO: 10;

(f) the VH region amino acid sequence comprises SEQ ID NO: 11 and the VL region amino acid sequence comprises SEQ ID NO: 12;

(g) the VH region amino acid sequence comprises SEQ ID NO: 13 and the VL region amino acid sequence comprises SEQ ID NO: 14; or (h) the VH region amino acid sequence comprises SEQ ID NO:15 and the VL region amino acid sequence comprises SEQ ID NO: 16.

3. The antibody or antigen-binding portion of claim 1, wherein the antibody is humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1, wherein the VH region comprises an IGHV5-51 or IGHV1-3 human germline scaffold amino acid sequence into which the HCDR1, HCDR2 and HCDR3 amino acid sequences have been inserted.

7. The antibody or antigen-binding portion of claim 1, wherein the VL region comprises an IGKV2-28 human germline scaffold amino acid sequence into which the LCDR1, LCDR2 and LCDR3 amino acid sequences have been inserted.

8. The antibody or antigen-binding portion of claim 1, wherein the antibody or antigen-binding portion comprises an immunoglobulin constant region.

9. The antibody or antigen-binding portion of claim 8, wherein the immunoglobulin constant region is IgG, IgE, IgM, IgD, IgA or IgY.

10. The antibody or antigen-binding portion of claim 9, wherein the immunoglobulin constant region is IgG1, IgG2, IgG3, IgG4, IgA1 or IgA2.

11. The antibody or antigen-binding portion of claim 8, wherein the immunoglobulin constant region is a wild-type human IgG4 constant region, a human IgG4 constant region comprising the amino acid substitution S228P, a wild-type human IgG1 constant region, a human IgG1 constant region comprising the amino acid substitutions L234A, L235A and G237A or a wild-type human IgG2 constant region.

12. The antibody or antigen-binding portion of claim 8, wherein the immunoglobulin constant region comprises any one of SEQ ID NOS:17-23.

13. The antibody or antigen-binding portion of claim 1, wherein the antibody or antigen-binding portion is an Fab, an Fab', an F(ab')2, an Fv, an scFv, a maxibody, a minibody, an intrabody, a diabody, a triabody, a tetrabody, or a bis-scFv.

14. The antibody or antigen-binding portion of claim 1, wherein the antibody or antigen-binding portion is monoclonal.

15. The antibody or antigen-binding portion of claim 1, wherein the antibody or antigen-binding portion is tetrameric, tetravalent or multispecific.

16. An immunoconjugate comprising the antibody or antigen-binding portion of claim 1, linked to a therapeutic agent.

17. A pharmaceutical composition comprising the antibody or antigen-binding portion of claim 1 and a pharmaceutically acceptable carrier.

18. A nucleic acid molecule encoding both the VH and the VL region amino acid sequences of the antibody or antigen-binding portion of claim 1.

19. An expression vector comprising the nucleic acid molecule of claim 18.

20. An individual recombinant host cell comprising the nucleic acid molecule of claim 18.

21. A method of producing an anti-CD47 antibody or an antigen-binding portion thereof, the method comprising:
culturing the recombinant host cell of claim 20 under conditions whereby the nucleic acid molecule is expressed, thereby producing the antibody or antigen-binding portion; and
isolating the antibody or antigen-binding portion from the host cell or culture.

22. A method for enhancing an immune response in a subject in need thereof, comprising administering to the subject a therapeutically effective amount of the antibody or antigen-binding portion of claim 1, thereby enhancing the immune response.

23. The method of claim 22, wherein the subject has a cancer, an autoimmune disease, an inflammatory disease, a cardiovascular disease or a fibrotic disease.

24. The method of claim 23, wherein the cancer is gastrointestinal stromal cancer (GIST), pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma or cancer of hematological tissues.

25. The method of claim 23, wherein the autoimmune disease or the inflammatory disease is arthritis, asthma, multiple sclerosis, psoriasis, Crohn's disease, inflammatory bowel disease, lupus, Grave's disease, Hashimoto's thyroiditis or ankylosing spondylitis.

26. The method of claim 23, wherein the cardiovascular disease is coronary heart disease or atherosclerosis.

27. The method of claim 23, wherein the fibrotic disease is myocardial infarction, angina, osteoarthritis, pulmonary fibrosis, cystic fibrosis, bronchitis or asthma.

28. An anti-CD47 antibody or an antigen-binding portion thereof, wherein the antibody or antigen-binding portion comprises a heavy chain variable (VH) region and a light chain variable (VL) region, wherein the VH region amino acid sequence comprises HCDR1 of GYTFTNYAMH (SEQ ID NO:48), HCDR2 of MGTIYPGNDDTKYNQKFQG (SEQ ID NO:49) and HCDR3 of GGFRAMDY (SEQ ID NO:50); and the VL region amino acid sequence comprises LCDR1 of RSSQSLLHSNANTYLG (SEQ ID NO:55), LCDR2 of KGSNRFS (SEQ ID NO:52) and LCDR3 of FQASHVPYT (SEQ ID NO:53).

\* \* \* \* \*

SEQUENCE LISTING

<160> NUMBER OF SEQ ID NOS: 333

<210> SEQ ID NO 1
<211> LENGTH: 117
<212> TYPE: PRT
<213> ORGANISM: Artificial Sequence
<220> FEATURE:
<223> OTHER INFORMATION: VH1.8/VL1.6 heavy chain variable (VH) region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Thr Ile Tyr Pro Gly Asn Asp Asp Thr Lys Tyr Asn Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Ala Met Asp Tyr Trp Gly Gln Gly Thr Leu
            100                 105                 110

Val Thr Val Ser Ser
        115

<210> SEQ ID NO 2
<211> LENGTH: 112
<212> TYPE: PRT
<213> ORGANISM: Artificial Sequence
<220> FEATURE:
<223> OTHER INFORMATION: VH1.8/VL1.6 light chain variable (VL) region

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Ala Asn Thr Tyr Leu Gly Trp Tyr Leu Gln Lys Pro Gly Gln Ser
        35                  40                  45

Pro Gln Leu Leu Ile Tyr Lys Gly Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

<210> SEQ ID NO 3
<211> LENGTH: 117
<212> TYPE: PRT
<213> ORGANISM: Artificial Sequence
<220> FEATURE:
<223> OTHER INFORMATION: VH1.8/VL1.6-DI heavy chain variable (VH) region

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Thr Ile Tyr Pro Gly Asn Asp Asp Thr Lys Tyr Asn Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Ala Met Asp Tyr Trp Gly Gln Gly Thr Leu
            100                 105                 110

Val Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: VH1.8/VL1.6-DI light chain variable (VL) region

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Ala Asn Thr Tyr Leu Gly Trp Tyr Leu Gln Lys Pro Gly Gln Ser
        35                  40                  45

Pro Gln Leu Ala Ile Tyr Lys Gly Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ala Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

<210> SEQ ID NO 5
<211> LENGTH: 117
<212> TYPE: PRT
<213> ORGANISM: Artificial Sequence
<220> FEATURE:
<223> OTHER INFORMATION: VH1.8/VL1.1 heavy chain variable (VH) region

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Thr Ile Tyr Pro Gly Asn Asp Asp Thr Lys Tyr Asn Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Ala Met Asp Tyr Trp Gly Gln Gly Thr Leu
            100                 105                 110

Val Thr Val Ser Ser
        115

<210> SEQ ID NO 6
<211> LENGTH: 112
<212> TYPE: PRT
<213> ORGANISM: Artificial Sequence
<220> FEATURE:
<223> OTHER INFORMATION: VH1.8/VL1.1 light chain variable (VL) region

<400> SEQUENCE: 6

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Gly Ser Asn Arg Phe Ser Gly Val Pro
    50                  55                  60

-continued

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

<210> SEQ ID NO 7
<211> LENGTH: 117
<212> TYPE: PRT
<213> ORGANISM: Artificial Sequence
<220> FEATURE:
<223> OTHER INFORMATION: VH1.8/VL1.5 heavy chain variable (VH) region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Ala Met His Trp Val Arg Gln Ala Pro Gly Gln Arg Leu Glu Trp Met
            35                  40                  45

Gly Thr Ile Tyr Pro Gly Asn Asp Asp Thr Lys Tyr Asn Gln Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Ala Met Asp Tyr Trp Gly Gln Gly Thr Leu
            100                 105                 110

Val Thr Val Ser Ser
            115

<210> SEQ ID NO 8
<211> LENGTH: 112
<212> TYPE: PRT
<213> ORGANISM: Artificial Sequence
<220> FEATURE:
<223> OTHER INFORMATION: VH1.8/VL1.5 light chain variable (VL) region

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Ala Tyr Asn Tyr Leu Gly Trp Tyr Leu Gln Lys Pro Gly Gln Ser
            35                  40                  45

Pro Gln Leu Leu Ile Tyr Lys Gly Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

<210> SEQ ID NO 9
<211> LENGTH: 117
<212> TYPE: PRT

```
<213> ORGANISM: Artificial Sequence
<220> FEATURE:
<223> OTHER INFORMATION: VH1.8/VL1.4 heavy chain variable (VH) region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Thr Ile Tyr Pro Gly Asn Asp Asp Thr Lys Tyr Asn Gln Lys Phe
50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Ala Met Asp Tyr Trp Gly Gln Gly Thr Leu
            100                 105                 110

Val Thr Val Ser Ser
        115

<210> SEQ ID NO 10
<211> LENGTH: 112
<212> TYPE: PRT
<213> ORGANISM: Artificial Sequence
<220> FEATURE:
<223> OTHER INFORMATION: VH1.8/VL1.4 light chain variable (VL) region

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Ala Tyr Asn Tyr Leu Gly Trp Tyr Leu Gln Lys Pro Gly Gln Ser
        35                  40                  45

Pro Gln Leu Leu Ile Tyr Lys Gly Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser Gln Val Pro Tyr Thr Phe Gly Gln Gly Thr Lys Leu Glu Ile Lys
            100                 105                 110

<210> SEQ ID NO 11
<211> LENGTH: 117
<212> TYPE: PRT
<213> ORGANISM: Artificial Sequence
<220> FEATURE:
<223> OTHER INFORMATION: VH1.8/VL1.3 heavy chain variable (VH) region

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45
```

```
Gly Thr Ile Tyr Pro Gly Asn Asp Asp Thr Lys Tyr Asn Gln Lys Phe
        50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Phe Arg Ala Met Asp Tyr Trp Gly Gln Gly Thr Leu
                100                 105                 110

Val Thr Val Ser Ser
            115

<210> SEQ ID NO 12
<211> LENGTH: 112
<212> TYPE: PRT
<213> ORGANISM: Artificial Sequence
<220> FEATURE:
<223> OTHER INFORMATION: VH1.8/VL1.3 light chain variable (VL) region

<400> SEQUENCE: 12

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Ala Asn Thr Tyr Leu Gly Trp Tyr Leu Gln Lys Pro Gly Gln Ser
                 35                  40                  45

Pro Gln Leu Leu Ile Tyr Lys Gly Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ala
                 85                  90                  95

Ser Gln Val Pro Tyr Thr Phe Gly Gln Gly Thr Lys Leu Glu Ile Lys
                100                 105                 110

<210> SEQ ID NO 13
<211> LENGTH: 117
<212> TYPE: PRT
<213> ORGANISM: Artificial Sequence
<220> FEATURE:
<223> OTHER INFORMATION: VH1.8/VL1.2 heavy chain variable (VH) region

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Ala Met His Trp Val Arg Gln Ala Pro Gly Gln Arg Leu Glu Trp Met
                 35                  40                  45

Gly Thr Ile Tyr Pro Gly Asn Asp Asp Thr Lys Tyr Asn Gln Lys Phe
        50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Phe Arg Ala Met Asp Tyr Trp Gly Gln Gly Thr Leu
                100                 105                 110

Val Thr Val Ser Ser
```

<210> SEQ ID NO 14
<211> LENGTH: 112
<212> TYPE: PRT
<213> ORGANISM: Artificial Sequence
<220> FEATURE:
<223> OTHER INFORMATION: VH1.8/VL1.2 light chain variable (VL) region

<400> SEQUENCE: 14

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Gly Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser Gln Val Pro Tyr Thr Phe Gly Gln Gly Thr Lys Leu Glu Ile Lys
            100                 105                 110
```

<210> SEQ ID NO 15
<211> LENGTH: 117
<212> TYPE: PRT
<213> ORGANISM: Artificial Sequence
<220> FEATURE:
<223> OTHER INFORMATION: D6 heavy chain variable (VH) region

<400> SEQUENCE: 15

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Asn Ile His Trp Val Arg Gln Met Pro Gly Lys Gly Leu Glu Trp Met
        35                  40                  45

Gly Thr Ile Tyr Pro Gly Asn Ser Asp Thr Ser Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Val Arg Ala Met Asp Tyr Trp Gly Gln Gly Thr Leu
            100                 105                 110

Val Thr Val Ser Ser
        115
```

<210> SEQ ID NO 16
<211> LENGTH: 112
<212> TYPE: PRT
<213> ORGANISM: Artificial Sequence
<220> FEATURE:
<223> OTHER INFORMATION: D6 light chain variable (VL) region

<400> SEQUENCE: 16

```
Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Leu His Ser
                20                  25                  30

Asn Gly Asn Thr Tyr Leu Gly Trp Tyr Leu Gln Lys Pro Gly Gln Ser
            35                  40                  45

Pro Gln Leu Leu Ile Tyr Lys Gly Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Gln Val Pro Tyr Thr Phe Gly Gln Gly Thr Lys Leu Glu Ile Lys
            100                 105                 110

<210> SEQ ID NO 17
<211> LENGTH: 327
<212> TYPE: PRT
<213> ORGANISM: Homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser

```
                275                 280                 285
Arg Leu Thr Val Asp Lys Ser Arg Trp Gln Glu Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 18
<211> LENGTH: 327
<212> TYPE: PRT
<213> ORGANISM: Homo sapiens

<400> SEQUENCE: 18

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
```

Leu Ser Leu Ser Leu Gly Lys
                325

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 330
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 326
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                    100                 105                 110

Pro Ala Pro Glu Leu Leu Gly Pro Ser Val Phe Leu Phe Pro Pro
                    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 23
<211> LENGTH: 329
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                    100                 105                 110
```

```
Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 24
<211> LENGTH: 323
<212> TYPE: PRT
<213> ORGANISM: Homo sapiens

<400> SEQUENCE: 24

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
            85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160
```

```
Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 25
<211> LENGTH: 323
<212> TYPE: PRT
<213> ORGANISM: Macaca fascicularis

<400> SEQUENCE: 25

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Ala Pro Ala Asn
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Met Ile Thr Val Ile Val Ile Val
            180                 185                 190

Gly Ala Ile Leu Phe Val Pro Gly Glu Tyr Ser Leu Lys Asn Ala Thr
        195                 200                 205
```

```
Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys
            290                 295                 300

Ala Val Glu Glu Pro Leu Asn Ala Phe Lys Glu Ser Lys Gly Met Met
305                 310                 315                 320

Asn Asp Glu

<210> SEQ ID NO 26
<211> LENGTH: 5
<212> TYPE: PRT
<213> ORGANISM: Homo sapiens

<400> SEQUENCE: 26

Arg Asp Glu Leu Thr
1               5

<210> SEQ ID NO 27
<211> LENGTH: 4
<212> TYPE: PRT
<213> ORGANISM: Homo sapiens

<400> SEQUENCE: 27

Arg Glu Glu Met
1

<210> SEQ ID NO 28
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1
<220> FEATURE:
<221> NAME/KEY: misc_feature
<222> LOCATION: (6)..(6)
<223> OTHER INFORMATION: Xaa can be Asn or a conservative substitution
      of Asn
<220> FEATURE:
<221> NAME/KEY: misc_feature
<222> LOCATION: (8)..(8)
<223> OTHER INFORMATION: Xaa can be Asn or a conservative substitution
      of Asn
<220> FEATURE:
<221> NAME/KEY: misc_feature
<222> LOCATION: (9)..(9)
<223> OTHER INFORMATION: Xaa can be Met or a conservative substitution
      of Met
<220> FEATURE:
<221> NAME/KEY: misc_feature
<222> LOCATION: (10)..(10)
<223> OTHER INFORMATION: Xaa can be His or any amino acid

<400> SEQUENCE: 28

Gly Tyr Ser Phe Thr Xaa Tyr Xaa Xaa Xaa
1               5                   10
```

```
<210> SEQ ID NO 29
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (1)..(1)
<223> OTHER INFORMATION: Xaa can be Met or a conservative substitution
      of Met
<220> FEATURE:
<221> NAME/KEY: misc_feature
<222> LOCATION: (3)..(3)
<223> OTHER INFORMATION: Xaa can be Thr or any amino acid
<220> FEATURE:
<221> NAME/KEY: misc_feature
<222> LOCATION: (8)..(8)
<223> OTHER INFORMATION: Xaa can be Asn or any amino acid
<220> FEATURE:
<221> NAME/KEY: misc_feature
<222> LOCATION: (9)..(9)
<223> OTHER INFORMATION: Xaa can be Asp or any amino acid
<220> FEATURE:
<221> NAME/KEY: misc_feature
<222> LOCATION: (12)..(12)
<223> OTHER INFORMATION: Xaa can be Ser or any amino acid
<220> FEATURE:
<221> NAME/KEY: misc_feature
<222> LOCATION: (14)..(14)
<223> OTHER INFORMATION: Xaa can be Asn or any amino acid
<220> FEATURE:
<221> NAME/KEY: misc_feature
<222> LOCATION: (15)..(15)
<223> OTHER INFORMATION: Xaa can be Gln or any amino acid
<220> FEATURE:
<221> NAME/KEY: misc_feature
<222> LOCATION: (16)..(16)
<223> OTHER INFORMATION: Xaa can be Lys or any amino acid
<220> FEATURE:
<221> NAME/KEY: misc_feature
<222> LOCATION: (18)..(18)
<223> OTHER INFORMATION: Xaa can be Gln or Lys
<220> FEATURE:
<221> NAME/KEY: misc_feature
<222> LOCATION: (19)..(19)
<223> OTHER INFORMATION: Xaa can be Gly or Asp

<400> SEQUENCE: 29

Xaa Gly Xaa Ile Tyr Pro Gly Xaa Xaa Asp Thr Xaa Tyr Xaa Xaa Xaa
1               5                   10                  15

Phe Xaa Xaa

<210> SEQ ID NO 30
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3
<220> FEATURE:
<221> NAME/KEY: misc_feature
<222> LOCATION: (1)..(1)
<223> OTHER INFORMATION: Xaa can be Gly or any amino acid
<220> FEATURE:
<221> NAME/KEY: misc_feature
<222> LOCATION: (3)..(3)
<223> OTHER INFORMATION: Xaa can be Tyr or any amino acid
<220> FEATURE:
<221> NAME/KEY: misc_feature
<222> LOCATION: (5)..(5)
<223> OTHER INFORMATION: Xaa can be Ala or any amino acid
<220> FEATURE:
<221> NAME/KEY: misc_feature
```

```
<222> LOCATION: (6)..(6)
<223> OTHER INFORMATION: Xaa can be Met or any amino acid

<400> SEQUENCE: 30

Xaa Gly Xaa Arg Xaa Xaa Asp Tyr
1               5

<210> SEQ ID NO 31
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1
<220> FEATURE:
<221> NAME/KEY: misc_feature
<222> LOCATION: (6)..(6)
<223> OTHER INFORMATION: Xaa can be Asn or any amino acid
<220> FEATURE:
<221> NAME/KEY: misc_feature
<222> LOCATION: (8)..(8)
<223> OTHER INFORMATION: Xaa can be Asn or any amino acid

<400> SEQUENCE: 31

Gly Tyr Thr Phe Thr Xaa Tyr Xaa Met His
1               5                   10

<210> SEQ ID NO 32
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (10)..(10)
<223> OTHER INFORMATION: Xaa can be Asp or any amino acid
<220> FEATURE:
<221> NAME/KEY: misc_feature
<222> LOCATION: (12)..(12)
<223> OTHER INFORMATION: Xaa can be Ser or any amino acid
<220> FEATURE:
<221> NAME/KEY: misc_feature
<222> LOCATION: (14)..(14)
<223> OTHER INFORMATION: Xaa can be Asn or any amino acid

<400> SEQUENCE: 32

Met Gly Thr Ile Tyr Pro Gly Asn Asp Xaa Thr Xaa Tyr Xaa Gln Lys
1               5                   10                  15

Phe Gln Gly

<210> SEQ ID NO 33
<211> LENGTH: 10
<212> TYPE: PRT
<213> ORGANISM: Artificial Sequence
<220> FEATURE:
<223> OTHER INFORMATION: 5F9G4 murine/humanized antibody HCDR1

<400> SEQUENCE: 33

Gly Tyr Thr Phe Thr Asn Tyr Asn Met His
1               5                   10

<210> SEQ ID NO 34
<211> LENGTH: 19
<212> TYPE: PRT
<213> ORGANISM: Artificial Sequence
<220> FEATURE:
<223> OTHER INFORMATION: 5F9G4 murine/humanized antibody HCDR2
```

```
<400> SEQUENCE: 34

Met Gly Thr Ile Tyr Pro Gly Asn Asp Asp Thr Ser Tyr Asn Gln Lys
1               5                   10                  15

Phe Lys Asp

<210> SEQ ID NO 35
<211> LENGTH: 8
<212> TYPE: PRT
<213> ORGANISM: Artificial Sequence
<220> FEATURE:
<223> OTHER INFORMATION: 5F9G4 murine/humanized antibody HCDR3

<400> SEQUENCE: 35

Gly Gly Tyr Arg Ala Met Asp Tyr
1               5

<210> SEQ ID NO 36
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1
<220> FEATURE:
<221> NAME/KEY: misc_feature
<222> LOCATION: (6)..(6)
<223> OTHER INFORMATION: Xaa can be Ile or a conservative substitution
      of Ile
<220> FEATURE:
<221> NAME/KEY: misc_feature
<222> LOCATION: (7)..(7)
<223> OTHER INFORMATION: Xaa can be Val or a conservative substitution
      of Val
<220> FEATURE:
<221> NAME/KEY: misc_feature
<222> LOCATION: (8)..(8)
<223> OTHER INFORMATION: Xaa can be Tyr or a conservative substitution
      of Tyr
<220> FEATURE:
<221> NAME/KEY: misc_feature
<222> LOCATION: (10)..(10)
<223> OTHER INFORMATION: Xaa can be Asn or any amino acid
<220> FEATURE:
<221> NAME/KEY: misc_feature
<222> LOCATION: (11)..(11)
<223> OTHER INFORMATION: Xaa can be Gly or any amino acid
<220> FEATURE:
<221> NAME/KEY: misc_feature
<222> LOCATION: (12)..(12)
<223> OTHER INFORMATION: Xaa can be Asn or any amino acid
<220> FEATURE:
<221> NAME/KEY: misc_feature
<222> LOCATION: (13)..(13)
<223> OTHER INFORMATION: Xaa can be Thr or any amino acid
<220> FEATURE:
<221> NAME/KEY: misc_feature
<222> LOCATION: (16)..(16)
<223> OTHER INFORMATION: Xaa can be Gly or any amino acid

<400> SEQUENCE: 36

Arg Ser Ser Gln Ser Xaa Xaa Xaa Ser Xaa Xaa Xaa Xaa Tyr Leu Xaa
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2
<220> FEATURE:
<221> NAME/KEY: misc_feature
```

```
<222> LOCATION: (2)..(2)
<223> OTHER INFORMATION: Xaa can be Val or any amino acid
<220> FEATURE:
<221> NAME/KEY: misc_feature
<222> LOCATION: (6)..(6)
<223> OTHER INFORMATION: Xaa can be Phe or any amino acid

<400> SEQUENCE: 37

Lys Xaa Ser Asn Arg Xaa Ser
1               5

<210> SEQ ID NO 38
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3
<220> FEATURE:
<221> NAME/KEY: misc_feature
<222> LOCATION: (1)..(1)
<223> OTHER INFORMATION: Xaa can be Phe or any amino acid
<220> FEATURE:
<221> NAME/KEY: misc_feature
<222> LOCATION: (3)..(3)
<223> OTHER INFORMATION: Xaa can be Gly or any amino acid
<220> FEATURE:
<221> NAME/KEY: misc_feature
<222> LOCATION: (4)..(4)
<223> OTHER INFORMATION: Xaa can be Ser or any amino acid
<220> FEATURE:
<221> NAME/KEY: misc_feature
<222> LOCATION: (5)..(5)
<223> OTHER INFORMATION: Xaa can be His or any amino acid
<220> FEATURE:
<221> NAME/KEY: misc_feature
<222> LOCATION: (6)..(6)
<223> OTHER INFORMATION: Xaa can be Val or any amino acid
<220> FEATURE:
<221> NAME/KEY: misc_feature
<222> LOCATION: (9)..(9)
<223> OTHER INFORMATION: Xaa can be Thr or any amino acid

<400> SEQUENCE: 38

Xaa Gln Xaa Xaa Xaa Xaa Pro Tyr Xaa
1               5

<210> SEQ ID NO 39
<211> LENGTH: 16
<212> TYPE: PRT
<213> ORGANISM: Artificial Sequence
<220> FEATURE:
<223> OTHER INFORMATION: 5F9G4 murine/humanized antibody LCDR1

<400> SEQUENCE: 39

Arg Ser Ser Gln Ser Ile Val Tyr Ser Asn Gly Asn Thr Tyr Leu Gly
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: 5F9G4 murine/humanized antibody LCDR2

<400> SEQUENCE: 40

Lys Val Ser Asn Arg Phe Ser
1               5

<210> SEQ ID NO 41
<211> LENGTH: 9
```

```
<212> TYPE: PRT
<213> ORGANISM: Artificial Sequence
<220> FEATURE:
<223> OTHER INFORMATION: 5F9G4 murine/humanized antibody LCDR3

<400> SEQUENCE: 41

Phe Gln Gly Ser His Val Pro Tyr Thr
1               5

<210> SEQ ID NO 42
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1
<220> FEATURE:
<221> NAME/KEY: misc_feature
<222> LOCATION: (3)..(3)
<223> OTHER INFORMATION: Xaa can be Ser or a conservative substitution
      of Ser
<220> FEATURE:
<221> NAME/KEY: misc_feature
<222> LOCATION: (6)..(6)
<223> OTHER INFORMATION: Xaa can be Asn or a conservative substitution
      of Asn
<220> FEATURE:
<221> NAME/KEY: misc_feature
<222> LOCATION: (8)..(8)
<223> OTHER INFORMATION: Xaa can be Asn or any other amino acid
<220> FEATURE:
<221> NAME/KEY: misc_feature
<222> LOCATION: (9)..(9)
<223> OTHER INFORMATION: Xaa can be Met or a conservative substitution
      of Met
<220> FEATURE:
<221> NAME/KEY: misc_feature
<222> LOCATION: (10)..(10)
<223> OTHER INFORMATION: Xaa can be His or any other amino acid

<400> SEQUENCE: 42

Gly Tyr Xaa Phe Thr Xaa Tyr Xaa Xaa Xaa
1               5                   10

<210> SEQ ID NO 43
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (1)..(1)
<223> OTHER INFORMATION: Xaa can be Met or a conservative substitution
      of Met
<220> FEATURE:
<221> NAME/KEY: misc_feature
<222> LOCATION: (2)..(2)
<223> OTHER INFORMATION: Xaa can be Gly or a conservative substitution
      of Gly
<220> FEATURE:
<221> NAME/KEY: misc_feature
<222> LOCATION: (3)..(3)
<223> OTHER INFORMATION: Xaa can be Thr or any other amino acid
<220> FEATURE:
<221> NAME/KEY: misc_feature
<222> LOCATION: (8)..(8)
<223> OTHER INFORMATION: Xaa can be Asn or a conservative substitution
      of Asn
<220> FEATURE:
<221> NAME/KEY: misc_feature
<222> LOCATION: (9)..(9)
<223> OTHER INFORMATION: Xaa can be Asp or any other amino acid
<220> FEATURE:
```

```
<221> NAME/KEY: misc_feature
<222> LOCATION: (10)..(10)
<223> OTHER INFORMATION: Xaa can be Asp or any other amino acid
<220> FEATURE:
<221> NAME/KEY: misc_feature
<222> LOCATION: (12)..(12)
<223> OTHER INFORMATION: Xaa can be Ser or any other amino acid
<220> FEATURE:
<221> NAME/KEY: misc_feature
<222> LOCATION: (14)..(14)
<223> OTHER INFORMATION: Xaa can be Asn or any other amino acid
<220> FEATURE:
<221> NAME/KEY: misc_feature
<222> LOCATION: (15)..(15)
<223> OTHER INFORMATION: Xaa can be Gln or any other amino acid
<220> FEATURE:
<221> NAME/KEY: misc_feature
<222> LOCATION: (16)..(16)
<223> OTHER INFORMATION: Xaa can be Lys or any other amino acid

<400> SEQUENCE: 43

Xaa Xaa Xaa Ile Tyr Pro Gly Xaa Xaa Thr Xaa Tyr Xaa Xaa Xaa
1               5                   10                  15
Phe Gln Gly

<210> SEQ ID NO 44
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3
<220> FEATURE:
<221> NAME/KEY: misc_feature
<222> LOCATION: (1)..(1)
<223> OTHER INFORMATION: Xaa can be Gly or any other amino acid
<220> FEATURE:
<221> NAME/KEY: misc_feature
<222> LOCATION: (3)..(3)
<223> OTHER INFORMATION: Xaa can be Tyr or any other amino acid
<220> FEATURE:
<221> NAME/KEY: misc_feature
<222> LOCATION: (5)..(5)
<223> OTHER INFORMATION: Xaa can be Ala or any other amino acid
<220> FEATURE:
<221> NAME/KEY: misc_feature
<222> LOCATION: (6)..(6)
<223> OTHER INFORMATION: Xaa can be Met or any other amino acid

<400> SEQUENCE: 44

Xaa Gly Xaa Arg Xaa Xaa Asp Tyr
1               5

<210> SEQ ID NO 45
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1
<220> FEATURE:
<221> NAME/KEY: misc_feature
<222> LOCATION: (6)..(6)
<223> OTHER INFORMATION: Xaa can be Ile or a conservative substitution
      of Ile
<220> FEATURE:
<221> NAME/KEY: misc_feature
<222> LOCATION: (7)..(7)
<223> OTHER INFORMATION: Xaa can be Val or a conservative substitution
      of Val
<220> FEATURE:
<221> NAME/KEY: misc_feature
<222> LOCATION: (8)..(8)
<223> OTHER INFORMATION: Xaa can be Tyr or a conservative substitution
```

```
            of Tyr
<220> FEATURE:
<221> NAME/KEY: misc_feature
<222> LOCATION: (10)..(10)
<223> OTHER INFORMATION: Xaa can be Asn or any other amino acid
<220> FEATURE:
<221> NAME/KEY: misc_feature
<222> LOCATION: (11)..(11)
<223> OTHER INFORMATION: Xaa can be Gly or any other amino acid
<220> FEATURE:
<221> NAME/KEY: misc_feature
<222> LOCATION: (12)..(12)
<223> OTHER INFORMATION: Xaa can be Asn or any other amino acid
<220> FEATURE:
<221> NAME/KEY: misc_feature
<222> LOCATION: (13)..(13)
<223> OTHER INFORMATION: Xaa can be Thr or any other amino acid
<220> FEATURE:
<221> NAME/KEY: misc_feature
<222> LOCATION: (16)..(16)
<223> OTHER INFORMATION: Xaa can be Gly or any other amino acid

<400> SEQUENCE: 45

Arg Ser Ser Gln Ser Xaa Xaa Xaa Ser Xaa Xaa Xaa Xaa Tyr Leu Xaa
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2
<220> FEATURE:
<221> NAME/KEY: misc_feature
<222> LOCATION: (2)..(2)
<223> OTHER INFORMATION: Xaa can be Val or any other amino acid
<220> FEATURE:
<221> NAME/KEY: misc_feature
<222> LOCATION: (6)..(6)
<223> OTHER INFORMATION: Xaa can be Phe or any other amino acid

<400> SEQUENCE: 46

Lys Xaa Ser Asn Arg Xaa Ser
1               5

<210> SEQ ID NO 47
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3
<220> FEATURE:
<221> NAME/KEY: misc_feature
<222> LOCATION: (1)..(1)
<223> OTHER INFORMATION: Xaa can be Phe or any other amino acid
<220> FEATURE:
<221> NAME/KEY: misc_feature
<222> LOCATION: (3)..(3)
<223> OTHER INFORMATION: Xaa can be Gly or any other amino acid
<220> FEATURE:
<221> NAME/KEY: misc_feature
<222> LOCATION: (4)..(4)
<223> OTHER INFORMATION: Xaa can be Ser or any other amino acid
<220> FEATURE:
<221> NAME/KEY: misc_feature
<222> LOCATION: (5)..(5)
<223> OTHER INFORMATION: Xaa can be His or any other amino acid
<220> FEATURE:
<221> NAME/KEY: misc_feature
<222> LOCATION: (6)..(6)
<223> OTHER INFORMATION: Xaa can be Val or any other amino acid
<220> FEATURE:
<221> NAME/KEY: misc_feature
```

```
<222> LOCATION: (9)..(9)
<223> OTHER INFORMATION: Xaa can be Thr or any other amino acid

<400> SEQUENCE: 47

Xaa Gln Xaa Xaa Xaa Xaa Pro Tyr Xaa
1               5

<210> SEQ ID NO 48
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 48

Gly Tyr Thr Phe Thr Asn Tyr Ala Met His
1               5                   10

<210> SEQ ID NO 49
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 49

Met Gly Thr Ile Tyr Pro Gly Asn Asp Asp Thr Lys Tyr Asn Gln Lys
1               5                   10                  15

Phe Gln Gly

<210> SEQ ID NO 50
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 50

Gly Gly Phe Arg Ala Met Asp Tyr
1               5

<210> SEQ ID NO 51
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 51

Arg Ser Ser Gln Ser Leu Leu His Ser Asn Gly Asn Thr Tyr Leu Gly
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2

<400> SEQUENCE: 52

Lys Gly Ser Asn Arg Phe Ser
1               5
```

<210> SEQ ID NO 53
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 53

Phe Gln Ala Ser His Val Pro Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 54

Phe Gln Ala Ser Gln Val Pro Tyr Thr
1               5

<210> SEQ ID NO 55
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 55

Arg Ser Ser Gln Ser Leu Leu His Ser Asn Ala Asn Thr Tyr Leu Gly
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 56

Arg Ser Ser Gln Ser Leu Leu His Ser Asn Ala Tyr Asn Tyr Leu Gly
1               5                   10                  15

<210> SEQ ID NO 57
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 57

Gly Tyr Ser Phe Thr Asn Tyr Asn Ile His
1               5                   10

<210> SEQ ID NO 58
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 58

Met Gly Thr Ile Tyr Pro Gly Asp Ser Asp Thr Arg Tyr Asn Pro Lys
1               5                   10                  15

Phe Gln Gly

<210> SEQ ID NO 59
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 59

Gly Gly Tyr Arg Ala Glu Asp Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 60

Met Gln Gly Ser His Val Pro Tyr
1               5

<210> SEQ ID NO 61
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 61

Met Gly Thr Ile Tyr Pro Gly Asn Ser Asp Thr Ser Tyr Asn Pro Ser
1               5                   10                  15

Phe Gln Gly

<210> SEQ ID NO 62
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 62

Gly Gly Val Arg Ala Met Asp Tyr
1               5

<210> SEQ ID NO 63
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 63

Met Gln Ala Ser Gln Val Pro Tyr Thr
1               5

<210> SEQ ID NO 64
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion VH CDR

<400> SEQUENCE: 64

Gly Tyr Ser Phe Thr Asn Tyr Asn Met His
1               5                   10

<210> SEQ ID NO 65
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion VH CDR

<400> SEQUENCE: 65

Met Gly Thr Ile Tyr Pro Gly Asn Asp Asp Thr Ser Tyr Asn Gln Lys
1               5                   10                  15

Phe Gln Gly

<210> SEQ ID NO 66
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion VH CDR

<400> SEQUENCE: 66

Gly Gly Tyr Arg Ala Met Asp Tyr
1               5

<210> SEQ ID NO 67
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion VL CDR

<400> SEQUENCE: 67

Arg Ser Ser Gly Ser Ile Val Tyr Ser Asn Gly Asn Thr Tyr Leu Gly
1               5                   10                  15

<210> SEQ ID NO 68
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion VL CDR

<400> SEQUENCE: 68

Lys Val Ser Asn Arg Phe Ser
1               5

<210> SEQ ID NO 69
<211> LENGTH: 9
<212> TYPE: PRT
<213> ORGANISM: Artificial Sequence
<220> FEATURE:

<223> OTHER INFORMATION: anti-CD47 antibody molecule or antigen-binding
      portion VL CDR

<400> SEQUENCE: 69

Phe Gln Gly Ser His Val Pro Tyr Thr
1               5

<210> SEQ ID NO 70
<211> LENGTH: 40
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
                20                  25                  30

Asn Gly Asn Thr Tyr Leu Gly Trp
            35                  40

<210> SEQ ID NO 71
<211> LENGTH: 40
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Asn Met His Trp Val Arg Gln Ala
            35                  40

<210> SEQ ID NO 72
<211> LENGTH: 37
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 72

Met Glu Leu Ser Ser Leu Arg Ser Glu Asp Thr Ala Val Tyr Tyr Cys
1               5                   10                  15

Ala Arg Gly Gly Tyr Arg Ala Met Asp Tyr Trp Gly Gln Gly Thr Leu
                20                  25                  30

Val Thr Val Ser Ser
            35

<210> SEQ ID NO 73
<211> LENGTH: 77
<212> TYPE: PRT
<213> ORGANISM: Artificial Sequence
<220> FEATURE:
<223> OTHER INFORMATION: anti-CD47 antibody molecule or antigen-binding
      portion LCDR2

<400> SEQUENCE: 73

```
Asp Ile Val Met Thr Gln Ser Pro Leu Ser Leu Pro Val Thr Pro Gly
1               5                  10                 15

Glu Pro Ala Ser Ile Ser Cys Arg Ser Ser Gln Ser Leu Leu His Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Gly Ser Asn Arg Phe Ser Gly Val Pro
    50                  55                  60

Asp Arg Phe Ser Gly Ser Gly Ser Gly Thr Asp Phe Thr
65                  70                  75

<210> SEQ ID NO 74
<211> LENGTH: 35
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 74

Leu Lys Ile Ser Arg Val Glu Ala Glu Asp Val Gly Val Tyr Tyr Cys
1               5                  10                 15

Phe Gln Ala Ser His Val Pro Tyr Thr Phe Gly Gln Gly Thr Lys Leu
            20                  25                  30

Glu Ile Lys
        35

<210> SEQ ID NO 75
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (1)..(1)
<223> OTHER INFORMATION: Xaa can be Met or a conservative substitution
      of Met
<220> FEATURE:
<221> NAME/KEY: misc_feature
<222> LOCATION: (2)..(2)
<223> OTHER INFORMATION: Xaa can be Gly or a conservative substitution
      of Gly
<220> FEATURE:
<221> NAME/KEY: misc_feature
<222> LOCATION: (3)..(3)
<223> OTHER INFORMATION: Xaa can be Thr or any other amino acid
<220> FEATURE:
<221> NAME/KEY: misc_feature
<222> LOCATION: (8)..(8)
<223> OTHER INFORMATION: Xaa can be Asn or any other amino acid
<220> FEATURE:
<221> NAME/KEY: misc_feature
<222> LOCATION: (9)..(9)
<223> OTHER INFORMATION: Xaa can be Asp or any other amino acid
<220> FEATURE:
<221> NAME/KEY: misc_feature
<222> LOCATION: (10)..(10)
<223> OTHER INFORMATION: Xaa can be Asp or any other amino acid
<220> FEATURE:
<221> NAME/KEY: misc_feature
<222> LOCATION: (12)..(12)
<223> OTHER INFORMATION: Xaa can be Ser or any other amino acid
<220> FEATURE:
<221> NAME/KEY: misc_feature
<222> LOCATION: (14)..(14)
<223> OTHER INFORMATION: Xaa can be Asn or any other amino acid
<220> FEATURE:
<221> NAME/KEY: misc_feature
```

```
<222> LOCATION: (15)..(15)
<223> OTHER INFORMATION: Xaa can be Gln or any other amino acid
<220> FEATURE:
<221> NAME/KEY: misc_feature
<222> LOCATION: (16)..(16)
<223> OTHER INFORMATION: Xaa can be Lys or any other amino acid

<400> SEQUENCE: 75

Xaa Xaa Xaa Ile Tyr Pro Gly Xaa Xaa Xaa Thr Xaa Tyr Xaa Xaa Xaa
1               5                   10                  15

Phe Gln Gly

<210> SEQ ID NO 76
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1
<220> FEATURE:
<221> NAME/KEY: misc_feature
<222> LOCATION: (3)..(3)
<223> OTHER INFORMATION: Xaa can be Thr or Ser
<220> FEATURE:
<221> NAME/KEY: misc_feature
<222> LOCATION: (6)..(6)
<223> OTHER INFORMATION: Xaa can be Asn, Ser or Asp
<220> FEATURE:
<221> NAME/KEY: misc_feature
<222> LOCATION: (8)..(8)
<223> OTHER INFORMATION: Xaa can be Asn, Ser or Ala
<220> FEATURE:
<221> NAME/KEY: misc_feature
<222> LOCATION: (9)..(9)
<223> OTHER INFORMATION: Xaa can be Met or Ile
<220> FEATURE:
<221> NAME/KEY: misc_feature
<222> LOCATION: (10)..(10)
<223> OTHER INFORMATION: Xaa can be His or Gly

<400> SEQUENCE: 76

Gly Tyr Xaa Phe Thr Xaa Tyr Xaa Xaa Xaa
1               5                   10

<210> SEQ ID NO 77
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (1)..(1)
<223> OTHER INFORMATION: Xaa can be Met, Ile or Val
<220> FEATURE:
<221> NAME/KEY: misc_feature
<222> LOCATION: (2)..(2)
<223> OTHER INFORMATION: Xaa can be Gly, Ala or Ser
<220> FEATURE:
<221> NAME/KEY: misc_feature
<222> LOCATION: (3)..(3)
<223> OTHER INFORMATION: Xaa can be Thr or Ile
<220> FEATURE:
<221> NAME/KEY: misc_feature
<222> LOCATION: (8)..(8)
<223> OTHER INFORMATION: Xaa can be Asn or Asp
<220> FEATURE:
<221> NAME/KEY: misc_feature
<222> LOCATION: (9)..(9)
<223> OTHER INFORMATION: Xaa can be Asp or Ser
<220> FEATURE:
<221> NAME/KEY: misc_feature
<222> LOCATION: (10)..(10)
```

<223> OTHER INFORMATION: Xaa can be Asp or Asn
<220> FEATURE:
<221> NAME/KEY: misc_feature
<222> LOCATION: (12)..(12)
<223> OTHER INFORMATION: Xaa can be Ser, Lys or Arg
<220> FEATURE:
<221> NAME/KEY: misc_feature
<222> LOCATION: (14)..(14)
<223> OTHER INFORMATION: Xaa can be Asn, Ser or His
<220> FEATURE:
<221> NAME/KEY: misc_feature
<222> LOCATION: (15)..(15)
<223> OTHER INFORMATION: Xaa can be Gln, Pro or His
<220> FEATURE:
<221> NAME/KEY: misc_feature
<222> LOCATION: (16)..(16)
<223> OTHER INFORMATION: Xaa can be Lys or Ser
<220> FEATURE:
<221> NAME/KEY: misc_feature
<222> LOCATION: (18)..(18)
<223> OTHER INFORMATION: Xaa can be Lys or Gln
<220> FEATURE:
<221> NAME/KEY: misc_feature
<222> LOCATION: (19)..(19)
<223> OTHER INFORMATION: Xaa can be Asp or Gly

<400> SEQUENCE: 77

Xaa Xaa Xaa Ile Tyr Pro Gly Xaa Xaa Xaa Thr Xaa Tyr Xaa Xaa Xaa
1               5                   10                  15

Phe Xaa Xaa

<210> SEQ ID NO 78
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3
<220> FEATURE:
<221> NAME/KEY: misc_feature
<222> LOCATION: (1)..(1)
<223> OTHER INFORMATION: Xaa can be Gly or Gln
<220> FEATURE:
<221> NAME/KEY: misc_feature
<222> LOCATION: (3)..(3)
<223> OTHER INFORMATION: Xaa can be Tyr, Ala, Cys, Asp, Glu, Phe, Gly,
      His, Ile, Lys, Leu, Met, Asn, Gln, Arg, Ser, Thr, Val or Trp
<220> FEATURE:
<221> NAME/KEY: misc_feature
<222> LOCATION: (5)..(5)
<223> OTHER INFORMATION: Xaa can be Ala, Ile, Thr, Val or Trp
<220> FEATURE:
<221> NAME/KEY: misc_feature
<222> LOCATION: (6)..(6)
<223> OTHER INFORMATION: Xaa can be Met, Ala, Glu, Lys, Leu, Pro, Gln,
      Arg, Ser, Thr, Val or Trp

<400> SEQUENCE: 78

Xaa Gly Xaa Arg Xaa Xaa Asp Tyr
1               5

<210> SEQ ID NO 79
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1
<220> FEATURE:
<221> NAME/KEY: misc_feature
<222> LOCATION: (3)..(3)
<223> OTHER INFORMATION: Xaa can be Thr or Ser
<220> FEATURE:
<221> NAME/KEY: misc_feature -continued

```
<222> LOCATION: (6)..(6)
<223> OTHER INFORMATION: Xaa can be Asn or Asp
<220> FEATURE:
<221> NAME/KEY: misc_feature
<222> LOCATION: (8)..(8)
<223> OTHER INFORMATION: Xaa can be Asn or Ala
<220> FEATURE:
<221> NAME/KEY: misc_feature
<222> LOCATION: (9)..(9)
<223> OTHER INFORMATION: Xaa can be Met or Ile

<400> SEQUENCE: 79

Gly Tyr Xaa Phe Thr Xaa Tyr Xaa Xaa His
1               5                   10

<210> SEQ ID NO 80
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (8)..(8)
<223> OTHER INFORMATION: Xaa can be Asn or Asp
<220> FEATURE:
<221> NAME/KEY: misc_feature
<222> LOCATION: (9)..(9)
<223> OTHER INFORMATION: Xaa can be Asp or Ser
<220> FEATURE:
<221> NAME/KEY: misc_feature
<222> LOCATION: (10)..(10)
<223> OTHER INFORMATION: Xaa can be Asp or Asn
<220> FEATURE:
<221> NAME/KEY: misc_feature
<222> LOCATION: (12)..(12)
<223> OTHER INFORMATION: Xaa can be Ser, Lys or Arg
<220> FEATURE:
<221> NAME/KEY: misc_feature
<222> LOCATION: (14)..(14)
<223> OTHER INFORMATION: Xaa can be Asn or Ser
<220> FEATURE:
<221> NAME/KEY: misc_feature
<222> LOCATION: (15)..(15)
<223> OTHER INFORMATION: Xaa can be Gln, Pro or His
<220> FEATURE:
<221> NAME/KEY: misc_feature
<222> LOCATION: (16)..(16)
<223> OTHER INFORMATION: Xaa can be Lys or Ser

<400> SEQUENCE: 80

Met Gly Thr Ile Tyr Pro Gly Xaa Xaa Xaa Thr Xaa Tyr Xaa Xaa Xaa
1               5                   10                  15

Phe Gln Gly

<210> SEQ ID NO 81
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3
<220> FEATURE:
<221> NAME/KEY: misc_feature
<222> LOCATION: (3)..(3)
<223> OTHER INFORMATION: Xaa can be Tyr, Glu, Phe, Ile, Lys, Asn or Val
<220> FEATURE:
<221> NAME/KEY: misc_feature
<222> LOCATION: (6)..(6)
<223> OTHER INFORMATION: Xaa can be Met, Glu or Gln

<400> SEQUENCE: 81
```

Gly Gly Xaa Arg Ala Xaa Asp Tyr
1               5

<210> SEQ ID NO 82
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1
<220> FEATURE:
<221> NAME/KEY: misc_feature
<222> LOCATION: (7)..(7)
<223> OTHER INFORMATION: Xaa can be Val or Leu
<220> FEATURE:
<221> NAME/KEY: misc_feature
<222> LOCATION: (8)..(8)
<223> OTHER INFORMATION: Xaa can be Tyr or His
<220> FEATURE:
<221> NAME/KEY: misc_feature
<222> LOCATION: (10)..(10)
<223> OTHER INFORMATION: Xaa can be Asn, Gly, Ser or Lys
<220> FEATURE:
<221> NAME/KEY: misc_feature
<222> LOCATION: (11)..(11)
<223> OTHER INFORMATION: Xaa can be Gly, Ala or Tyr
<220> FEATURE:
<221> NAME/KEY: misc_feature
<222> LOCATION: (12)..(12)
<223> OTHER INFORMATION: Xaa can be Asn or Tyr
<220> FEATURE:
<221> NAME/KEY: misc_feature
<222> LOCATION: (13)..(13)
<223> OTHER INFORMATION: Xaa can be Thr or Asn
<220> FEATURE:
<221> NAME/KEY: misc_feature
<222> LOCATION: (16)..(16)
<223> OTHER INFORMATION: Xaa can be Gly or Asp

<400> SEQUENCE: 82

Arg Ser Ser Gln Ser Leu Xaa Xaa Ser Xaa Xaa Xaa Xaa Tyr Leu Xaa
1               5                   10                  15

<210> SEQ ID NO 83
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2
<220> FEATURE:
<221> NAME/KEY: misc_feature
<222> LOCATION: (6)..(6)
<223> OTHER INFORMATION: Xaa can be Phe or Ala

<400> SEQUENCE: 83

Lys Gly Ser Asn Arg Xaa Ser
1               5

<210> SEQ ID NO 84
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3
<220> FEATURE:
<221> NAME/KEY: misc_feature
<222> LOCATION: (1)..(1)
<223> OTHER INFORMATION: Xaa can be Phe or Met
<220> FEATURE:
<221> NAME/KEY: misc_feature
<222> LOCATION: (3)..(3)
<223> OTHER INFORMATION: Xaa can be Gly or Ala

```
<220> FEATURE:
<221> NAME/KEY: misc_feature
<222> LOCATION: (5)..(5)
<223> OTHER INFORMATION: Xaa can be His or Gln
<220> FEATURE:
<221> NAME/KEY: misc_feature
<222> LOCATION: (9)..(9)
<223> OTHER INFORMATION: Xaa can be Thr or Ile

<400> SEQUENCE: 84

Xaa Gln Xaa Ser Xaa Val Pro Tyr Xaa
1               5

<210> SEQ ID NO 85
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1
<220> FEATURE:
<221> NAME/KEY: misc_feature
<222> LOCATION: (10)..(10)
<223> OTHER INFORMATION: Xaa can be Asn or Lys
<220> FEATURE:
<221> NAME/KEY: misc_feature
<222> LOCATION: (11)..(11)
<223> OTHER INFORMATION: Xaa can be Gly, Ala or Tyr
<220> FEATURE:
<221> NAME/KEY: misc_feature
<222> LOCATION: (12)..(12)
<223> OTHER INFORMATION: Xaa can be Asn, Gln or Tyr
<220> FEATURE:
<221> NAME/KEY: misc_feature
<222> LOCATION: (13)..(13)
<223> OTHER INFORMATION: Xaa can be Thr or Asn

<400> SEQUENCE: 85

Arg Ser Ser Gln Ser Leu Leu His Ser Xaa Xaa Xaa Xaa Tyr Leu Gly
1               5                   10                  15

<210> SEQ ID NO 86
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2
<220> FEATURE:
<221> NAME/KEY: misc_feature
<222> LOCATION: (2)..(2)
<223> OTHER INFORMATION: Xaa can be Val or Gly
<220> FEATURE:
<221> NAME/KEY: misc_feature
<222> LOCATION: (6)..(6)
<223> OTHER INFORMATION: Xaa can be Phe, Ala or Ser

<400> SEQUENCE: 86

Lys Xaa Ser Asn Arg Xaa Ser
1               5

<210> SEQ ID NO 87
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3
<220> FEATURE:
<221> NAME/KEY: misc_feature
<222> LOCATION: (1)..(1)
<223> OTHER INFORMATION: Xaa can be Phe, Leu or Met
<220> FEATURE:
```

```
<221> NAME/KEY: misc_feature
<222> LOCATION: (3)..(3)
<223> OTHER INFORMATION: Xaa can be Gly or Ala
<220> FEATURE:
<221> NAME/KEY: misc_feature
<222> LOCATION: (4)..(4)
<223> OTHER INFORMATION: Xaa can be Ser, Thr, Leu or Met
<220> FEATURE:
<221> NAME/KEY: misc_feature
<222> LOCATION: (5)..(5)
<223> OTHER INFORMATION: Xaa can be His, Gln or Arg
<220> FEATURE:
<221> NAME/KEY: misc_feature
<222> LOCATION: (6)..(6)
<223> OTHER INFORMATION: Xaa can be Val, Ile or Thr
<220> FEATURE:
<221> NAME/KEY: misc_feature
<222> LOCATION: (9)..(9)
<223> OTHER INFORMATION: Xaa can be Thr or Ile

<400> SEQUENCE: 87

Xaa Gln Xaa Xaa Xaa Xaa Pro Tyr Xaa
1               5

<210> SEQ ID NO 88
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 88

Gly Tyr Thr Phe Thr Asp Tyr Asn Met His
1               5                   10

<210> SEQ ID NO 89
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 89

Gly Tyr Thr Phe Thr Asn Tyr Asn Ile His
1               5                   10

<210> SEQ ID NO 90
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 90

Met Gly Thr Ile Tyr Pro Gly Asn Asp Asp Thr Ser Tyr Ser Gln Lys
1               5                   10                  15

Phe Gln Gly

<210> SEQ ID NO 91
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 91
```

```
Met Gly Thr Ile Tyr Pro Gly Asn Asp Asp Thr Lys Tyr Ser Gln Lys
1               5                   10                  15

Phe Gln Gly

<210> SEQ ID NO 92
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 92

Met Gly Thr Ile Tyr Pro Gly Asn Ser Asp Thr Ser Tyr Asn Pro Lys
1               5                   10                  15

Phe Gln Gly

<210> SEQ ID NO 93
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 93

Gly Gly Lys Arg Ala Met Asp Tyr
1               5

<210> SEQ ID NO 94
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 94

Met Gly Thr Ile Tyr Pro Gly Asp Ser Asp Thr Ser Tyr Asn Pro Lys
1               5                   10                  15

Phe Gln Gly

<210> SEQ ID NO 95
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 95

Gly Gly Tyr Arg Ala Gln Asp Tyr
1               5

<210> SEQ ID NO 96
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 96

Met Gln Ala Ser His Val Pro Tyr Thr
1               5
```

<210> SEQ ID NO 97
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 97

Met Gln Gly Ser His Val Pro Tyr Thr
1               5

<210> SEQ ID NO 98
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 98

Met Gly Thr Ile Tyr Pro Gly Asp Ser Asp Thr Arg Tyr Asn Gln Lys
1               5                   10                  15

Phe Gln Gly

<210> SEQ ID NO 99
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 99

Gly Gly Ile Arg Ala Met Asp Tyr
1               5

<210> SEQ ID NO 100
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 100

Phe Gln Gly Ser His Val Pro Tyr Ile
1               5

<210> SEQ ID NO 101
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 101

Met Gly Thr Ile Tyr Pro Gly Asn Ser Asp Thr Arg Tyr Asn Pro Lys
1               5                   10                  15

Phe Gln Gly

<210> SEQ ID NO 102
<211> LENGTH: 9
<212> TYPE: PRT

```
<213> ORGANISM: Artificial Sequence
<220> FEATURE:
<223> OTHER INFORMATION: human germline peptide sequence with high MHC
      class II binding affinity in the HCDR2

<400> SEQUENCE: 102

Phe Gln Gly Gln Val Thr Ile Ser Ala
1               5

<210> SEQ ID NO 103
<211> LENGTH: 9
<212> TYPE: PRT
<213> ORGANISM: Artificial Sequence
<220> FEATURE:
<223> OTHER INFORMATION: human germline peptide sequence with high MHC
      class II binding affinity in the HCDR2

<400> SEQUENCE: 103

Phe Gln Gly Arg Val Thr Ile Thr Ala
1               5

<210> SEQ ID NO 104
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1
<220> FEATURE:
<221> NAME/KEY: misc_feature
<222> LOCATION: (6)..(6)
<223> OTHER INFORMATION: Xaa can be Asn or a conservative substitution
      of Asn
<220> FEATURE:
<221> NAME/KEY: misc_feature
<222> LOCATION: (8)..(8)
<223> OTHER INFORMATION: Xaa can be Asn or any other amino acid
<220> FEATURE:
<221> NAME/KEY: misc_feature
<222> LOCATION: (9)..(9)
<223> OTHER INFORMATION: Xaa can be Met or a conservative substitution
      of Met
<220> FEATURE:
<221> NAME/KEY: misc_feature
<222> LOCATION: (10)..(10)
<223> OTHER INFORMATION: Xaa can be His or any other amino acid

<400> SEQUENCE: 104

Gly Tyr Thr Phe Thr Xaa Tyr Xaa Xaa Xaa
1               5                   10

<210> SEQ ID NO 105
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
<220> FEATURE:
<221> NAME/KEY: misc_feature
<222> LOCATION: (3)..(3)
<223> OTHER INFORMATION: Xaa can be Thr or any other amino acid
<220> FEATURE:
<221> NAME/KEY: misc_feature
<222> LOCATION: (8)..(8)
<223> OTHER INFORMATION: Xaa can be Asn or a conservative substitution
      of Asn
<220> FEATURE:
<221> NAME/KEY: misc_feature
<222> LOCATION: (9)..(9)
<223> OTHER INFORMATION: Xaa can be Asp or any other amino acid
<220> FEATURE:
<221> NAME/KEY: misc_feature
```

```
<222> LOCATION: (10)..(10)
<223> OTHER INFORMATION: Xaa can be Asp or any other amino acid
<220> FEATURE:
<221> NAME/KEY: misc_feature
<222> LOCATION: (12)..(12)
<223> OTHER INFORMATION: Xaa can be Ser or any other amino acid
<220> FEATURE:
<221> NAME/KEY: misc_feature
<222> LOCATION: (14)..(14)
<223> OTHER INFORMATION: Xaa can be Asn or any other amino acid
<220> FEATURE:
<221> NAME/KEY: misc_feature
<222> LOCATION: (15)..(15)
<223> OTHER INFORMATION: Xaa can be Gln or any other amino acid
<220> FEATURE:
<221> NAME/KEY: misc_feature
<222> LOCATION: (16)..(16)
<223> OTHER INFORMATION: Xaa can be Lys or any other amino acid

<400> SEQUENCE: 105

Met Gly Xaa Ile Tyr Pro Gly Xaa Xaa Xaa Thr Xaa Tyr Xaa Xaa Xaa
1               5                   10                  15

Phe Gln Gly

<210> SEQ ID NO 106
<211> LENGTH: 9
<212> TYPE: PRT
<213> ORGANISM: Artificial Sequence
<220> FEATURE:
<223> OTHER INFORMATION: TCED+ peptide

<400> SEQUENCE: 106

Ile Val Tyr Ser Asn Gly Asn Thr Tyr
1               5

<210> SEQ ID NO 107
<211> LENGTH: 9
<212> TYPE: PRT
<213> ORGANISM: Artificial Sequence
<220> FEATURE:
<223> OTHER INFORMATION: HAF and TCED+ peptide

<400> SEQUENCE: 107

Tyr Asn Met His Trp Val Arg Gln Ala
1               5

<210> SEQ ID NO 108
<211> LENGTH: 9
<212> TYPE: PRT
<213> ORGANISM: Artificial Sequence
<220> FEATURE:
<223> OTHER INFORMATION: TCED+ peptide

<400> SEQUENCE: 108

Tyr Ala Met His Trp Val Arg Gln Ala
1               5

<210> SEQ ID NO 109
<211> LENGTH: 9
<212> TYPE: PRT
<213> ORGANISM: Artificial Sequence
<220> FEATURE:
<223> OTHER INFORMATION: TCED+ peptide

<400> SEQUENCE: 109

Tyr Asn Ile His Trp Val Arg Gln Ala
1               5
```

-continued

```
<210> SEQ ID NO 110
<211> LENGTH: 9
<212> TYPE: PRT
<213> ORGANISM: Artificial Sequence
<220> FEATURE:
<223> OTHER INFORMATION: TCED+ peptide

<400> SEQUENCE: 110

Tyr Arg Ala Met Asp Tyr Trp Gly Gln
1               5

<210> SEQ ID NO 111
<211> LENGTH: 9
<212> TYPE: PRT
<213> ORGANISM: Artificial Sequence
<220> FEATURE:
<223> OTHER INFORMATION: TCED+ peptide

<400> SEQUENCE: 111

Tyr Arg Ala Glu Asp Tyr Trp Gly Gln
1               5

<210> SEQ ID NO 112
<211> LENGTH: 9
<212> TYPE: PRT
<213> ORGANISM: Artificial Sequence
<220> FEATURE:
<223> OTHER INFORMATION: HAF peptide

<400> SEQUENCE: 112

Leu Ile Tyr Lys Gly Ser Asn Arg Phe
1               5

<210> SEQ ID NO 113
<211> LENGTH: 9
<212> TYPE: PRT
<213> ORGANISM: Artificial Sequence
<220> FEATURE:
<223> OTHER INFORMATION: HAF peptide

<400> SEQUENCE: 113

Val Gly Val Tyr Tyr Cys Phe Gln Ala
1               5

<210> SEQ ID NO 114
<211> LENGTH: 10
<212> TYPE: PRT
<213> ORGANISM: Mus musculus

<400> SEQUENCE: 114

Gly Tyr Thr Phe Thr Asn Tyr Asn Met His
1               5                   10

<210> SEQ ID NO 115
<211> LENGTH: 5
<212> TYPE: PRT
<213> ORGANISM: Mus musculus

<400> SEQUENCE: 115

Asn Tyr Asn Met His
1               5

<210> SEQ ID NO 116
<211> LENGTH: 7
<212> TYPE: PRT
<213> ORGANISM: Mus musculus
```

```
<400> SEQUENCE: 116

Gly Tyr Thr Phe Thr Asn Tyr
1               5

<210> SEQ ID NO 117
<211> LENGTH: 8
<212> TYPE: PRT
<213> ORGANISM: Mus musculus

<400> SEQUENCE: 117

Gly Tyr Thr Phe Thr Asn Tyr Asn
1               5

<210> SEQ ID NO 118
<211> LENGTH: 6
<212> TYPE: PRT
<213> ORGANISM: Mus musculus

<400> SEQUENCE: 118

Thr Asn Tyr Asn Met His
1               5

<210> SEQ ID NO 119
<211> LENGTH: 19
<212> TYPE: PRT
<213> ORGANISM: Mus musculus

<400> SEQUENCE: 119

Met Gly Thr Ile Tyr Pro Gly Asn Asp Asp Thr Ser Tyr Asn Gln Lys
1               5                   10                  15

Phe Lys Asp

<210> SEQ ID NO 120
<211> LENGTH: 17
<212> TYPE: PRT
<213> ORGANISM: Mus musculus

<400> SEQUENCE: 120

Thr Ile Tyr Pro Gly Asn Asp Asp Thr Ser Tyr Asn Gln Lys Phe Lys
1               5                   10                  15

Asp

<210> SEQ ID NO 121
<211> LENGTH: 6
<212> TYPE: PRT
<213> ORGANISM: Mus musculus

<400> SEQUENCE: 121

Tyr Pro Gly Asn Asp Asp
1               5

<210> SEQ ID NO 122
<211> LENGTH: 8
<212> TYPE: PRT
<213> ORGANISM: Mus musculus

<400> SEQUENCE: 122

Ile Tyr Pro Gly Asn Asp Asp Thr
1               5

<210> SEQ ID NO 123
<211> LENGTH: 16
<212> TYPE: PRT
```

<213> ORGANISM: Mus musculus

<400> SEQUENCE: 123

Ile Tyr Pro Gly Asn Asp Asp Thr Ser Tyr Asn Gln Lys Phe Lys Asp
1               5                   10                  15

<210> SEQ ID NO 124
<211> LENGTH: 10
<212> TYPE: PRT
<213> ORGANISM: Mus musculus

<400> SEQUENCE: 124

Thr Ile Tyr Pro Gly Asn Asp Asp Thr Ser
1               5                   10

<210> SEQ ID NO 125
<211> LENGTH: 12
<212> TYPE: PRT
<213> ORGANISM: Mus musculus

<400> SEQUENCE: 125

Met Gly Thr Ile Tyr Pro Gly Asn Asp Asp Thr Ser
1               5                   10

<210> SEQ ID NO 126
<211> LENGTH: 8
<212> TYPE: PRT
<213> ORGANISM: Mus musculus

<400> SEQUENCE: 126

Gly Gly Tyr Arg Ala Met Asp Tyr
1               5

<210> SEQ ID NO 127
<211> LENGTH: 10
<212> TYPE: PRT
<213> ORGANISM: Mus musculus

<400> SEQUENCE: 127

Ala Arg Gly Gly Tyr Arg Ala Met Asp Tyr
1               5                   10

<210> SEQ ID NO 128
<211> LENGTH: 7
<212> TYPE: PRT
<213> ORGANISM: Mus musculus

<400> SEQUENCE: 128

Gly Gly Tyr Arg Ala Met Asp
1               5

<210> SEQ ID NO 129
<211> LENGTH: 9
<212> TYPE: PRT
<213> ORGANISM: Mus musculus

<400> SEQUENCE: 129

Ala Arg Gly Gly Tyr Arg Ala Met Asp
1               5

<210> SEQ ID NO 130
<211> LENGTH: 16
<212> TYPE: PRT
<213> ORGANISM: Mus musculus

<400> SEQUENCE: 130

Arg Ser Ser Gln Ser Ile Val Tyr Ser Asn Gly Asn Thr Tyr Leu Gly
1               5                   10                  15

<210> SEQ ID NO 131
<211> LENGTH: 11
<212> TYPE: PRT
<213> ORGANISM: Mus musculus

<400> SEQUENCE: 131

Gln Ser Ile Val Tyr Ser Asn Gly Asn Thr Tyr
1               5                   10

<210> SEQ ID NO 132
<211> LENGTH: 13
<212> TYPE: PRT
<213> ORGANISM: Mus musculus

<400> SEQUENCE: 132

Ser Ser Gln Ser Ile Val Tyr Ser Asn Gly Asn Thr Tyr
1               5                   10

<210> SEQ ID NO 133
<211> LENGTH: 12
<212> TYPE: PRT
<213> ORGANISM: Mus musculus

<400> SEQUENCE: 133

Val Tyr Ser Asn Gly Asn Thr Tyr Leu Gly Trp Tyr
1               5                   10

<210> SEQ ID NO 134
<211> LENGTH: 7
<212> TYPE: PRT
<213> ORGANISM: Mus musculus

<400> SEQUENCE: 134

Lys Val Ser Asn Arg Phe Ser
1               5

<210> SEQ ID NO 135
<211> LENGTH: 10
<212> TYPE: PRT
<213> ORGANISM: Mus musculus

<400> SEQUENCE: 135

Ala Leu Ile Tyr Lys Val Ser Asn Arg Phe
1               5                   10

<210> SEQ ID NO 136
<211> LENGTH: 9
<212> TYPE: PRT
<213> ORGANISM: Mus musculus

<400> SEQUENCE: 136

Phe Gln Gly Ser His Val Pro Tyr Thr
1               5

<210> SEQ ID NO 137
<211> LENGTH: 6
<212> TYPE: PRT
<213> ORGANISM: Mus musculus

<400> SEQUENCE: 137

Gly Ser His Val Pro Tyr
1               5

<210> SEQ ID NO 138
<211> LENGTH: 8
<212> TYPE: PRT
<213> ORGANISM: Mus musculus

<400> SEQUENCE: 138

Phe Gln Gly Ser His Val Pro Tyr
1               5

<210> SEQ ID NO 139
<211> LENGTH: 117
<212> TYPE: PRT
<213> ORGANISM: Mus musculus

<400> SEQUENCE: 139

Gln Val Gln Leu Gln Gln Pro Gly Ala Glu Leu Val Lys Pro Gly Ala
1               5                   10                  15

Ser Val Met Met Ser Cys Lys Ala Ser Gly Tyr Thr Phe Thr Asn Tyr
            20                  25                  30

Asn Met His Trp Val Lys Gln Thr Pro Gly Gln Gly Leu Glu Trp Ile
        35                  40                  45

Gly Thr Ile Tyr Pro Gly Asn Asp Asp Thr Ser Tyr Asn Gln Lys Phe
    50                  55                  60

Lys Asp Lys Ala Thr Leu Thr Ala Asp Lys Ser Ser Ala Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Arg Ala Met Asp Tyr Trp Gly Gln Gly Thr Ser
            100                 105                 110

Val Thr Val Ser Ser
        115

<210> SEQ ID NO 140
<211> LENGTH: 117
<212> TYPE: PRT
<213> ORGANISM: Artificial Sequence
<220> FEATURE:
<223> OTHER INFORMATION: h5F9G4-VH IGHV1-3

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115

<210> SEQ ID NO 141
<211> LENGTH: 117
<212> TYPE: PRT
<213> ORGANISM: Artificial Sequence
<220> FEATURE:
<223> OTHER INFORMATION: VH graft IGHV5-51

<400> SEQUENCE: 141

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Asn Met His Trp Val Arg Gln Met Pro Gly Lys Gly Leu Glu Trp Met
        35                  40                  45

Gly Thr Ile Tyr Pro Gly Asn Asp Asp Thr Ser Tyr Asn Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115

<210> SEQ ID NO 142
<211> LENGTH: 112
<212> TYPE: PRT
<213> ORGANISM: Mus musculus

<400> SEQUENCE: 142

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Tyr Thr Phe Gly Gly Gly Thr Lys Val Glu Ile Lys
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: h5F9G4-VL IGKV2-28

<400> SEQUENCE: 143

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

```
Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 144
<211> LENGTH: 112
<212> TYPE: PRT
<213> ORGANISM: Artificial Sequence
<220> FEATURE:
<223> OTHER INFORMATION: IGKV2-28

<400> SEQUENCE: 144

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 145
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 145

Arg Ser Ser Gln Ser Leu Leu His Ser Gly Gly Asn Thr Tyr Leu Asp
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 146

Arg Ser Ser Gln Ser Leu Leu His Ser Gly Gly Asn Thr Tyr Leu Gly
1               5                   10                  15

<210> SEQ ID NO 147
<211> LENGTH: 16
<212> TYPE: PRT
```

```
<213> ORGANISM: Artificial Sequence
<220> FEATURE:
<223> OTHER INFORMATION: anti-CD47 antibody molecule or antigen-binding
      portion LCDR1

<400> SEQUENCE: 147

Arg Ser Ser Gln Ser Leu Leu His Ser Gly Tyr Asn Thr Tyr Leu Gly
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 148

Arg Ser Ser Gln Ser Leu Leu His Ser Asn Gly Asn Thr Tyr Leu Asp
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 149

Arg Ser Ser Gln Ser Leu Leu His Ser Asn Tyr Asn Thr Tyr Leu Gly
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 150

Arg Ser Ser Gln Ser Leu Leu Gln Ser Asn Gly Asn Thr Tyr Leu Gly
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 151

Arg Ser Ser Gln Ser Leu Leu Tyr Ser Gly Gly Asn Thr Tyr Leu Gly
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 152

Arg Ser Ser Gln Ser Leu Leu Tyr Ser Asn Gly Asn Thr Tyr Leu Gly
1               5                   10                  15
```

<210> SEQ ID NO 153
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 153

Arg Ser Ser Gln Ser Leu Val His Ser Gly Gly Asn Thr Tyr Leu Gly
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 154

Arg Ser Ser Gln Ser Leu Val His Ser Gly Tyr Asn Thr Tyr Leu Gly
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 155

Arg Ser Ser Gln Ser Leu Val His Ser Asn Gly Asn Thr Tyr Leu Asp
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 156

Arg Ser Ser Gln Ser Leu Val His Ser Asn Gly Asn Thr Tyr Leu Gly
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 157

Arg Ser Ser Gln Ser Leu Val His Ser Asn Gly Gln Thr Tyr Leu Gly
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

-continued

<400> SEQUENCE: 158

Arg Ser Ser Gln Ser Leu Val His Ser Asn Tyr Asn Thr Tyr Leu Gly
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 159

Arg Ser Ser Gln Ser Leu Val His Ser Ser Gly Asn Thr Tyr Leu Gly
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 160

Arg Ser Ser Gln Ser Leu Val Gln Ser Asn Gly Asn Thr Tyr Leu Gly
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 161

Arg Ser Ser Gln Ser Leu Val Tyr Ser Asn Gly Asn Thr Tyr Leu Gly
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 162

Arg Ser Ser Gln Ser Leu Val Tyr Ser Asn Tyr Asn Thr Tyr Leu Gly
1               5                   10                  15

<210> SEQ ID NO 163
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2

<400> SEQUENCE: 163

Lys Val Ser Asn Arg Ala Ser
1               5

<210> SEQ ID NO 164
<211> LENGTH: 7

```
<212> TYPE: PRT
<213> ORGANISM: Artificial Sequence
<220> FEATURE:
<223> OTHER INFORMATION: anti-CD47 antibody molecule or antigen-binding
      portion LCDR2

<400> SEQUENCE: 164

Lys Val Ser Asn Arg Ser Ser
1               5

<210> SEQ ID NO 165
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 165

Phe Gln Ala Leu His Val Pro Tyr Thr
1               5

<210> SEQ ID NO 166
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 166

Phe Gln Ala Met Gln Thr Pro Tyr Thr
1               5

<210> SEQ ID NO 167
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 167

Phe Gln Ala Ser His Ile Pro Tyr Thr
1               5

<210> SEQ ID NO 168
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 168

Phe Gln Ala Ser His Thr Pro Tyr Thr
1               5

<210> SEQ ID NO 169
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 169

Phe Gln Ala Ser Gln Ile Pro Tyr Thr
```

1               5

<210> SEQ ID NO 170
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 170

Phe Gln Ala Ser Gln Thr Pro Tyr Thr
1               5

<210> SEQ ID NO 171
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 171

Phe Gln Ala Ser Arg Val Pro Tyr Thr
1               5

<210> SEQ ID NO 172
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 172

Phe Gln Ala Thr Gln Val Pro Tyr Thr
1               5

<210> SEQ ID NO 173
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 173

Phe Gln Gly Leu Gln Val Pro Tyr Thr
1               5

<210> SEQ ID NO 174
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 174

Phe Gln Gly Ser His Ile Pro Tyr Thr
1               5

<210> SEQ ID NO 175
<211> LENGTH: 9
<212> TYPE: PRT
<213> ORGANISM: Artificial Sequence
<220> FEATURE:
<223> OTHER INFORMATION: anti-CD47 antibody molecule or antigen-binding portion LCDR3

<400> SEQUENCE: 175

Phe Gln Gly Ser His Thr Pro Tyr Thr
1               5

<210> SEQ ID NO 176
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 176

Phe Gln Gly Ser Gln Thr Pro Tyr Thr
1               5

<210> SEQ ID NO 177
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 177

Phe Gln Gly Ser Gln Val Pro Tyr Thr
1               5

<210> SEQ ID NO 178
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 178

Leu Gln Gly Ser His Ile Pro Tyr Thr
1               5

<210> SEQ ID NO 179
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 179

Leu Gln Gly Ser His Thr Pro Tyr Thr
1               5

<210> SEQ ID NO 180
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 180

Leu Gln Gly Ser His Val Pro Tyr Thr
1               5

<210> SEQ ID NO 181

```
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 181

Leu Gln Gly Ser Gln Thr Pro Tyr Thr
1               5

<210> SEQ ID NO 182
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 182

Leu Gln Gly Ser Gln Val Pro Tyr Thr
1               5

<210> SEQ ID NO 183
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 183

Met Gln Ala Leu Gln Val Pro Tyr Thr
1               5

<210> SEQ ID NO 184
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 184

Met Gln Ala Ser His Ile Pro Tyr Thr
1               5

<210> SEQ ID NO 185
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 185

Met Gln Ala Ser His Thr Pro Tyr Thr
1               5

<210> SEQ ID NO 186
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 186
```

Met Gln Ala Ser Gln Ile Pro Tyr Thr
1               5

<210> SEQ ID NO 187
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 187

Met Gln Ala Ser Gln Thr Pro Tyr Thr
1               5

<210> SEQ ID NO 188
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 188

Met Gln Gly Leu His Val Pro Tyr Thr
1               5

<210> SEQ ID NO 189
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 189

Met Gln Gly Leu Gln Val Pro Tyr Thr
1               5

<210> SEQ ID NO 190
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 190

Met Gln Gly Ser His Ile Pro Tyr Thr
1               5

<210> SEQ ID NO 191
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 191

Met Gln Gly Ser His Thr Pro Tyr Thr
1               5

<210> SEQ ID NO 192
<211> LENGTH: 9
<212> TYPE: PRT
<213> ORGANISM: Artificial Sequence
<220> FEATURE:

<223> OTHER INFORMATION: anti-CD47 antibody molecule or antigen-binding
      portion LCDR3

<400> SEQUENCE: 192

Met Gln Gly Ser Gln Ile Pro Tyr Thr
1               5

<210> SEQ ID NO 193
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 193

Met Gln Gly Ser Gln Thr Pro Tyr Thr
1               5

<210> SEQ ID NO 194
<211> LENGTH: 9
<212> TYPE: PRT
<213> ORGANISM: Artificial Sequence
<220> FEATURE:
<223> OTHER INFORMATION: anti-CD47 antibody molecule or antigen-binding
      portion LCDR3

<400> SEQUENCE: 194

Met Gln Gly Ser Gln Val Pro Tyr Thr
1               5

<210> SEQ ID NO 195
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 195

Gly Tyr Ser Phe Thr Asn Tyr Asn Ile Gly
1               5                   10

<210> SEQ ID NO 196
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 196

Gly Tyr Ser Phe Thr Asn Tyr Asn Met His
1               5                   10

<210> SEQ ID NO 197
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 197

Gly Tyr Ser Phe Thr Asn Tyr Ser Ile His
1               5                   10

```
<210> SEQ ID NO 198
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 198

Gly Tyr Ser Phe Thr Ser Tyr Asn Ile His
1               5                   10

<210> SEQ ID NO 199
<211> LENGTH: 10
<212> TYPE: PRT
<213> ORGANISM: Artificial Sequence
<220> FEATURE:
<223> OTHER INFORMATION: anti-CD47 antibody molecule or antigen-binding
      portion HCDR1

<400> SEQUENCE: 199

Gly Tyr Ser Phe Thr Ser Tyr Asn Met His
1               5                   10

<210> SEQ ID NO 200
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 200

Ile Gly Thr Ile Tyr Pro Gly Asp Asp Asp Thr Arg Tyr Asn Pro Lys
1               5                   10                  15

Phe Gln Gly

<210> SEQ ID NO 201
<211> LENGTH: 19
<212> TYPE: PRT
<213> ORGANISM: Artificial Sequence
<220> FEATURE:
<223> OTHER INFORMATI
    ON: anti-CD47 antibody molecule or antigen-binding portion HCDR2

<400> SEQUENCE: 201

Met Gly Ile Ile Tyr Pro Gly Asp Asp Asp Thr Arg Tyr Asn Pro Lys
1               5                   10                  15

Phe Gln Gly

<210> SEQ ID NO 202
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 202

Met Gly Ile Ile Tyr Pro Gly Asp Asp Asp Thr Arg Tyr Asn Pro Ser
1               5                   10                  15

Phe Gln Gly

<210> SEQ ID NO 203
<211> LENGTH: 19
<212> TYPE: PRT
```

```
<213> ORGANISM: Artificial Sequence
<220> FEATURE:
<223> OTHER INFORMATION: anti-CD47 antibody molecule or antigen-binding
      portion HCDR2

<400> SEQUENCE: 203

Met Gly Ile Ile Tyr Pro Gly Asp Asp Asp Thr Ser Tyr Asn Pro Lys
1               5                   10                  15

Phe Gln Gly

<210> SEQ ID NO 204
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 204

Met Gly Ile Ile Tyr Pro Gly Asp Asp Asp Thr Ser Tyr Asn Gln Lys
1               5                   10                  15

Phe Gln Gly

<210> SEQ ID NO 205
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 205

Met Gly Ile Ile Tyr Pro Gly Asp Ser Asp Thr Arg Tyr Asn Pro Lys
1               5                   10                  15

Phe Gln Gly

<210> SEQ ID NO 206
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 206

Met Gly Ile Ile Tyr Pro Gly Asp Ser Asp Thr Arg Tyr Asn Pro Ser
1               5                   10                  15

Phe Gln Gly

<210> SEQ ID NO 207
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 207

Met Gly Ile Ile Tyr Pro Gly Asp Ser Asp Thr Arg Tyr Asn Gln Lys
1               5                   10                  15

Phe Gln Gly

<210> SEQ ID NO 208
<211> LENGTH: 19
```

```
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 208

Met Gly Ile Ile Tyr Pro Gly Asp Ser Asp Thr Ser Tyr Asn Gln Ser
1               5                   10                  15

Phe Gln Gly

<210> SEQ ID NO 209
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 209

Met Gly Ile Ile Tyr Pro Gly Asn Asp Asp Thr Arg Tyr Asn Pro Lys
1               5                   10                  15

Phe Gln Gly

<210> SEQ ID NO 210
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 210

Met Gly Ile Ile Tyr Pro Gly Asn Asp Asp Thr Arg Tyr Asn Pro Ser
1               5                   10                  15

Phe Gln Gly

<210> SEQ ID NO 211
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 211

Met Gly Ile Ile Tyr Pro Gly Asn Asp Asp Thr Arg Tyr Asn Gln Lys
1               5                   10                  15

Phe Gln Gly

<210> SEQ ID NO 212
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 212

Met Gly Ile Ile Tyr Pro Gly Asn Ser Asp Thr Arg Tyr Asn Pro Lys
1               5                   10                  15

Phe Gln Gly

<210> SEQ ID NO 213
```

```
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 213

Met Gly Ile Ile Tyr Pro Gly Asn Ser Asp Thr Arg Tyr Asn Pro Ser
1               5                   10                  15

Phe Gln Gly

<210> SEQ ID NO 214
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 214

Met Gly Ile Ile Tyr Pro Gly Asn Ser Asp Thr Arg Tyr Asn Gln Lys
1               5                   10                  15

Phe Gln Gly

<210> SEQ ID NO 215
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 215

Met Gly Ile Ile Tyr Pro Gly Asn Ser Asp Thr Arg Tyr Asn Gln Arg
1               5                   10                  15

Phe Gln Gly

<210> SEQ ID NO 216
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 216

Met Gly Ile Ile Tyr Pro Gly Asn Ser Asp Thr Arg Tyr Asn Gln Ser
1               5                   10                  15

Phe Gln Gly

<210> SEQ ID NO 217
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 217

Met Gly Ile Ile Tyr Pro Gly Asn Ser Asp Thr Arg Tyr Ser Pro Lys
1               5                   10                  15

Phe Gln Gly
```

```
<210> SEQ ID NO 218
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 218

Met Gly Ile Ile Tyr Pro Gly Asn Ser Asp Thr Arg Tyr Ser Pro Ser
1               5                   10                  15

Phe Gln Gly

<210> SEQ ID NO 219
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 219

Met Gly Ile Ile Tyr Pro Gly Asn Ser Asp Thr Ser Tyr Asn Pro Lys
1               5                   10                  15

Phe Gln Gly

<210> SEQ ID NO 220
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 220

Met Gly Ile Ile Tyr Pro Gly Asn Ser Asp Thr Ser Tyr Asn Pro Arg
1               5                   10                  15

Phe Gln Gly

<210> SEQ ID NO 221
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 221

Met Gly Ile Ile Tyr Pro Gly Asn Ser Asp Thr Ser Tyr Asn Pro Ser
1               5                   10                  15

Phe Gln Gly

<210> SEQ ID NO 222
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 222

Met Gly Ile Ile Tyr Pro Gly Asn Ser Asp Thr Ser Tyr Asn Gln Lys
1               5                   10                  15

Phe Gln Gly
```

<210> SEQ ID NO 223
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 223

Met Gly Ile Ile Tyr Pro Gly Asn Ser Asp Thr Ser Tyr Ser Pro Lys
1               5                   10                  15

Phe Gln Gly

<210> SEQ ID NO 224
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 224

Met Gly Thr Ile Tyr Pro Gly Asp Asp Thr Arg Tyr Asn Pro Lys
1               5                   10                  15

Phe Gln Gly

<210> SEQ ID NO 225
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 225

Met Gly Thr Ile Tyr Pro Gly Asp Asp Thr Arg Tyr Asn Pro Ser
1               5                   10                  15

Phe Gln Gly

<210> SEQ ID NO 226
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 226

Met Gly Thr Ile Tyr Pro Gly Asp Asp Thr Arg Tyr Asn Gln Lys
1               5                   10                  15

Phe Gln Gly

<210> SEQ ID NO 227
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 227

Met Gly Thr Ile Tyr Pro Gly Asp Asp Thr Arg Tyr Asn Gln Asn
1               5                   10                  15

Phe Gln Gly

<210> SEQ ID NO 228
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 228

Met Gly Thr Ile Tyr Pro Gly Asp Asp Asp Thr Arg Tyr Asn Gln Ser
1               5                   10                  15

Phe Gln Gly

<210> SEQ ID NO 229
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 229

Met Gly Thr Ile Tyr Pro Gly Asp Asp Asp Thr Arg Tyr Ser Pro Lys
1               5                   10                  15

Phe Gln Gly

<210> SEQ ID NO 230
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 230

Met Gly Thr Ile Tyr Pro Gly Asp Asp Asp Thr Arg Tyr Ser Pro Ser
1               5                   10                  15

Phe Gln Gly

<210> SEQ ID NO 231
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 231

Met Gly Thr Ile Tyr Pro Gly Asp Asp Asp Thr Arg Tyr Ser Gln Lys
1               5                   10                  15

Phe Gln Gly

<210> SEQ ID NO 232
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 232

Met Gly Thr Ile Tyr Pro Gly Asp Asp Asp Thr Ser Tyr Ser Gln Lys
1               5                   10                  15

Phe Gln Gly

<210> SEQ ID NO 233
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 233

Met Gly Thr Ile Tyr Pro Gly Asp Gly Asp Thr Ser Tyr Asn Pro Ser
1               5                   10                  15

Phe Gln Gly

<210> SEQ ID NO 234
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 234

Met Gly Thr Ile Tyr Pro Gly Asp Asn Asp Thr Ser Tyr Asn Pro Ser
1               5                   10                  15

Phe Gln Gly

<210> SEQ ID NO 235
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 235

Met Gly Thr Ile Tyr Pro Gly Asp Ser Asp Thr Lys Tyr Asn Pro Lys
1               5                   10                  15

Phe Gln Gly

<210> SEQ ID NO 236
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 236

Met Gly Thr Ile Tyr Pro Gly Asp Ser Asp Thr Arg Tyr Asn Pro Ser
1               5                   10                  15

Phe Gln Gly

<210> SEQ ID NO 237
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 237

Met Gly Thr Ile Tyr Pro Gly Asp Ser Asp Thr Arg Tyr Ser Pro Lys
1               5                   10                  15

```
<210> SEQ ID NO 238
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 238
```

Met Gly Thr Ile Tyr Pro Gly Asp Ser Asp Thr Arg Tyr Ser Pro Arg
1               5                   10                  15

Phe Gln Gly

```
<210> SEQ ID NO 239
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 239
```

Met Gly Thr Ile Tyr Pro Gly Asp Ser Asp Thr Arg Tyr Ser Pro Ser
1               5                   10                  15

Phe Gln Gly

```
<210> SEQ ID NO 240
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 240
```

Met Gly Thr Ile Tyr Pro Gly Asp Ser Asp Thr Arg Tyr Ser Gln Lys
1               5                   10                  15

Phe Gln Gly

```
<210> SEQ ID NO 241
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 241
```

Met Gly Thr Ile Tyr Pro Gly Asp Ser Asp Thr Arg Tyr Ser Gln Ser
1               5                   10                  15

Phe Gln Gly

```
<210> SEQ ID NO 242
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 242
```

Met Gly Thr Ile Tyr Pro Gly Asp Ser Asp Thr Ser Tyr Asn His Lys

```
<210> SEQ ID NO 243
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 243

Met Gly Thr Ile Tyr Pro Gly Asp Ser Asp Thr Ser Tyr Asn Pro Lys
1               5                   10                  15

Phe His Gly

<210> SEQ ID NO 244
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 244

Met Gly Thr Ile Tyr Pro Gly Asp Ser Asp Thr Ser Tyr Asn Pro Arg
1               5                   10                  15

Phe Gln Gly

<210> SEQ ID NO 245
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 245

Met Gly Thr Ile Tyr Pro Gly Asp Ser Asp Thr Ser Tyr Asn Pro Ser
1               5                   10                  15

Phe Gln Gly

<210> SEQ ID NO 246
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 246

Met Gly Thr Ile Tyr Pro Gly Asp Ser Asp Thr Ser Tyr Asn Gln Lys
1               5                   10                  15

Phe Gln Gly

<210> SEQ ID NO 247
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 247
```

Met Gly Thr Ile Tyr Pro Gly Asp Ser Asp Thr Ser Tyr Asn Gln Ser
1               5                   10                  15

Phe Gln Gly

<210> SEQ ID NO 248
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 248

Met Gly Thr Ile Tyr Pro Gly Asp Ser Asp Thr Ser Tyr Ser Pro Lys
1               5                   10                  15

Phe Gln Gly

<210> SEQ ID NO 249
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 249

Met Gly Thr Ile Tyr Pro Gly Asp Ser Asp Thr Ser Tyr Ser Pro Ser
1               5                   10                  15

Phe Gln Gly

<210> SEQ ID NO 250
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 250

Met Gly Thr Ile Tyr Pro Gly Asp Ser Asp Thr Ser Tyr Ser Gln Lys
1               5                   10                  15

Phe Gln Gly

<210> SEQ ID NO 251
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 251

Met Gly Thr Ile Tyr Pro Gly Asn Asp Asp Thr Lys Tyr Ser Pro Lys
1               5                   10                  15

Phe Gln Gly

<210> SEQ ID NO 252
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 252

```
Met Gly Thr Ile Tyr Pro Gly Asn Asp Asp Thr Arg Tyr Asn Pro Lys
1               5                   10                  15

Phe Gln Gly
```

<210> SEQ ID NO 253
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 253

```
Met Gly Thr Ile Tyr Pro Gly Asn Asp Asp Thr Arg Tyr Asn Pro Ser
1               5                   10                  15

Phe Gln Gly
```

<210> SEQ ID NO 254
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 254

```
Met Gly Thr Ile Tyr Pro Gly Asn Asp Asp Thr Arg Tyr Asn Gln Lys
1               5                   10                  15

Phe Gln Gly
```

<210> SEQ ID NO 255
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 255

```
Met Gly Thr Ile Tyr Pro Gly Asn Asp Asp Thr Arg Tyr Asn Gln Ser
1               5                   10                  15

Phe Gln Gly
```

<210> SEQ ID NO 256
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 256

```
Met Gly Thr Ile Tyr Pro Gly Asn Asp Asp Thr Arg Tyr Ser Pro Lys
1               5                   10                  15

Phe Gln Gly
```

<210> SEQ ID NO 257
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

```
<400> SEQUENCE: 257

Met Gly Thr Ile Tyr Pro Gly Asn Asp Asp Thr Arg Tyr Ser Pro Ser
1               5                   10                  15

Phe Gln Gly

<210> SEQ ID NO 258
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 258

Met Gly Thr Ile Tyr Pro Gly Asn Asp Asp Thr Arg Tyr Ser Gln Lys
1               5                   10                  15

Phe Gln Gly

<210> SEQ ID NO 259
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 259

Met Gly Thr Ile Tyr Pro Gly Asp Asp Asp Thr Ser Tyr Asn Pro Lys
1               5                   10                  15

Phe Gln Gly

<210> SEQ ID NO 260
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 260

Met Gly Thr Ile Tyr Pro Gly Asp Asp Asp Thr Ser Tyr Asn Pro Ser
1               5                   10                  15

Phe Gln Gly

<210> SEQ ID NO 261
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 261

Met Gly Thr Ile Tyr Pro Gly Asp Asp Asp Thr Ser Tyr Asn Gln Lys
1               5                   10                  15

Phe Gln Gly

<210> SEQ ID NO 262
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2
```

<400> SEQUENCE: 262

Met Gly Thr Ile Tyr Pro Gly Asn Asp Asp Thr Ser Tyr Asn Gln Ser
1               5                   10                  15

Phe Gln Gly

<210> SEQ ID NO 263
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 263

Met Gly Thr Ile Tyr Pro Gly Asn Asp Asp Thr Ser Tyr Ser Pro Lys
1               5                   10                  15

Phe Gln Gly

<210> SEQ ID NO 264
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 264

Met Gly Thr Ile Tyr Pro Gly Asn Asp Asp Thr Ser Tyr Ser Pro Arg
1               5                   10                  15

Phe Gln Gly

<210> SEQ ID NO 265
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 265

Met Gly Thr Ile Tyr Pro Gly Asn Asp Asp Thr Ser Tyr Ser Pro Ser
1               5                   10                  15

Phe Gln Gly

<210> SEQ ID NO 266
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 266

Met Gly Thr Ile Tyr Pro Gly Asn Asp Asp Thr Ser Tyr Ser Gln Ser
1               5                   10                  15

Phe Gln Gly

<210> SEQ ID NO 267
<211> LENGTH: 19
<212> TYPE: PRT
<213> ORGANISM: Artificial Sequence
<220> FEATURE:
<223> OTHER INFORMATION: anti-CD47 antibody molecule or antigen-binding portion HCDR2

<400> SEQUENCE: 267

Met Gly Thr Ile Tyr Pro Gly Asn Asp Gly Thr Arg Tyr Asn Gln Lys
1               5                   10                  15

Phe Gln Gly

<210> SEQ ID NO 268
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 268

Met Gly Thr Ile Tyr Pro Gly Asn Gly Asp Thr Ser Tyr Asn His Lys
1               5                   10                  15

Phe Gln Gly

<210> SEQ ID NO 269
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 269

Met Gly Thr Ile Tyr Pro Gly Asn Gly Asp Thr Ser Tyr Asn Gln Lys
1               5                   10                  15

Phe Gln Gly

<210> SEQ ID NO 270
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 270

Met Gly Thr Ile Tyr Pro Gly Asn Asn Asp Thr Ser Tyr Asn Pro Lys
1               5                   10                  15

Phe Gln Gly

<210> SEQ ID NO 271
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 271

Met Gly Thr Ile Tyr Pro Gly Asn Ser Asp Thr Arg Tyr Asn His Ser
1               5                   10                  15

Phe Gln Gly

<210> SEQ ID NO 272
<211> LENGTH: 19
<212> TYPE: PRT
<213> ORGANISM: Artificial Sequence
<220> FEATURE:

```
<223> OTHER INFORMATION: anti-CD47 antibody molecule or antigen-binding
      portion HCDR2

<400> SEQUENCE: 272

Met Gly Thr Ile Tyr Pro Gly Asn Ser Asp Thr Arg Tyr Asn Pro Ser
1               5                   10                  15

Phe Gln Gly

<210> SEQ ID NO 273
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 273

Met Gly Thr Ile Tyr Pro Gly Asn Ser Asp Thr Arg Tyr Asn Gln Lys
1               5                   10                  15

Phe Gln Gly

<210> SEQ ID NO 274
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 274

Met Gly Thr Ile Tyr Pro Gly Asn Ser Asp Thr Arg Tyr Asn Gln Ser
1               5                   10                  15

Phe Gln Gly

<210> SEQ ID NO 275
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 275

Met Gly Thr Ile Tyr Pro Gly Asn Ser Asp Thr Arg Tyr Ser Pro Lys
1               5                   10                  15

Phe Gln Gly

<210> SEQ ID NO 276
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 276

Met Gly Thr Ile Tyr Pro Gly Asn Ser Asp Thr Arg Tyr Ser Pro Ser
1               5                   10                  15

Phe Gln Gly

<210> SEQ ID NO 277
<211> LENGTH: 19
<212> TYPE: PRT
<213> ORGANISM: Artificial Sequence
```

```
<220> FEATURE:
<223> OTHER INFORMATION: anti-CD47 antibody molecule or antigen-binding
      portion HCDR2

<400> SEQUENCE: 277

Met Gly Thr Ile Tyr Pro Gly Asn Ser Asp Thr Arg Tyr Ser Gln Lys
1               5                   10                  15

Phe Gln Gly

<210> SEQ ID NO 278
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 278

Met Gly Thr Ile Tyr Pro Gly Asn Ser Asp Thr Ser Tyr Asn Pro Arg
1               5                   10                  15

Phe Gln Gly

<210> SEQ ID NO 279
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 279

Met Gly Thr Ile Tyr Pro Gly Asn Ser Asp Thr Ser Tyr Asn Gln Lys
1               5                   10                  15

Phe Gln Gly

<210> SEQ ID NO 280
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 280

Met Gly Thr Ile Tyr Pro Gly Asn Ser Asp Thr Ser Tyr Asn Gln Ser
1               5                   10                  15

Phe Gln Gly

<210> SEQ ID NO 281
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 281

Met Gly Thr Ile Tyr Pro Gly Asn Ser Asp Thr Ser Tyr Ser Pro Lys
1               5                   10                  15

Phe Gln Gly

<210> SEQ ID NO 282
<211> LENGTH: 19
<212> TYPE: PRT
```

```
<213> ORGANISM: Artificial Sequence
<220> FEATURE:
<223> OTHER INFORMATION: anti-CD47 antibody molecule or antigen-binding
      portion HCDR2

<400> SEQUENCE: 282

Met Gly Thr Ile Tyr Pro Gly Asn Ser Asp Thr Ser Tyr Ser Pro Ser
1               5                   10                  15

Phe Gln Gly

<210> SEQ ID NO 283
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 283

Met Gly Thr Ile Tyr Pro Gly Asn Ser Asp Thr Ser Tyr Ser Gln Lys
1               5                   10                  15

Phe Gln Gly

<210> SEQ ID NO 284
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 284

Met Gly Thr Ile Tyr Ser Gly Asn Ser Asp Thr Ser Tyr Ser Pro Ser
1               5                   10                  15

Phe Gln Gly

<210> SEQ ID NO 285
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 285

Met Gly Thr Ile Tyr Pro Gly Asn Asp Asp Thr Arg Tyr Ser Gln Ser
1               5                   10                  15

Phe Gln Gly

<210> SEQ ID NO 286
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 286

Met Gly Thr Ile Tyr Pro Gly Asn Asp Asp Thr Ser Tyr Asn His Lys
1               5                   10                  15

Phe Gln Gly

<210> SEQ ID NO 287
<211> LENGTH: 19
```

```
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 287

Met Gly Thr Ile Tyr Pro Gly Asn Asp Asp Thr Ser Tyr Asn Pro Lys
1               5                   10                  15

Phe Gln Gly

<210> SEQ ID NO 288
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 288

Met Gly Thr Ile Tyr Pro Gly Asn Asp Asp Thr Ser Tyr Asn Pro Ser
1               5                   10                  15

Phe Gln Gly

<210> SEQ ID NO 289
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 289

Gly Gly Ala Arg Ala Met Asp Tyr
1               5

<210> SEQ ID NO 290
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 290

Gly Gly Cys Arg Ala Leu Asp Tyr
1               5

<210> SEQ ID NO 291
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 291

Gly Gly Cys Arg Ala Met Asp Tyr
1               5

<210> SEQ ID NO 292
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3
```

```
<400> SEQUENCE: 292

Gly Gly Cys Arg Ala Met Gly Tyr
1               5

<210> SEQ ID NO 293
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 293

Gly Gly Asp Arg Ala Met Asp Tyr
1               5

<210> SEQ ID NO 294
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 294

Gly Gly Glu Arg Ala Met Asp Tyr
1               5

<210> SEQ ID NO 295
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 295

Gly Gly Phe Arg Ala Glu Asp Tyr
1               5

<210> SEQ ID NO 296
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 296

Gly Gly Phe Arg Ala Gln Asp Tyr
1               5

<210> SEQ ID NO 297
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 297

Gly Gly Gly Arg Ala Met Asp Tyr
1               5

<210> SEQ ID NO 298
<211> LENGTH: 8
```

```
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 298

Gly Gly His Arg Ala Glu Asp Tyr
1               5

<210> SEQ ID NO 299
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 299

Gly Gly His Arg Ala Met Asp Tyr
1               5

<210> SEQ ID NO 300
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 300

Gly Gly Leu Arg Ala Met Asp Tyr
1               5

<210> SEQ ID NO 301
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 301

Gly Gly Leu Arg Thr Met Asp Tyr
1               5

<210> SEQ ID NO 302
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 302

Gly Gly Met Arg Ala Met Asp Tyr
1               5

<210> SEQ ID NO 303
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 303

Gly Gly Asn Arg Ala Lys Asp Tyr
```

```
<210> SEQ ID NO 304
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 304

Gly Gly Asn Arg Ala Met Asp Tyr
1               5

<210> SEQ ID NO 305
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 305

Gly Gly Gln Arg Ala Met Asp Tyr
1               5

<210> SEQ ID NO 306
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 306

Gly Gly Arg Arg Ala Met Asp Tyr
1               5

<210> SEQ ID NO 307
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 307

Gly Gly Ser Arg Ala Lys Asp Tyr
1               5

<210> SEQ ID NO 308
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 308

Gly Gly Ser Arg Ala Met Asp Tyr
1               5

<210> SEQ ID NO 309
<211> LENGTH: 8
<212> TYPE: PRT
<213> ORGANISM: Artificial Sequence
<220> FEATURE:
<223> OTHER INFORMATION: anti-CD47 antibody molecule or antigen-binding
``` portion HCDR3

<400> SEQUENCE: 309

Gly Gly Thr Arg Ala Met Asp Tyr
1               5

<210> SEQ ID NO 310
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 310

Gly Gly Val Arg Ala Thr Asp Tyr
1               5

<210> SEQ ID NO 311
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 311

Gly Gly Trp Arg Ala Met Asp Tyr
1               5

<210> SEQ ID NO 312
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 312

Gly Gly Tyr His Ala Met Asp Tyr
1               5

<210> SEQ ID NO 313
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 313

Gly Gly Tyr Lys Ala Met Asp Tyr
1               5

<210> SEQ ID NO 314
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 314

Gly Gly Tyr Arg Ala Ala Asp Tyr
1               5

<210> SEQ ID NO 315

```
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 315

Gly Gly Tyr Arg Ala Leu Asp Tyr
1               5

<210> SEQ ID NO 316
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 316

Gly Gly Tyr Arg Ala Pro Asp Tyr
1               5

<210> SEQ ID NO 317
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 317

Gly Gly Tyr Arg Ala Arg Asp Tyr
1               5

<210> SEQ ID NO 318
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 318

Gly Gly Tyr Arg Ala Ser Asp Tyr
1               5

<210> SEQ ID NO 319
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 319

Gly Gly Tyr Arg Ala Thr Asp Tyr
1               5

<210> SEQ ID NO 320
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 320
```

```
Gly Gly Tyr Arg Ala Val Asp Tyr
1               5

<210> SEQ ID NO 321
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 321

Gly Gly Tyr Arg Ile Met Asp Tyr
1               5

<210> SEQ ID NO 322
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 322

Gly Gly Tyr Arg Thr Glu Asp Tyr
1               5

<210> SEQ ID NO 323
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 323

Gly Gly Tyr Arg Thr Met Asp Tyr
1               5

<210> SEQ ID NO 324
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 324

Gly Gly Tyr Arg Thr Thr Asp Tyr
1               5

<210> SEQ ID NO 325
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 325

Gly Gly Tyr Arg Val Met Asp Tyr
1               5

<210> SEQ ID NO 326
<211> LENGTH: 8
<212> TYPE: PRT
<213> ORGANISM: Artificial Sequence
<220> FEATURE:
```

```
<223> OTHER INFORMATION: anti-CD47 antibody molecule or antigen-binding
      portion HCDR3

<400> SEQUENCE: 326

Gly Gly Tyr Arg Trp Met Asp Tyr
1               5

<210> SEQ ID NO 327
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 327

Gln Gly Tyr Arg Ala Met Asp Tyr
1               5

<210> SEQ ID NO 328
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 328

Arg Ser Ser Gln Ser Leu Leu His Ser Lys Gly Asn Thr Tyr Leu Gly
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: anti-CD47 antibody molecule or antigen-binding
      portion LCDR1

<400> SEQUENCE: 329

Arg Ser Ser Gln Ser Leu Leu His Ser Asn Tyr Asn Thr Tyr Leu Gly
1               5                   10                  15

<210> SEQ ID NO 330
<211> LENGTH: 7
<212> TYPE: PRT
<213> ORGANISM: Artificial Sequence
<220> FEATURE:
<223> OTHER INFORMATION: anti-CD47 antibody molecule or antigen-binding
      portion LCDR2

<400> SEQUENCE: 330

Lys Gly Ser Asn Arg Ala Ser
1               5

<210> SEQ ID NO 331
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 331

Met Gly Thr Ile Tyr Pro Gly Asn Ser Asp Thr Ser Tyr Asn His Lys
1               5                   10                  15

Phe Gln Gly
```

```
<210> SEQ ID NO 332
<211> LENGTH: 19
<212> TYPE: PRT
<213> ORGANISM: Artificial Sequence
<220> FEATURE:
<223> OTHER INFORMATION: anti-CD47 antibody molecule or antigen-binding
      portion HCDR2

<400> SEQUENCE: 332

Met Gly Thr Ile Tyr Pro Gly Asn Asp Asn Thr Lys Tyr Asn Gln Lys
1               5                   10                  15

Phe Gln Gly

<210> SEQ ID NO 333
<211> LENGTH: 8
<212> TYPE: PRT
<213> ORGANISM: Artificial Sequence
<220> FEATURE:
<223> OTHER INFORMATION: anti-CD47 antibody molecule or antigen-binding
      portion HCDR3

<400> SEQUENCE: 333

Gly Gly Asn Arg Ala Glu Asp Tyr
1               5
```